(12) United States Patent
Culler et al.

(10) Patent No.: US 10,669,561 B2
(45) Date of Patent: Jun. 2, 2020

(54) MICROORGANISMS FOR PRODUCING 4C-5C COMPOUNDS WITH UNSATURATION AND METHODS RELATED THERETO

(71) Applicant: Genomatica, Inc., California, CA (US)

(72) Inventors: Stephanie J. Culler, San Diego, CA (US); Mark J. Burk, San Diego, CA (US); Robin E. Osterhout, San Diego, CA (US); Priti Pharkya, San Diego, CA (US)

(73) Assignee: GENOMATICA, INC., San Diego, CA (US)

( * ) Notice: Subject to any disclaimer, the term of this patent is extended or adjusted under 35 U.S.C. 154(b) by 200 days.

(21) Appl. No.: 15/323,360

(22) PCT Filed: Jul. 2, 2015

(86) PCT No.: PCT/US2015/039037
§ 371 (c)(1),
(2) Date: Dec. 30, 2016

(87) PCT Pub. No.: WO2016/004334
PCT Pub. Date: Jan. 7, 2016

(65) Prior Publication Data
US 2017/0166931 A1   Jun. 15, 2017

Related U.S. Application Data

(60) Provisional application No. 62/020,901, filed on Jul. 3, 2014, provisional application No. 62/082,747, filed on Nov. 21, 2014.

(51) Int. Cl.
| | | |
|---|---|---|
| C12N 15/00 | (2006.01) | |
| C12N 1/20 | (2006.01) | |
| C12N 9/00 | (2006.01) | |
| C12N 9/02 | (2006.01) | |
| C12N 9/88 | (2006.01) | |

(Continued)

(52) U.S. Cl.
CPC .............. *C12P 7/04* (2013.01); *C12N 9/0006* (2013.01); *C12N 9/88* (2013.01); *C12N 9/90* (2013.01); *C12N 15/52* (2013.01); *C12P 5/026* (2013.01); *C12P 7/40* (2013.01); *Y02E 50/343* (2013.01)

(58) Field of Classification Search
None
See application file for complete search history.

(56) References Cited

U.S. PATENT DOCUMENTS

| | | |
|---|---|---|
| 2012/0021478 A1 | 1/2012 | Osterhout et al. |
| 2013/0109064 A1 | 5/2013 | Osterhout et al. |
| 2014/0141482 A1 | 5/2014 | Pearlman et al. |

*Primary Examiner* — Yong D Pak
(74) *Attorney, Agent, or Firm* — Kagan Binder, PLLC

(57) ABSTRACT

The invention provides a non-naturally occurring microbial organism having a butadiene, crotyl alcohol, 2,4-pentadienoate, 3-buten-2-ol, or 3-buten-1-ol, pathway. The microbial organism contains at least one exogenous nucleic acid encoding an enzyme in a pathway. The invention additionally provides a method for producing butadiene, crotyl alcohol, 2,4-pentadienoate, 3-buten-2-ol, or 3-buten-1-ol. The method can include culturing a butadiene, crotyl alcohol, 2,4-pentadienoate, 3-buten-2-ol, or 3-buten-1-ol-producing microbial organism, where the microbial organism expresses at least one exogenous nucleic acid encoding a pathway enzyme in a sufficient amount, and under conditions and for a sufficient period of time to produce butadiene, crotyl alcohol, 2,4-pentadienoate, 3-buten-2-ol, or 3-buten-1-ol.

20 Claims, 8 Drawing Sheets

Figure 4

(51) Int. Cl.
    *C12N 9/90*          (2006.01)
    *C07H 21/04*        (2006.01)
    *C12P 7/04*          (2006.01)
    *C12N 15/52*        (2006.01)
    *C12P 5/02*          (2006.01)
    *C12P 7/40*          (2006.01)
    *C12N 9/04*          (2006.01)

MICROORGANISMS FOR PRODUCING 4C-5C COMPOUNDS WITH UNSATURATION AND METHODS RELATED THERETO

PRIORITY CLAIM

This application claims the benefit of International Application No. PCT/US2015/039037, filed Jul. 2, 2015, which in turn claims the benefit of U.S. Provisional Patent Application Ser. No. 62/020,901 filed Jul. 3, 2014, and U.S. Provisional Patent Application Ser. No. 62/082,747 filed Nov. 21, 2014, both applications entitled MICROORGANISMS FOR PRODUCING 4C-5C COMPOUNDS WITH UNSATURATION AND METHODS RELATED THERETO, the entireties of said patent applications are incorporated herein by reference.

FIELD OF THE INVENTION

The present invention relates generally to metabolic and biosynthetic processes and microbial organisms capable of producing organic compounds, and more specifically to non-naturally occurring microbial organisms having an organic compound pathway, such as butadiene, crotyl alcohol, 3-buten-2-ol, 3-buten-1-ol, and 2,4-pentadienoate.

BACKGROUND OF THE INVENTION

Over 25 billion pounds of butadiene (1,3-butadiene, "BD") are produced annually and is applied in the manufacture of polymers such as synthetic rubbers and ABS resins, and chemicals such as hexamethylenediamine and 1,4-butanediol. For example, butadiene can be reacted with numerous other chemicals, such as other alkenes, e.g. styrene, to manufacture numerous copolymers, e.g. acrylonitrile 1,3-butadiene styrene (ABS), styrene-1,3-butadiene (SBR) rubber, styrene-1,3-butadiene latex. These materials are used in rubber, plastic, insulation, fiberglass, pipes, automobile and boat parts, food containers, and carpet backing. Butadiene is typically produced as a by-product of the steam cracking process for conversion of petroleum feedstocks such as naphtha, liquefied petroleum gas, ethane or natural gas to ethylene and other olefins.

The ability to manufacture butadiene from alternative and/or renewable feedstocks would represent a major advance in the quest for more sustainable chemical production processes.

One possible way to produce butadiene renewably involves fermentation of sugars or other feedstocks to produce diols, such as 1,4-butanediol or 1,3-butanediol, which are separated, purified, and then dehydrated to butadiene in a second step involving metal-based catalysis.

Direct fermentative production of butadiene from renewable feedstocks would obviate the need for dehydration steps and butadiene gas (bp—4.4° C.) would be continuously emitted from the fermenter and readily condensed and collected. Developing a fermentative production process would eliminate the need for fossil-based butadiene and would allow substantial savings in cost, energy, and harmful waste and emissions relative to petrochemically-derived butadiene.

Crotyl alcohol ("CrotOH"), also referred to as 2-buten-1-ol, is a valuable chemical intermediate. It serves as a precursor to crotyl halides, esters, and ethers, which in turn are chemical intermediates in the production of monomers, fine chemicals, agricultural chemicals, and pharmaceuticals. Exemplary fine chemical products include sorbic acid, trimethylhydroquinone, crotonic acid and 3-methoxybutanol. CrotOH is also a precursor to 1,3-butadiene. CrotOH is currently produced exclusively from petroleum feedstocks. For example Japanese Patent 47-013009 and U.S. Pat. Nos. 3,090,815, 3,090,816, and 3,542,883 describe a method of producing CrotOH by isomerization of 1,2-epoxybutane. The ability to manufacture CrotOH from alternative and/or renewable feedstocks would represent a major advance in the quest for more sustainable chemical production processes.

3-Buten-2-ol (also referenced to as methyl vinyl carbinol ("MVC")) is an intermediate that can be used to produce butadiene. There are significant advantages to use of MVC over 1,3-BDO because there are fewer separation steps and only one dehydration step. MVC can also be used as a solvent, a monomer for polymer production, or a precursor to fine chemicals. Accordingly, the ability to manufacture MVC from alternative and/or renewable feedstock would again present a significant advantage for sustainable chemical production processes.

2,4-Pentadienoate is a useful substituted butadiene derivative in its own right and a valuable intermediate en route to other substituted 1,3-butadiene derivatives, including, for example, 1-carbamoyl-1,3-butadienes which are accessible via Curtius rearrangement. The resultant N-protected-1,3-butadiene derivatives can be used in Diels alder reactions for the preparation of substituted anilines. 2,4-Pentadienoate can be used in the preparation of various polymers and co-polymers.

Thus, there exists a need for alternative methods for effectively producing commercial quantities of compounds such as butadiene, CrotOH, MVC or 2,4-pentadienoate. The present invention satisfies this need and provides related advantages as well.

SUMMARY OF THE INVENTION

In embodiments the invention provides a non-naturally occurring microbial organism having a pathway to butadiene, crotyl alcohol, 2,4-pentadienoate, or 3-buten-2-ol, said microbial organism comprising at least one exogenous nucleic acid encoding a pathway enzyme, wherein the enzyme is selected from the group consisting of (1E) 4-hydroxy 2-oxovalerate decarboxylase, (1 D) 3-hydroxybutyraldehyde dehydratase, (1N) 2-oxopent-3-enoyl-CoA synthetase or transferase, (1O) 2-oxopent-3-enoyl-CoA reductase, (1P) 2-hydroxypent-3-enoyl-CoA dehydratase/vinylisomerase, (1R) 2-hydroxypent-3-enoyl-CoA synthetase or transferase, (1F) 2-oxopent-3-enoate reductase, (1U) 2-hydroxypent-3-enoate vinylisomerase, and (1K) crotyl alcohol vinylisomerase. One or more additional pathway enzymes may be included in the microbial organism. The invention also provides methods for the production of butadiene, crotyl alcohol, 2,4-pentadienoate, or 3-buten-2-ol, comprising culturing the non-naturally occurring microorganism.

In other embodiments the invention provides a non-naturally occurring microbial organism having a pathway to butadiene, crotyl alcohol, 2,4-pentadienoate, or 3-buten-1-ol, said microbial organism comprising at least one exogenous nucleic acid encoding a pathway enzyme, the enzyme selected from the group consisting of (2E) 2-hydroxypent-4-enoate vinylisomerase, (2H) 2-hydroxypent-4-enoate mutase, and (2M) 3-hydroxypent-4-enoyl-CoA vinylisomerase. One or more additional pathway enzymes may be included in the microbial organism. The invention also provides methods for the production of butadiene, crotyl alcohol, 2,4-pentadienoate, or 3-buten-1-ol, comprising culturing the non-naturally occurring microorganism.

In other embodiments the invention provides a non-naturally occurring microbial organism having a pathway to butadiene, 2,4-pentadienoate, or 3-buten-2-ol, said microbial organism comprising at least one exogenous nucleic acid encoding a pathway enzyme, the enzyme selected from the group consisting of (3D) 3,4-dihydroxypentanoate dehydratase, (3E) 4-hydroxypent-2-enoate decarboxylase (3H) 3,4-dihydroxypentanoyl-CoA dehydratase, and (3J) 4-hydroxypent-2-enoyl-CoA transferase. The invention also provides methods for the production of butadiene, crotyl alcohol, 2,4-pentadienoate, or 3-buten-2-ol, comprising culturing the non-naturally occurring microorganism.

In other embodiments the invention provides a non-naturally occurring microbial organism having a pathway to convert crotyl alcohol to butadiene or 3-buten-2-ol, said microbial organism comprising at least one exogenous nucleic acid encoding a pathway enzyme, wherein the enzyme is selected from the group consisting of (4D) 3-buten-2-ol synthase, (4E) 3-buten-2-ol synthase, or (4F) crotyl alcohol isomerase.

DETAILED DESCRIPTION OF THE INVENTION

The product pathways described herein are specifically contemplated for use in the organisms, compositions and their uses, such as in methods to make the target products of 1,3-butadiene, crotyl alcohol, 3-buten-2-ol, 3-buten-1-ol or 2,4-pentadienoate or other product, and other embodiments as taught herein.

Embodiments of the disclosure are directed to the design of metabolic pathways, and the production and use of non-naturally occurring microbial organisms capable of producing butadiene, crotyl alcohol, 3-buten-2-ol, 3-buten-1-ol and/or 2,4-pentadienoate. As disclosed herein, metabolic pathways can be designed and recombinantly engineered to achieve the biosynthesis of butadiene, crotyl alcohol, 3-buten-2-ol, 3-buten-1-ol, and/or 2,4-pentadienoate in microbial organisms such as Escherichia coli and other cells or organisms. Biosynthetic production of butadiene, crotyl alcohol, 3-buten-2-ol, 3-buten-1-ol, and/or 2,4-pentadienoate can be performed by construction and fermentation of strains having the designed metabolic genotype.

Figure 1:
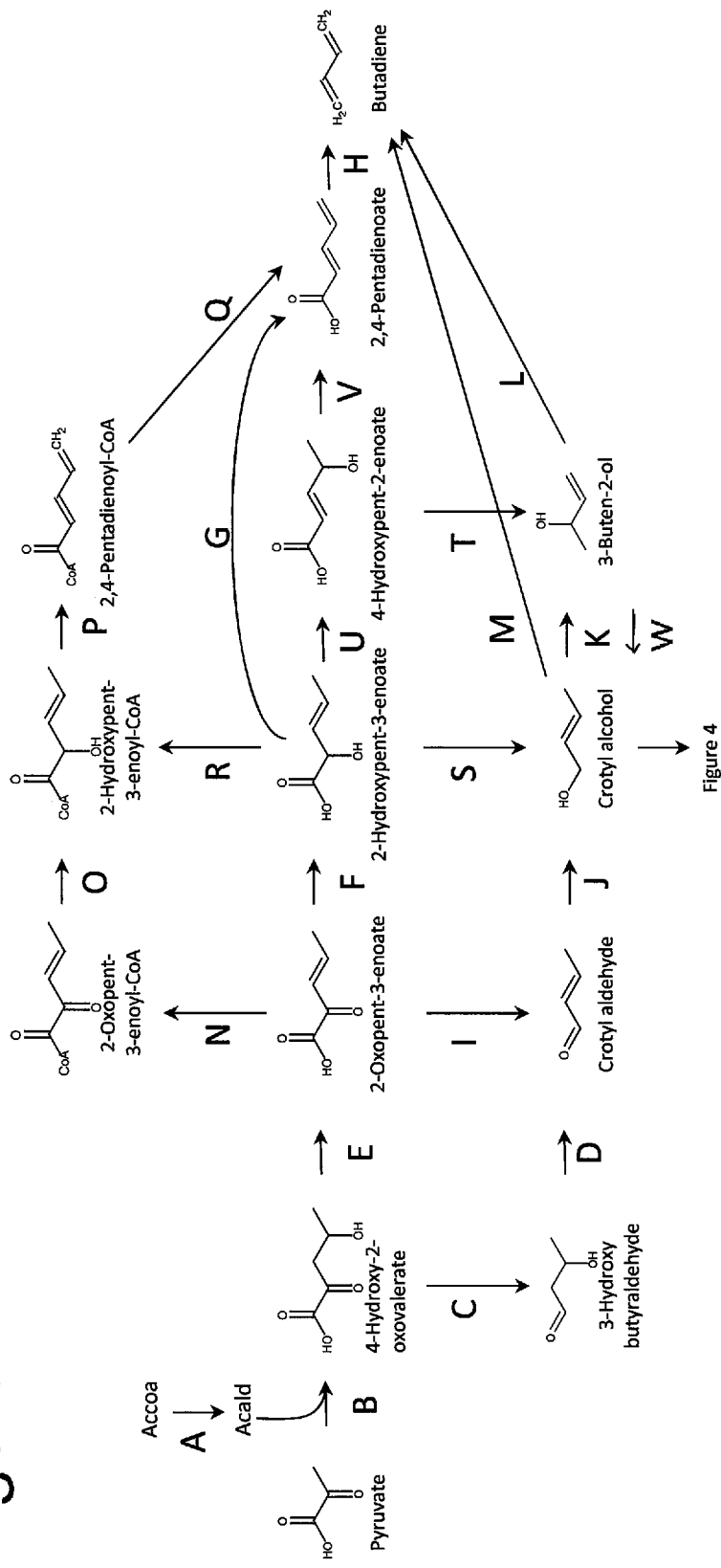
FIG. 1 shows pathways to butadiene from pyruvate and acetyl-CoA. Enzymes are A. acetyl-CoA reductase, B: 4-hydroxy 2-oxovalerate aldolase, C. 4-hydroxy 2-oxovalerate decarboxylase, D. 3-hydroxybutyraldehyde dehydratase, E. 4-hydroxy-2-oxovalerate 3-dehydratase, F. 2-oxopent-3-enoate reductase, G. 2-hydroxypent-3-enoate dehydratase/vinylisomerase, H. 2,4-pentadienoate decarboxylase, I. 2-oxopent-3-enoate decarboxylase, J. crotyl aldehyde reductase, K. crotyl alcohol vinylisomerase, L. 3-buten-2-ol dehydratase, M. crotyl alcohol dehydratase/vinylisomerase, N. 2-oxopent-3-enoyl-CoA synthetase or transferase, O. 2-oxopent-3-enoyl-CoA reductase, P. 2-hydroxypent-3-enoyl-CoA dehydratase/vinylisomerase, Q. 2,4-pentadienoyl-CoA synthetase, transferase or hydrolase, R. 2-hydroxypent-3-enoyl-CoA synthetase or transferase, S. 2-hydroxypent-3-enoate decarboxylase, T. 4-hyroxypent-2-enoate decarboxylase, U. 2-hydroxypent-3-enoate vinylisomerase, V. 4-hydroxypent-2-enoate dehydratase, W. vinylisomerase.

FIG. 1 provides exemplary pathways to butadiene from acetyl-CoA and pyruvate via intermediate 2-oxopent-3-enoate (step E) or 3-hydroxybutyraldehyde (step C). Also shown are pathways to the intermediate products (which may be desirably obtained as final products) of crotol alcohol, 3-buten-2-ol, 3-buten-1-ol, and/or 2,4-pentadienoate, which in certain pathway routes, can be intermediates in butadiene synthesis. In one pathway, acetyl-CoA is converted to acetaldehyde by acetyl-CoA reductase, and pyruvate and acetaldehyde are then converted to 4-hydroxy-2-oxovalerate by 4-hydroxy 2-oxovalerate aldolase.

With reference to FIG. 1, the intermediate 4-hydroxy-2-oxovalerate can be promoted to enter different pathways depending on the metabolic design. In one pathway ("E"), 4-hydroxy-2-oxovalerate can be converted to 2-oxopent-3-enoate in the presence of 4-hydroxy-2-oxovalerate 3-dehydratase. Pathway "E" can branch off into one or more different pathways depending on the metabolic design. For example, in pathway "E→N" 2-oxopent-3-enoate is converted to 2-oxopent-3-enoyl-CoA in the presence of 2-oxopent-3-enoyl-CoA synthetase or transferase (N); subsequent enzymatic conversions of intermediates can occur. As another example, in pathway "E→F" 2-oxopent-3-enoate is converted to 2-hydroxypent-3-enoate in the presence of 2-oxopent-3-enoate reductase (F); subsequent enzymatic conversions of intermediates can occur. If desired, the intermediate 2,4-pentadienoate can be obtained further downstream in the E→F branch of the pathway. As another example, in pathway "E→I" 2-oxopent-3-enoate is converted to crotyl aldehyde in the presence of 2-oxopent-3-enoate decarboxylase (I); subsequent enzymatic conversions of intermediates can occur. In desired, the intermediates such as crotol alcohol and/or 3-buten-2-ol can be obtained further downstream in the E→I branch of the pathway.

With reference to FIG. 1, the intermediate 4-hydroxy-2-oxovalerate can also be promoted to enter pathway ("C"), where 4-hydroxy-2-oxovalerate can be converted to 3-hydroxy butyraldehyde in the presence of 4-hydroxy 2-oxovalerate decarboxylase. Subsequently, 4-hydroxy 2-oxovalerate decarboxylase can be converted to crotyl aldehyde in the presence of 3-hydroxybutyraldehyde dehydratase (D). Crotyl aldehyde can be converted to crotyl alcohol, which can be an intermediate in the pathway, or can be obtained as a final product, by crotyl aldehyde reductase (J). Subsequently, crotyl alcohol can be converted to 3-buten-2-ol, which can be an intermediate in the pathway, or can be obtained as a final product, by crotyl alcohol vinylisomerase (K). 3-buten-2-ol from steps K or T can be isolated or from step T converted to crotyl alcohol enzymatically (W) or chemically. Crotyl alcohol can enter FIG. 4 or be isolated.

With reference to FIG. 1, the non-naturally occurring microbial organism can have any one of the following pathways: E; BE; ABE; EN; ENO; ENOP; ENOPQ; ENOPQH; EF; EFU; EFUV; EFUVH; EFR; EFRP; EFRPQ; EFRPQH; EFS; EFSK; EFSKL; EFSM; EFUT; EFUTL; EI; EIJ; EIJK; EIJKL; EIJM; BEN; BENO; BENOP; BENOPQ; BENOPQH; BEF; BEFU; BEFUV; BEFUVH; BEFR; BEFRP; BEFRPQ; BEFRPQH; BEF; BEFS; BEFSK; BEFSKL; BEFSM; BEFUT; BEFUTL; BEI; BEIJ; BEIJK; BEIJKL; BEIJM; ABEN; ABENO; ABENOP; ABENOPQ; ABENOPQH; ABEF; ABEFU; ABEFUV; ABEFUVH; ABEFR; ABEFRP; ABEFRPQ; ABEFRPQH; ABEF; ABEFS; ABEFSK; ABEFSKL; ABEFSM; ABEFUT; ABEFUTL; ABEI; ABEIJ; ABEIJK; ABEIJKL; ABEIJM; D; CD; BCD; ABCD; DJ; DJM; DJK; DJKL; CDJ; CDJM; CDJK; CDJKL; BCDJ; BCDJM; BCDJK; BCDJKL; ABCDJ; ABCDJM; ABCDJK; ABCDJKL; N; O; P; R; F; U; K; and each combination of any one or more of E, D, N, O, P, R, F, U and K with any one or more of steps of FIG. 1. In each of the embodiments of the above pathways where 3-buten-2-ol is produced from Step T it can be followed by Step W, conversion to crotyl alcohol. For example, EFUTW; BEFUTW; ABEFUTW.

In some embodiments, at least one of the pathway enzymes is encoded by nucleic acid that is heterologous to the host species. For example, the heterologous nucleic acid can be obtained from a microbial species other than the host species, such as a nucleic acid from a bacteria other than *E. coli* (i.e., a non-*E. coli* bacteria), wherein the heterologous nucleic acid is transformed into *E. coli* host organism to create any of the pathways of the disclosure. In some embodiments, two, three, four, five, six, etc., heterologous nucleic acids from one or more bacteria other than the host bacteria, are transformed into the bacterial host organism to create any of the pathways of the disclosure. For example, to create a pathway such as BEFUVH in a host organism, one can first determine what, if any, enzymes of the BEFUVH are naturally present in a desired host species. If B is native to the host species, but not EFUVH, the host can then be transformed with heterologous nucleic acids encoding EFUVH to create a pathway in the cell to form butadiene. This approach can be used to create a non-naturally occurring microbial organism having a pathway to butadiene, crotyl alcohol, 2,4-pentadienoate, or 3-buten-2-ol, having any of the pathways of the disclosure.

Figure 2:
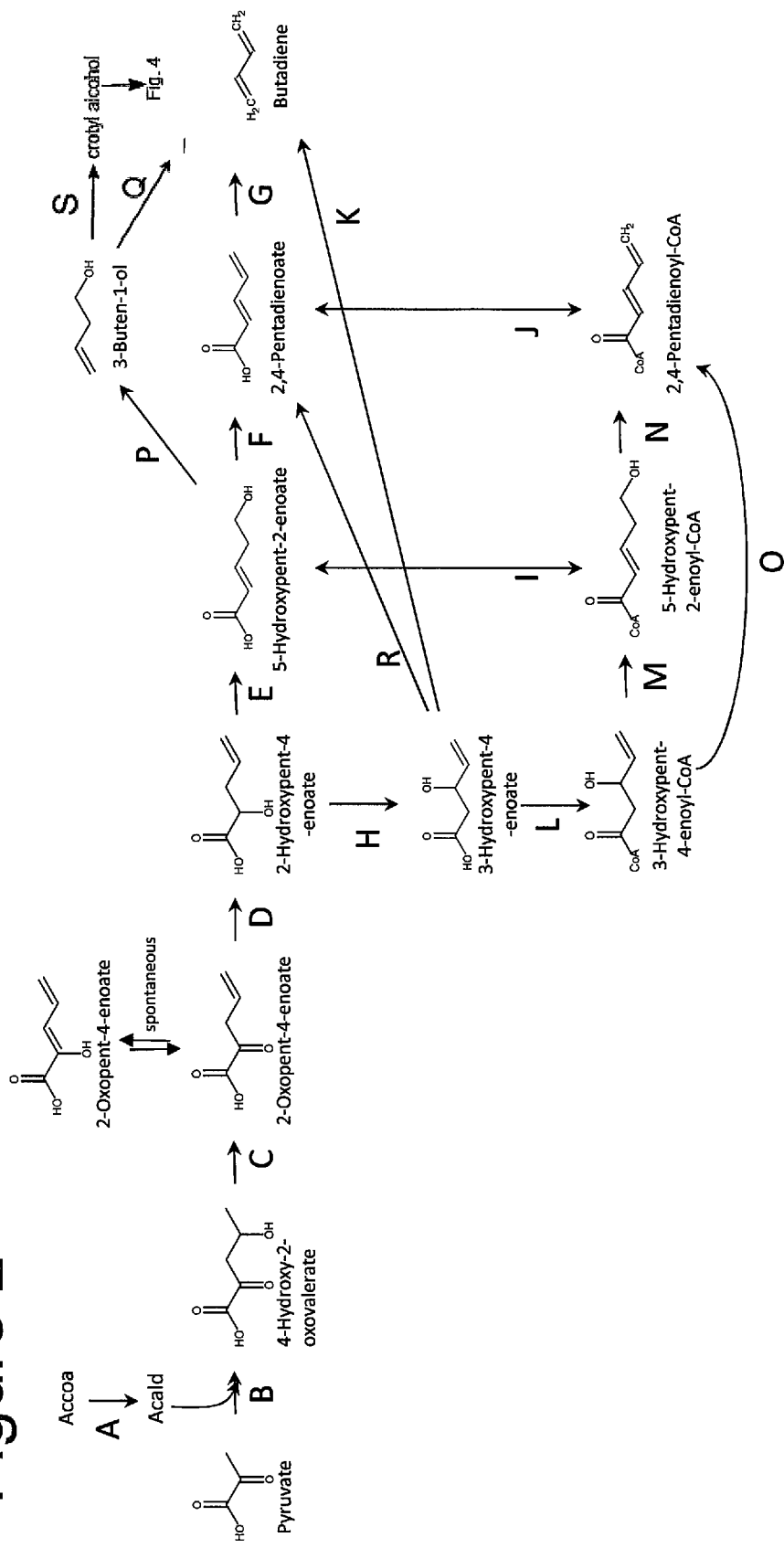
FIG. 2 shows pathways to butadiene from pyruvate and acetyl-CoA. Acetyl-CoA reductase, B. 4-hydroxy 2-oxovalerate aldolase, C. 4-hydroxy 2-oxovalerate dehydratase, D. 2-oxopent-4-enoate reductase, E. 2-hydroxypent-4-enoate vinylisomerase, F. 5-hydroxypent-2-enoate dehydratase, G. 2,4-pentadienoate decarboxylase, H. 2-hydroxypent-4-enoate mutase, I. 5-hydroxypent-2-enoyl-CoA synthetase, transferase or hydrolase, J. 2,4-pentadienoyl-CoA synthetase, transferase or hydrolase, K. 3-hydroxypent-4-enoate decarboxylase, L. 3-hydroxypent-4-enoyl-CoA synthetase or transferase, M. 3-hydroxypent-4-enoyl-CoA vinylisomerase, N. 2,4-pentadienoyl-CoA synthetase, hydrolase or transferase, O. 3-hydroxypent-4-enoyl-CoA dehydratase, P. 5-hydroxypent-2-enoate decarboxylase, Q. 3-buten-1-ol dehydratase, R. 3-hydroxypent-4-enoate dehydratase, S. vinylisomerase.

FIG. 2 provides exemplary pathways to butadiene from acetyl-CoA and pyruvate via intermediate 5-hydroxypent-2-enoate (step E) or 3-hydroxypent-4-enoate (step H). Also shown are pathways to the intermediate products (which may be desirably obtained as final products) of crotol alcohol, 3-buten-1-ol and/or 2,4-pentadienoate, which in certain pathway routes, can be intermediates in butadiene synthesis. In one pathway, acetyl-CoA is converted to acetaldehyde by acetyl-CoA reductase (A), and pyruvate and acetaldehyde then converted to 4-hydroxy-2-oxovalerate by 4-hydroxy 2-oxovalerate aldolase (B). 4-hydroxy-2-oxovalerate is converted to 2-oxopent-4-enoate by 4-hydroxy 2-oxovalerate dehydratase (C), and then 2-oxopent-4-enoate is converted to 2-hydroxypent-4-enoate by 2-oxopent-4-enoate reductase (D).

As shown in FIG. 2, the intermediate 2-hydroxypent-4-enoate can enter pathway branch "E" or "H." In pathway branch E, 2-hydroxypent-4-enoate is converted to 5-hydroxypent-2-enoate in the presence of 2-hydroxypent-4-enoate vinylisomerase. The intermediate 5-hydroxypent-2-enoate can then enter one or more of pathway branches (P, F, and/or I) before conversion to butadiene. 3-buten-1-ol can be converted to crotyl alcohol (S), which can be an intermediate in the pathway (entering FIG. 4), or can be obtained as a final product. In pathway branch H, 2-hydroxypent-4-enoate is converted to 3-hydroxypent-4-enoate in the presence of 2-hydroxypent-4-enoate mutase. The intermediate 3-hydroxypent-4-enoate can then enter one or more of pathway branches (R, K, and/or L) before conversion to butadiene.

With reference to FIG. 2, the non-naturally occurring microbial organism can have any one of the following pathways: E; DE; CDE; BCDE; ABCDE; EF; EFG; EP; EPQ; EI; EIN; EINJ; EINJG; ABCDEF; ABCDEFG; ABCDEP; ABCDEPQ; ABCDEI; ABCDEIN; ABCDEINJ; ABCDEINJG; BCDEF; BCDEFG; BCDEP; BCDEPQ; BCDEI; BCDEIN; BCDEINJ; BCDEINJG; CDEF; CDEFG; CDEP; CDEPQ; CDEI; CDEIN; CDEINJ; CDEINJG; DEF; DEFG; DEP; DEPQ; DEI; DEIN; DEINJ; DEINJG; H; DH; CDH; BCDH; ABCDH; HL; HLM; HLMN; HLMNJ; HLMNJG; HLO; HLOJ; HLOJG; HLMI; HLMIF; HLMIFG; HLMIP; HLMIPQ; HR; HRG; HK; ABCDHL; ABCDHLM; ABCDHLMN; ABCDHLMNJ; ABCDHLMNJG; ABCDHLO; ABCDHLOJ; ABCDHLOJG; ABCDHLMI; ABCDHLMIF; ABCDHLMIFG; ABCDHLMIP; ABCDHLMIPQ; ABCDHR; ABCDHRG; ABCDHK; BCDHL; BCDHLM; BCDHLMN; BCDHLMNJ; BCDHLMNJG; BCDHLO; BCDHLOJ; BCDHLOJG; BCDHLMI; BCDHLMIF; BCDHLMIFG; BCDHLMIP; BCDHLMIPQ; BCDHR; BCDHRG; BCDHK; CDHL; CDHLM; CDHLMN; CDHLMNJ; CDHLMNJG; CDHLO; CDHLOJ; CDHLOJG; CDHLMI; CDHLMIF; CDHLMIFG; CDHLMIP; CDHLMIPQ; CDHR; CDHRG; CDHK; DHL; DHLM; DHLMN; DHLMNJ; DHLMNJG; DHLO; DHLOJ; DHLOJG; DHLMI; DHLMIF;

DHLMIFG; DHLMIP; DHLMIPQ; DHR; DHRG; DHK; M; and each combination of any one or more of E, H, and M with any one or more of steps of FIG. 2. In each of the embodiments of the above pathways where 3-buten-1-ol is produced from Step P it can be followed by Step S, conversion to crotyl alcohol. For example, BCDEPS; CDEPS; DEPS; HLMIPS; ABCDHLMIPS; BCDHLMIPS; CDHLMIPS and DHLMIPS.

Figure 3:
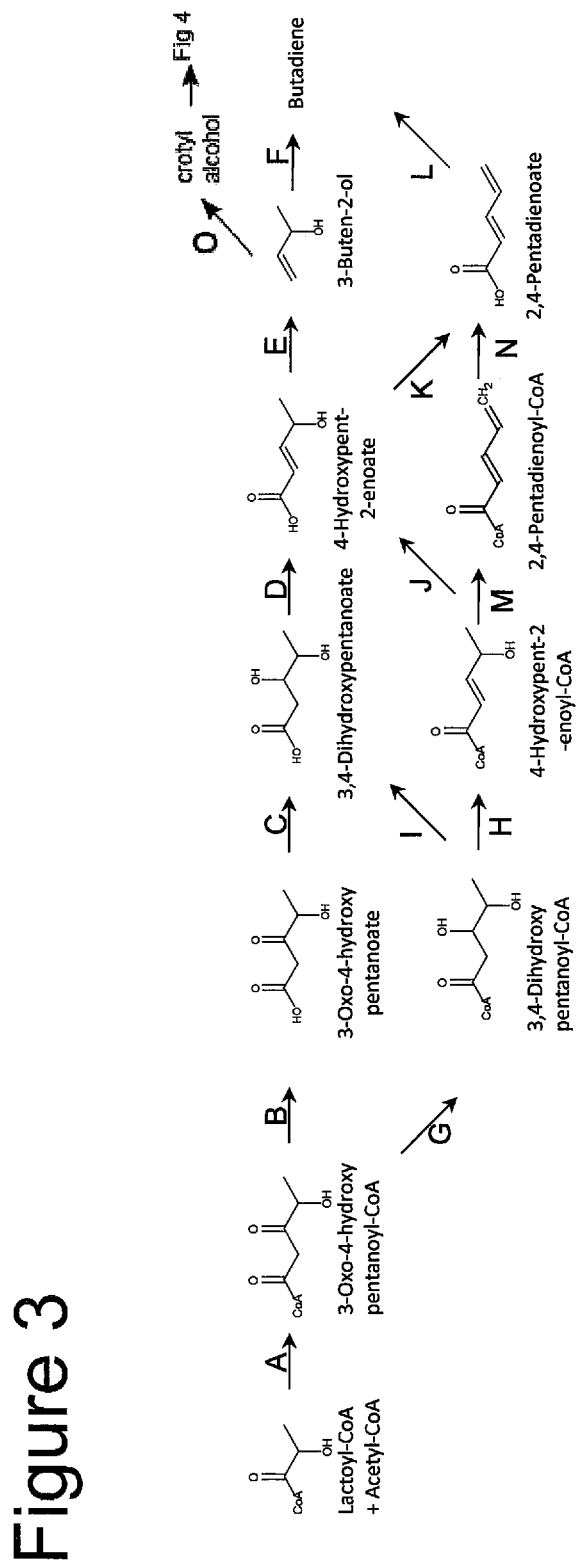
FIG. 3 shows pathways to but-3-enol and/or butadiene from lactoyl-CoA and acetyl-CoA. Enzymes are A. 3-Oxo-4-hydroxypentanoyl-CoA thiolase, B. 3-oxo-4-hydroxypentanoyl-CoA transferase, synthetase or hydrolase, C. 3-oxo-4-hydroxypentanoate reductase, D. 3,4-dihydroxypentanoate dehydratase, E. 4-hydroxypent-2-enoate decarboxylase, F. 3-buten-2-ol dehydratase, G. 3-oxo-4-hydroxypentanoyl-CoA reductase, H. 3,4-dihydroxypentanoyl-CoA dehydratase, I. 3,4-dihydroxypentanoyl-CoA transferase, synthetase or hydrolase, J. 4-hydroxypent-2-enoyl-CoA transferase, synthetase or hydrolase, K. 4-hydroxypent-2-enoate dehydratase, L. 2,4-pentadienoate decarboxylase, M. 4-hydroxypent-2-enoyl-CoA dehydratase, N. 2,4-pentadienoyl-CoA hydrolase, transferase or synthetase, O. vinylisomerase.

FIG. 3 provides exemplary pathways to butadiene from lactoyl-CoA and acetyl-CoA via intermediate 4-hydroxypent-2-enoate, 3-buten-2-ol, 4-hydroxypent-2-enoyl-CoA, 4-hydroxypent-2-enoate; enzymes such as 3,4-dihydroxypentanoate dehydratase (step D), 4-hydroxypent-2-enoate decarboxylase (step E), 3,4-dihydroxypentanoyl-CoA dehydratase (step H), and 4-hydroxypent-2-enoyl-CoA transferase (step J) can be used. 3-buten-2-ol from step E can be isolated as final product or converted to crotyl alcohol enzymatically (O) or chemically. Crotyl alcohol can be isolated or enter FIG. 4.

With reference to FIG. 3, the non-naturally occurring microbial organism can have any one of the following pathways: E; EF; D; DE; DEF; DK; DKL; J; JE; JEF; JK; JKL; H; HJ; HJE; HJEF; HJK; HJKL; HM; HMN; HMNL; GH; GHJ; GHJE; GHJEF; GHJK; GHJKL; GHM; GHMN; GHMNL; AGH; AGHJ; AGHJE; AGHJEF; AGHJK; AGHJKL; AGHM; AGHMN; AGHMNL; ID; IDE; IDEF; IDK; IDKL; GID; GIDE; GIDEF; GIDK; GIDKL; AGID; AGIDE; AGIDEF; AGIDK; AGIDKL; CD; CDE; CDEF; CDK; CDKL; BCD; BCDE; BCDEF; BCDK; BCDKL; ABCD; ABCDE; ABCDEF; ABCDK; ABCDKL; HJ; HJE; HJEF; HJK; HJKL; GHJ; GHJE; GHJEF; GHJK; GHJKL; AGHJ; AGHJE; AGHJEF; AGHJK; and AGHJKL; and each combination of any one or more of D, H, J and E with any one or more of steps of FIG. 3. In each of the embodiments of the above pathways where 3-buten-2-ol is produced it can be followed by Step O, conversion to crotyl alcohol. For example, EO; DEO; JEO; HJEO; AGHJEO; IDEO; GIDEO; AGIDEO; CDEO; BCDEO; ABCDEO; and GHJEO.

Figure 4:
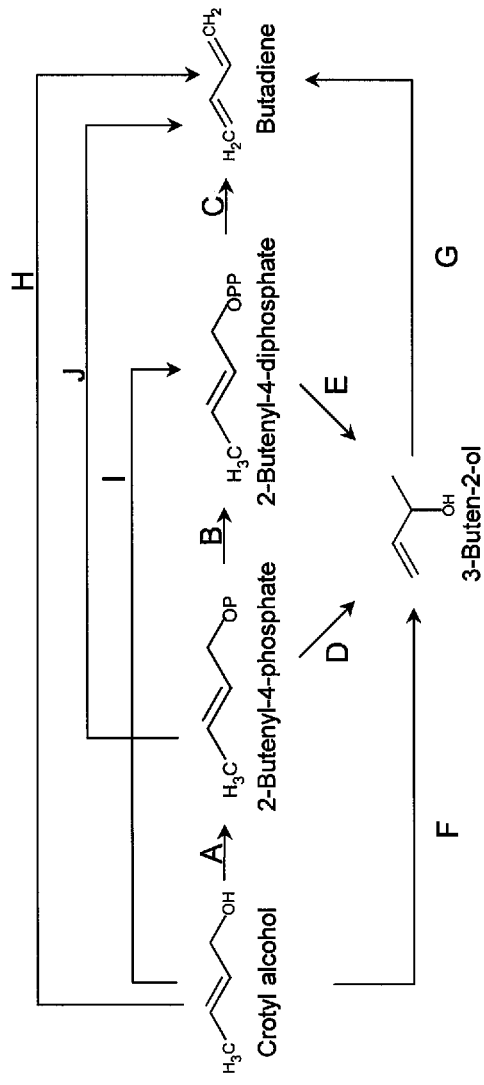
FIG. 4 shows pathways for converting crotyl alcohol (2-Buten-1-ol) to 3-buten-2-ol and/or butadiene. Enzymes are A. crotyl alcohol kinase, B. 2-butenyl-4-phosphate kinase, C. butadiene synthase, D. 3-buten-2-ol synthase, E. 3-buten-2-ol synthase, F. crotyl alcohol isomerase, G. 3-buten-2-ol dehydratase, H. crotyl alcohol dehydratase, I. crotyl alcohol diphosphokinase, J. butadiene synthase (from 2-butenyl-4-phosphate).

FIG. 4 provides exemplary pathways to butadiene from crotyl alcohol via one or more of the following intermediates: 2-butenyl-4-phosphate, 2-butenyl-4-diphosphate, and/or 3-buten-2-ol. Optionally, crotyl alcohol can be introduced into this pathway via any crotyl alcohol-producing pathway known in the art, or as described herein (e.g., from precursors crotyl aldehyde as converted to crotyl alcohol in the presence of crotyl aldehyde reductase (1J); or 2-hydroxypent-3-enoate converted to crotyl alcohol in the presence of 2-hydroxypent-3-enoate decarboxylase (1S) and including conversion from 3-buten-1-ol or 3-buten-2-ol). In some embodiments, the crotyl alcohol is produced by a pathway of FIG. 1, 2 or 3 and then introduced into a pathway of FIG. 4.

For example, step A of FIG. 4 uses a hydroxyethylthiazole kinase, a thiamine kinase, a pantothenate kinase, a 4-diphosphocytidyl-2-C-methyl-D-erythritol kinase, a riboflavin kinase, a L-fuculokinase, and/or a choline kinase, such as those described herein.

For example, step B of FIG. 4 subset of kinases of the EC 2.7.1.a class suitable for FIG. 4 Step B include 2.7.4.a Phosphokinases listed below. 2-Butenyl-4-phosphate kinase enzymes catalyze the transfer of a phosphate group to the phosphate group of 2-butenyl-4-phosphate (FIG. 4B).

With reference to FIG. 4, the non-naturally occurring microbial organism can have any one of the following pathways: D; DG; AD; ADG; E; EG; BE; BEG; ABE; ABEG; IE; IEG; F; FG; G; H; J; AJ; A; AB; ABC and each combination of any one or more of steps D, E, F with any one or more steps of FIG. 4, wherein when at least one of 4A, 4B, 4C, 4G or 4H is present then (i) at least one other unique step or pathway is present, such as step 4D, 4E, any unique step or pathway from FIG. 1 (e.g. 1D, 1E, 1F), or any one or more of Step 4A, 4B, 4C, 4G or 4H or (ii) at least one of A, B, C, G or H consists of a specific sub-group of enzyme classes or enzymes described herein as A for Step A, as B for Step B, as C for Step C, as G for Step G or as H for Step H.

In one embodiment for each pathway or step above is also contemplated the substitution of any one or more of subsets of enzymes described as Steps 1L, 1V, 1M, 2C, 2F, 2O, 2N, 2Q, 2R, 3F, 3K, 3M, 4A, 4B, 4C, 4G and 4H for its corresponding step (e.g. replace enzymes described for Step 1L with those described for Step 1L*).

With reference to FIGS. 1 and 4, or FIGS. 3 and 4, crotyl alcohol or 3-buten-2-ol is produced by a pathway of FIG. 1 (e.g., a pathway such as: ABCDJ; ABEIJ; ABEFS; BCDJ; BEIJ; BEFS; CDJ; EIJ; EFS; and DJ, optionally further with step W), or is produced by a pathway of FIG. 3, and then introduced into a pathway of FIG. 4 by combining with a pathway of FIG. 4 selected from: A; AB; ABC; AJ; AD; ADG; ABE; ABEG; F; FG; I; IC; IE; IEG; H; and G. In a further specifically contemplated embodiment is pathway having substitution of any one or more of subsets of enzymes described in Steps 4G and 4H for its corresponding step (e.g. FIG. 1 ABCDJ plus FIG. 4 IEG becomes FIG. 1 ABCDJ plus FIG. 4 IEG*).

With reference to FIGS. 2 and 4, crotyl alcohol or 3-buten-1-ol is produced by a pathway of FIG. 2 and then introduced into a pathway of FIG. 4 by combining with a pathway of FIG. 4 selected from: A; AB; ABC; AJ; AD; ADG; ABE; ABEG; F; FG; I; IC; IE; IEG; H; and G. In a further specifically contemplated embodiment is pathway having substitution of any one or more of subsets of enzymes described in Steps 4G and 4H for its corresponding step (e.g. FIG. 2 ABCDEPS plus FIG. 4 IEG becomes FIG. 2 ABCDEPS plus FIG. 4 IEG*).

Also specifically contemplated herein as unique transformations of FIG. 1 in addition to Step 1D and 1E are Steps 1N, 1O, 1P, 1R, 1F, 1U and 1K. Also specifically contemplated herein as unique transformations of FIG. 2 in addition to Step 2H and 2E is Step 2M. Also specifically contemplated herein as unique transformations of FIG. 4 in addition to Step 4D and 4E is Step 4F. In addition, Steps 1L, 1V, 1M, 2C, 2F, 2O, 2N, 2Q, 2R, 3F, 3K, 3M, 4A, 4B, 4C, 4G and 4H are unique. Accordingly, all subject matter specifically expressed herein applies equally to these additional unique steps. For example are embodiments of a non-naturally occurring microbial organism having a pathway to butadiene, crotyl alcohol, 2,4-pentadienoate, 3-buten-1-ol, 3-buten-2-ol, or other product said microbial organism comprising a nucleic acid encoding a pathway enzyme for the unique step, as well as methods of use described herein.

With reference to FIG. 4, a step A subset of kinases of FIG. 4 Step A include enzymes exemplified in the tables below for hydroxyethylthiazole kinase, thiamine kinase, pantothenate kinase, 4-diphosphocytidyl-2-C-methyl-D-erythritol kinase, riboflavin kinase, L-fuculokinase and choline kinase. The table below provides hydroxyethyl thiazole kinases, including EC 2.7.1.50 class, for FIG. 4, Step A:

| Protein | GenBank ID | GI Number | Organism |
| --- | --- | --- | --- |
| ThiM | YP_007535827.1 | 16080881 | *Bacillus subtilis* |
| Thi6 | CAA97929.1 | 1370444 | *Saccharomyces serevisiae* |
| ThiM | NP_372616.1 | 15925082 | *Staphylococcus aureus* |

-continued

| Protein | GenBank ID | GI Number | Organism |
|---|---|---|---|
| PH1157, thiM (analogue of thiK) | NP_143059.1 | 14590984 | Pyrococcus horikoshii OT3 |
| ThiM | Q830K4 | 81585041 | Enterococcus faecalis V583 |
| ThiM | YP_006701495 | 405760899 | Streptococcus pneumoniae SPNA45 |
| ThiM | YP_004888181 | 380031190 | Lactobacillus plantarum WCFS1 |
| ThiM | WP_012906431 | 502670591 | Citrobacter rodentium |
| ThiM | NP_61091 | 16765476 | Salmonella enterica subsp. Enterica LT2 |
| ThiM | YP_771477 | 116255644 | Rhizobium leguminosarum bv. viciae 3841 |
| ThiM (b2104) | AAC75165.1 | 1788421 | Escherichia coli str. K-12 substr. MG1655 |

Exemplary candidate thiamine kinases for FIG. 4, Step A are:

| Protein | GenBank ID | GI Number | Organism |
|---|---|---|---|
| thiK | AAC74190.1 | 1787349 | Escherichia coli K12 |
| thiK | NP_460178.1 | 16764563 | Salmonella enterica subsp. enterica serovar Typhimurium str. LT2 |

Exemplary fuculokinases for FIG. 4, Step A are:

| Protein | GenBank ID | GI Number | Organism |
|---|---|---|---|
| b2803 | AAC75845.1 | 1789168 | Escherichia coli K12 MG1655 |
| STM14_3591 | ACY90002.1 | 267995117 | Salmonella enterica subsp. enterica serovar Typhimurium str. 14028S |
| D186_16909 | EKS55716.1 | 411772069 | Citrobacter freundii ATCC 8090 = MTCC 1658 |

Exemplary 6-hydroxymethyl-7,8-dihydropterin pyrophosphokinase for FIG. 4, Step A are:

| Protein | GenBank ID | GI Number | Organism |
|---|---|---|---|
| folK | AAC73253.1 | 1786335 | Escherichia coli K12 |
| folK | NP_816865.1 | 29377711 | Enterococcus faecalis V583 |

Exemplary pantothenate kinases for FIG. 4, Step A are:

| Protein | GenBank ID | GI Number | Organism |
|---|---|---|---|
| CoaA | YP_006514461.1 | 397672926 | Mycobacterium tuberculosis H37Rv |
| CoaA | YP_491482.1 | 388479290 | Escherichia coli K12 |
| CoaX | Q9WZY5.1 | 81553296 | Thermotoga maritima MSB8 |
| Sav2130 | NP_372654.1 | 15925120 | Staphylococcus aureus subsp. aureus Mu50 |

Exemplary 4-(cytidine 5'-diphospho)-2-C-methyl-D-erythritol kinases (2.7.1.148) for FIG. 4, Step A are:

| Protein | GenBank ID | GI Number | Organism |
|---|---|---|---|
| ispE | NP_415726.1 | 16129171 | Escherichia coli K12 |
| ispE | KBJ36713.1 | 623367758 | Mycobacterium tuberculosis H37Rv |

Step A subset of synthases (alkene forming) for FIG. 4 Step C include 4-dimethylallyltryptophan synthase (class EC 2.5.1.34) and dimethylallyltranstransferase (class EC 2.5.1.1) that catalyze the conversion of 2-butenyl-4-diphosphate to 1,3-butadiene (Butadiene Synthase (BDS). The enzymes in these classes naturally possess such activity or can be engineered to exhibit or enhance this activity.

| Enzyme Commission Number | Enzyme Name |
|---|---|
| 2.5.1.34 | 4-dimethylallyltryptophan synthase |
| 2.5.1.1 | dimethylallyltranstransferase |

The enzyme-subsets designated as steps 1L, 1V, 1M, 2C, 2F, 2O, 2N, 2Q, 2R, 3F, 3K, 3M, 4G and 4H of dehydratase of the EC 4.2.1.a class for their respective Steps 1L, 1V, 1M, 2C, 2F, 2O, 2N, 2Q, 2R, 3F, 3K, 3M, 4G and 4H include the exemplary dehydratases of the 4.2.1.a class shown in the table below as well as a dehydratase class that dehydrates phenyllactyl-CoA to cinnamoyl-CoA exemplified by the dehydratase found in *Clostridium* sporogens that dehydrates phenyllactyl-CoA to cinnamoyl-CoA. This enzyme is composed of three subunits, one of which is a CoA transferase. The first step comprises of a CoA transfer from cinnamoyl-CoA to phenyllactate leading to the formation of phenyllactyl-CoA and cinnamate. The product cinnamate is released. The dehydratase then converts phenyllactyl-CoA into cinnamoyl-CoA. The FldA is the CoA transferase and FldBC are alpha and beta subunits of the dehydratase, which are realted to component D from *A. fermentans*.

| Gene | GenBank Accession No. | GI No. | Organism |
|---|---|---|---|
| hgdA | AAD31676.1 | 4883832 | Clostridium symbiosum |
| hgdB | AAD31677.1 | 4883833 | Clostridium symbiosum |
| hgdC | AAD31675.1 | 4883831 | Clostridium symbiosum |
| hgdA | EDK88042.1 | 148322792 | Fusobacterium nucleatum |
| hgdB | EDK88043.1 | 148322793 | Fusobacterium nucleatum |
| hgdC | EDK88041.1 | 148322791 | Fusobacterium nucleatum |
| FldB | Q93AL9.1 | 75406928 | Clostridium sporogens |
| FldC | Q93AL8.1 | 75406927 | Clostridium sporogens |

FIG. 4G and FIG. 4H subsets and FIG. 1 Step L, V and M subsets and FIG. 2 Step C, F, N, O, Q and R subsets, and FIG. 3 Steps F, K and M subsets are subsets of dehydratases for their respective Steps 1L, 1V, 1M, 2C, 2F, 2O, 2N, 2Q, 2R, 3F, 3K, 3M, 4G and 4H are listed in the following table.

| Protein | GenBank ID | GI Number | Organism |
|---|---|---|---|
| CGGC5_10771 | ELA28661.1 | 429853596 | Colletotrichum gloeosporioides Nara gc5 |
| UCRPA7_8726 | EON95759.1 | 500251895 | Togninia minima UCRPA7 |
| UCRNP2_8820 | EOD44468.1 | 485917493 | Neofusicoccum parvum UCRNP2 |

Further enzymes of FIG. 4G and FIG. 4H subsets and FIG. 1 Step L, V and M subsets and FIG. 2 Step C, F, N, O, Q and R subsets, and FIG. 3 Steps F, K and M subsets include dimethylmaleate hydratases that catalyze the dehydration of (2R,3S)-2,3-dimethylmalate into dimethylmaleate (EC 4.2.1.85) shown in the table below.

| Protein | GenBank ID | GI Number | Organism |
|---------|------------|-----------|----------|
| LeuC | 4KP1_A | 635576713 | *Methanococcus jannaschii* |
| phaJ1 | ABP99034.1 | 145967354 | *Pseudomonas putida* |

Enzymes with dehydratase and vinylisomerase activity suitable for FIG. 1 Steps G and M subsets and FIG. 4 Steps G and H subsets include bifunctional enzymes with dehydratase and isomerase activities exemplified below.

| Protein | GenBank ID | GI Number | Organism |
|---------|------------|-----------|----------|
| CGGC5_10771 | ELA28661.1 | 429853596 | *Colletotrichum gloeosporioides* Nara gc5 |
| UCRPA7_8726 | EON95759.1 | 500251895 | *Togninia minima* UCRPA7 |
| UCRNP2_8820 | EOD44468.1 | 485917493 | *Neofusicoccum parvum* UCRNP2 |

As used herein, the term "non-naturally occurring" when used in reference to a microbial organism or microorganism of the invention is intended to mean that the microbial organism has at least one genetic alteration not normally found in a naturally occurring strain of the referenced species, including wild-type strains of the referenced species. Genetic alterations include, for example, modifications introducing expressible nucleic acids encoding metabolic polypeptides, other nucleic acid additions, nucleic acid deletions and/or other functional disruption of the microbial organism's genetic material. Such modifications include, for example, coding regions and functional fragments thereof, for heterologous, homologous or both heterologous and homologous polypeptides for the referenced species. Additional modifications include, for example, non-coding regulatory regions in which the modifications alter expression of a gene or operon. Exemplary metabolic polypeptides include enzymes or proteins within a butadiene, crotyl alcohol, 3-buten-2-ol, 3-buten-1-ol, and/or 2,4-pentadienoate biosynthetic pathway.

A metabolic modification refers to a biochemical reaction that is altered from its naturally occurring state. Therefore, non-naturally occurring microorganisms can have genetic modifications to nucleic acids encoding metabolic polypeptides, or functional fragments thereof. Exemplary metabolic modifications are disclosed herein.

As used herein, the term "isolated" when used in reference to a microbial organism is intended to mean an organism that is substantially free of at least one component as the referenced microbial organism is found in nature. The term includes a microbial organism that is removed from some or all components as it is found in its natural environment. The term also includes a microbial organism that is removed from some or all components as the microbial organism is found in non-naturally occurring environments. Therefore, an isolated microbial organism is partly or completely separated from other substances as it is found in nature or as it is grown, stored or subsisted in non-naturally occurring environments. Specific examples of isolated microbial organisms include partially pure microbes, substantially pure microbes and microbes cultured in a medium that is non-naturally occurring.

As used herein, the terms "microbial," "microbial organism" or "microorganism" are intended to mean any organism that exists as a microscopic cell that is included within the domains of archaea, bacteria or eukarya. Therefore, the term is intended to encompass prokaryotic or eukaryotic cells or organisms having a microscopic size and includes bacteria, archaea and eubacteria of all species as well as eukaryotic microorganisms such as yeast and fungi. The term also includes cell cultures of any species that can be cultured for the production of a biochemical.

As used herein, the term "CoA" or "coenzyme A" is intended to mean an organic cofactor or prosthetic group (nonprotein portion of an enzyme) whose presence is required for the activity of many enzymes (the apoenzyme) to form an active enzyme system. Coenzyme A functions in certain condensing enzymes, acts in acetyl or other acyl group transfer and in fatty acid synthesis and oxidation, pyruvate oxidation and in other acetylation.

As used herein, the term "substantially anaerobic" when used in reference to a culture or growth condition is intended to mean that the amount of oxygen is less than about 10% of saturation for dissolved oxygen in liquid media. The term also is intended to include sealed chambers of liquid or solid medium maintained with an atmosphere of less than about 1% oxygen.

"Exogenous" as it is used herein is intended to mean that the referenced molecule or the referenced activity is introduced into the host microbial organism. The molecule can be introduced, for example, by introduction of an encoding nucleic acid into the host genetic material such as by integration into a host chromosome or as non-chromosomal genetic material such as a plasmid. Therefore, the term as it is used in reference to expression of an encoding nucleic acid refers to introduction of the encoding nucleic acid in an expressible form into the microbial organism. When used in reference to a biosynthetic activity, the term refers to an activity that is introduced into the host reference organism. The source can be, for example, a homologous or heterologous encoding nucleic acid that expresses the referenced activity following introduction into the host microbial organism. Therefore, the term "endogenous" refers to a referenced molecule or activity that is present in the host. Similarly, the term when used in reference to expression of an encoding nucleic acid refers to expression of an encoding nucleic acid contained within the microbial organism. The term "heterologous" refers to a molecule or activity derived from a source other than the referenced species whereas "homologous" refers to a molecule or activity derived from the host microbial organism. Accordingly, exogenous expression of an encoding nucleic acid of the invention can utilize either or both a heterologous or homologous encoding nucleic acid.

It is understood that when more than one exogenous nucleic acid is included in a microbial organism that the more than one exogenous nucleic acids refers to the referenced encoding nucleic acid or biosynthetic activity, as discussed above. It is further understood, as disclosed herein, that such more than one exogenous nucleic acids can be introduced into the host microbial organism on separate nucleic acid molecules, on polycistronic nucleic acid molecules, or a combination thereof, and still be considered as more than one exogenous nucleic acid. For example, as disclosed herein a microbial organism can be engineered to express two or more exogenous nucleic acids encoding a desired pathway enzyme or protein. In the case where two exogenous nucleic acids encoding a desired activity are introduced into a host microbial organism, it is understood that the two exogenous nucleic acids can be introduced as a single nucleic acid, for example, on a single plasmid, on separate plasmids, can be integrated into the host chromosome at a single site or multiple sites, and still be considered as two exogenous nucleic acids. Similarly, it is understood that more than two exogenous nucleic acids can be introduced into a host organism in any desired combination, for example, on a single plasmid, on separate plasmids, can be integrated into the host chromosome at a single site or multiple sites, and still be considered as two or more exogenous nucleic acids, for example three exogenous nucleic acids. Thus, the number of referenced exogenous nucleic acids or biosynthetic activities refers to the number of encoding nucleic acids or the number of biosynthetic activities, not the number of separate nucleic acids introduced into the host organism.

The non-naturally occurring microbal organisms of the invention can contain stable genetic alterations, which refers to microorganisms that can be cultured for greater than five generations without loss of the alteration. Generally, stable genetic alterations include modifications that persist greater than 10 generations, particularly stable modifications will persist more than about 25 generations, and more particularly, stable genetic modifications will be greater than 50 generations, including indefinitely.

Those skilled in the art will understand that the genetic alterations, including metabolic modifications exemplified herein, are described with reference to a suitable host organism such as *E. coli* and their corresponding metabolic reactions or a suitable source organism for desired genetic material such as genes for a desired metabolic pathway. However, given the complete genome sequencing of a wide variety of organisms and the high level of skill in the area of genomics, those skilled in the art will readily be able to apply the teachings and guidance provided herein to essentially all other organisms. For example, the *E. coli* metabolic alterations exemplified herein can readily be applied to other species by incorporating the same or analogous encoding nucleic acid from species other than the referenced species. Such genetic alterations include, for example, genetic alterations of species homologs, in general, and in particular, orthologs, paralogs or nonorthologous gene displacements.

An ortholog is a gene or genes that are related by vertical descent and are responsible for substantially the same or identical functions in different organisms. For example, mouse epoxide hydrolase and human epoxide hydrolase can be considered orthologs for the biological function of hydrolysis of epoxides. Genes are related by vertical descent when, for example, they share sequence similarity of sufficient amount to indicate they are homologous, or related by evolution from a common ancestor. Genes can also be considered orthologs if they share three-dimensional structure but not necessarily sequence similarity, of a sufficient amount to indicate that they have evolved from a common ancestor to the extent that the primary sequence similarity is not identifiable. Genes that are orthologous can encode proteins with sequence similarity of about 25% to 100% amino acid sequence identity. Genes encoding proteins sharing an amino acid similarity less that 25% can also be considered to have arisen by vertical descent if their three-dimensional structure also shows similarities.

Orthologs include genes or their encoded gene products that through, for example, evolution, have diverged in structure or overall activity. For example, where one species encodes a gene product exhibiting two functions and where such functions have been separated into distinct genes in a second species, the three genes and their corresponding products are considered to be orthologs. For the production of a biochemical product, those skilled in the art will understand that the orthologous gene harboring the metabolic activity to be introduced or disrupted is to be chosen for construction of the non-naturally occurring microorganism. An example of orthologs exhibiting separable activities is where distinct activities have been separated into distinct gene products between two or more species or within a single species.

In contrast, paralogs are homologs related by, for example, duplication followed by evolutionary divergence and have similar or common, but not identical functions. Paralogs can originate or derive from, for example, the same species or from a different species. For example, microsomal epoxide hydrolase (epoxide hydrolase I) and soluble epoxide hydrolase (epoxide hydrolase II) can be considered paralogs because they represent two distinct enzymes, co-evolved from a common ancestor, that catalyze distinct reactions and have distinct functions in the same species. Paralogs are proteins from the same species with significant sequence similarity to each other suggesting that they are homologous, or related through co-evolution from a common ancestor.

A nonorthologous gene displacement is a nonorthologous gene from one species that can substitute for a referenced gene function in a different species. Substitution includes, for example, being able to perform substantially the same or a similar function in the species of origin compared to the referenced function in the different species. Although generally, a nonorthologous gene displacement will be identifiable as structurally related to a known gene encoding the referenced function, less structurally related but functionally similar genes and their corresponding gene products nevertheless will still fall within the meaning of the term as it is used herein. Functional similarity requires, for example, at least some structural similarity in the active site or binding region of a nonorthologous gene product compared to a gene encoding the function sought to be substituted. Therefore, a nonorthologous gene includes, for example, a paralog or an unrelated gene.

Therefore, in identifying and constructing the non-naturally occurring microbial organisms of the invention having biosynthetic capability, those skilled in the art will understand with applying the teaching and guidance provided herein to a particular species that the identification of metabolic modifications can include identification and inclusion or inactivation of orthologs. To the extent that paralogs and/or nonorthologous gene displacements are present in the referenced microorganism that encode an enzyme catalyzing a similar or substantially similar metabolic reaction, those skilled in the art also can utilize these evolutionarily related genes.

Orthologs, paralogs and nonorthologous gene displacements can be determined by methods well known to those skilled in the art. For example, inspection of nucleic acid or amino acid sequences for two polypeptides will reveal sequence identity and similarities between the compared sequences. Based on such similarities, one skilled in the art can determine if the similarity is sufficiently high to indicate the proteins are related through evolution from a common ancestor. Algorithms well known to those skilled in the art, such as Align, BLAST, Clustal W and others compare and determine a raw sequence similarity or identity, and also determine the presence or significance of gaps in the sequence which can be assigned a weight or score. Such algorithms also are known in the art and are similarly applicable for determining nucleotide sequence similarity or identity. Parameters for sufficient similarity to determine relatedness are computed based on well known methods for calculating statistical similarity, or the chance of finding a similar match in a random polypeptide, and the significance of the match determined. A computer comparison of two or more sequences can, if desired, also be optimized visually by those skilled in the art. Related gene products or proteins can be expected to have a high similarity, for example, 25% to 100% sequence identity. Proteins that are unrelated can have an identity which is essentially the same as would be expected to occur by chance, if a database of sufficient size is scanned (about 5%). Sequences between 5% and 24% may or may not represent sufficient homology to conclude that the compared sequences are related. Additional statistical analysis to determine the significance of such matches given the size of the data set can be carried out to determine the relevance of these sequences.

Exemplary parameters for determining relatedness of two or more sequences using the BLAST algorithm, for example, can be as set forth below. Briefly, amino acid sequence alignments can be performed using BLASTP version 2.0.8 (Jan. 5, 1999) and the following parameters: Matrix: 0 BLOSUM62; gap open: 11; gap extension: 1; x_dropoff: 50; expect: 10.0; wordsize: 3; filter: on. Nucleic acid sequence alignments can be performed using BLASTN version 2.0.6 (Sep. 16, 1998) and the following parameters: Match: 1; mismatch: −2; gap open: 5; gap extension: 2; x_dropoff: 50; expect: 10.0; wordsize: 11; filter: off. Those skilled in the art will know what modifications can be made to the above parameters to either increase or decrease the stringency of the comparison, for example, and determine the relatedness of two or more sequences.

It is understood that any of the pathways disclosed herein, as described in the Examples and exemplified in the pathways of FIGS. 1-4, can be utilized to generate a non-naturally occurring microbial organism that produces any pathway intermediate or product, as desired. As disclosed herein, such a microbial organism that produces an intermediate can be used in combination with another microbial organism expressing downstream pathway enzymes to produce a desired product. However, it is understood that a non-naturally occurring microbial organism that produces a butadiene pathway intermediate can be utilized to produce the intermediate as a desired product.

This invention is also directed, in part to engineered biosynthetic pathways to improve carbon flux through a central metabolism intermediate en route to butadiene, crotyl alcohol, 3-buten-2-ol, 3-buten-1-ol, and/or 2,4-pentadienoate. The present invention provides non-naturally occurring microbial organisms having one or more exogenous genes encoding enzymes that can catalyze various enzymatic transformations en route to butadiene, crotyl alcohol, 3-buten-2-ol, 3-buten-1-ol, and/or 2,4-pentadienoate. In some embodiments, these enzymatic transformations are used to improve product yields, including but not limited to, from carbohydrate-based carbon feedstock.

The one or more exogenous genes encoding enzymes that can catalyze various enzymatic transformations en route to butadiene, crotyl alcohol, 3-buten-2-ol, 3-buten-1-ol, and/or 2,4-pentadienoate can be used in combination with genetic modifications that improve the amount of reducing equivalents available to the biosynthetic pathways, or that minimize loss of reducing equivalents and/or carbon to byproducts. In accordance with some embodiments, the one or more exogenous genes encoding enzymes that can catalyze various enzymatic transformations en route to butadiene, crotyl alcohol, 3-buten-2-ol, 3-buten-1-ol, and/or 2,4-pentadienoate can be used in combination with genetic modifications that (i) enhance carbon fixation, and/or (ii) accessing additional reducing equivalents from carbon sources.

Reducing equivalents can come in the form of NADH, NADPH, FADH, reduced quinones, reduced ferredoxins, reduced flavodoxins and thioredoxins.

It is understood by those skilled in the art that the pathways described herein for increasing product yield can be combined with any of the pathways disclosed herein, including those pathways depicted in the figures. One skilled in the art will understand that, depending on the pathway to a desired product and the precursors and intermediates of that pathway, a particular pathway for improving product yield, as discussed herein and in the examples, or combination of such pathways, can be used in combination with a pathway to a desired product to increase the yield of that product or a pathway intermediate.

The invention is described herein with general reference to the metabolic reaction, reactant or product thereof, or with specific reference to one or more nucleic acids or genes encoding an enzyme associated with or catalyzing, or a protein associated with, the referenced metabolic reaction, reactant or product. Unless otherwise expressly stated herein, those skilled in the art will understand that reference to a reaction also constitutes reference to the reactants and products of the reaction. Similarly, unless otherwise expressly stated herein, reference to a reactant or product also references the reaction, and reference to any of these metabolic constituents also references the gene or genes encoding the enzymes that catalyze or proteins involved in the referenced reaction, reactant or product. Likewise, given the well-known fields of metabolic biochemistry, enzymology and genomics, reference herein to a gene or encoding nucleic acid also constitutes a reference to the corresponding encoded enzyme and the reaction it catalyzes or a protein associated with the reaction as well as the reactants and products of the reaction.

The non-naturally occurring microbial organisms of the invention can be produced by introducing expressible nucleic acids encoding one or more of the enzymes or proteins participating in one or more butadiene, crotyl alcohol, 3-buten-2-ol, 3-buten-1-ol, and/or 2,4-pentadienoate biosynthetic pathways. Depending on the host microbial organism chosen for biosynthesis, nucleic acids for some or all of a particular butadiene, crotyl alcohol, 3-buten-2-ol, 3-buten-1-ol, and/or 2,4-pentadienoate acid biosynthetic pathway can be expressed. For example, if a chosen host is deficient in one or more enzymes or proteins for a desired biosynthetic pathway, then expressible nucleic acids for the deficient enzyme(s) or protein(s) are introduced into the host for subsequent exogenous expression. Alternatively, if the chosen host exhibits endogenous expression of some pathway genes, but is deficient in others, then an encoding nucleic acid is needed for the deficient enzyme(s) or protein(s) to achieve butadiene, crotyl alcohol, 3-buten-1-ol, 3-buten-2-ol, and/or 2,4-pentadienoate biosynthesis. Thus, a non-naturally occurring microbial organism of the invention can be produced by introducing exogenous enzyme or protein activities to obtain a desired biosynthetic pathway or a desired biosynthetic pathway can be obtained by introducing one or more exogenous enzyme or protein activities that, together with one or more endogenous enzymes or proteins, produces a desired product such as butadiene.

Host microbial organisms can be selected from, and the non-naturally occurring microbial organisms generated in, for example, bacteria, yeast, fungus or any of a variety of other microorganisms applicable to fermentation processes. Exemplary bacteria include species selected from *Escherichia coli, Klebsiella oxytoca, Anaerobiospirillum succiniciproducens, Actinobacillus succinogenes, Mannheimia succiniciproducens, Rhizobium etli, Bacillus subtilis, Corynebacterium glutamicum, Gluconobacter oxydans, Zymomonas mobilis, Lactococcus lactis, Lactobacillus plantarum, Streptomyces coelicolor, Clostridium acetobutylicum, Pseudomonas fluorescens,* and *Pseudomonas putida*. Exemplary yeasts or fungi include species selected from *Saccharomyces cerevisiae, Schizosaccharomyces pombe, Kluyveromyces lactis, Kluyveromyces marxianus, Aspergillus terreus, Aspergillus niger, Pichia pastoris, Rhizopus arrhizus, Rhizopus oryzae, Yarrowia lipolytica,* and the like. *E. coli* is a particularly useful host organism since it is a well characterized microbial organism suitable for genetic engineering. Other particularly useful host organisms include yeast such as *Saccharomyces cerevisiae*. It is understood that any suitable microbial host organism can be used to introduce metabolic and/or genetic modifications to produce a desired product.

Examplary *E. coli* host organisms include any non-pathogenic *E. coli* strain, including *E. coli* strains falling within taxonomic lineages such as A, B1, and B2. *E. coli* K-12 strains are in subgroup A. Host organisms include derivatives and variants of *E. coli* K-12, such as W3110 and MG1655. See, for example, Kuhnert, P., et at. (1995) Rapid and accurate identification of *Escherichia coli* K-12 strains. Applied and Environmental Microbiology 61:4135-4139; Bachmann, B. J. (1972) Pedigrees of some mutant strains of *Escherichia coli* K-12. *Bacteriol. Rev.* 36 525-57; and Bachmann, B. J. Derivations and genotypes of some mutant derivatives of *Escherichia coli* K-12. In: Neidhardt, F. C. et al. (1996) *Escherichia coli* and *Salmonella typhimurium*: Cellular and Molecular Biology (ASM Press, Washington, D.C.)

In some embodiments, a heterologous nucleic acid encoding a pathway enzyme of the disclosure can be described as obtained from an organism (such as a bacteria) that is other than the organisms of the host group. For example, the heterologous nucleic acid can be from a bacterial organism other than an organism selected from the group consisting of *E. coli, K. oxytoca, A. succiniciproducens*, etc.

In particularly useful embodiments, exogenous expression of the encoding nucleic acids is employed. Exogenous expression confers the ability to custom tailor the expression and/or regulatory elements to the host and application to achieve a desired expression level that is controlled by the user. However, endogenous expression also can be utilized in other embodiments such as by removing a negative regulatory effector or induction of the gene's promoter when linked to an inducible promoter or other regulatory element. Thus, an endogenous gene having a naturally occurring inducible promoter can be up-regulated by providing the appropriate inducing agent, or the regulatory region of an endogenous gene can be engineered to incorporate an inducible regulatory element, thereby allowing the regulation of increased expression of an endogenous gene at a desired time. Similarly, an inducible promoter can be included as a regulatory element for an exogenous gene introduced into a non-naturally occurring microbial organism.

Sources of encoding nucleic acids for a butadiene, crotyl alcohol, 3-buten-2-ol, 3-buten-1-ol and/or 2,4-pentadienoate pathway enzyme or protein can include, for example, any species where the encoded gene product is capable of catalyzing the referenced reaction. Such species include both prokaryotic and eukaryotic organisms including, but not limited to, bacteria, including archaea and eubacteria, and eukaryotes, including yeast, plant, insect, animal, and mammal, including human. Exemplary species for such sources include, for example, *Escherichia* species, including *Escherichia coli, Escherichia fergusonii, Methanocaldococcus jannaschii, Leptospira interrrogans, Geobacter sulfurreducens, Chloroflexus aurantiacus, Roseflexus* sp. RS-1, *Chloroflexus aggregans, Achromobacter xylosoxydans, Clostridia* species, including *Clostridium kluyveri, Clostridium symbiosum, Clostridium acetobutylicum, Clostridium saccharoperbutylacetonicum, Clostridium ljungdahlii, Trichomonas vaginalis* G3, *Trypanosoma brucei, Acidaminococcus fermentans, Fusobacterium* species, including *Fusobacterium nucleatum, Fusobacterium mortiferum, Corynebacterium glutamicum, Rattus norvegicus, Homo sapiens, Saccharomyces* species, including *Saccharomyces cerevisiae, Aspergillus* species, including *Aspergillus terreus, Aspergillus oryzae, Aspergillus niger, Gibberella zeae, Pichia stipitis, Mycobacterium* species, including *Mycobacterium smegmatis, Mycobacterium avium,* including subsp. *pratuberculosis, Salinispora arenicola, Pseudomonas* species, including *Pseudomonas* sp. CF600, *Pseudomonas putida, Pseudomonas fluorescens, Pseudomonas aeruginosa, Ralstonia* species, including *Ralstonia eutropha, Ralstonia eutropha* JMP134, *Ralstonia eutropha* H16, *Ralstonia pickettii, Lactobacillus plantarum, Klebsiella oxytoca, Bacillus* species, including *Bacillus subtilis, Bacillus pumilus, Bacillus megaterium, Pedicoccus pentosaceus, Chlorofexus* species, including *Chloroflexus aurantiacus, Chloroflexus aggregans, Rhodobacter sphaeroides, Methanocaldococcus jannaschii, Leptospira interrrogans, Candida maltosa, Salmonella* species, including *Salmonella enterica* serovar *Typhimurium, Shewanella* species, including *Shewanella oneidensis, Shewanella* sp. MR-4, *Alcaligenes faecalis, Geobacillus stearothermophilus, Serratia marcescens, Vibrio cholerae, Eubacterium barkeri, Bacteroides capillosus, Archaeoglobus fulgidus, Archaeoglobus fulgidus, Haloarcula marismortui, Pyrobaculum aerophilum* str. IM2, *Rhizobium* species, including *Rhizobium leguminosarum,* as well as other exemplary species disclosed herein or available as source organisms for corresponding genes. However, with the complete genome sequence available for now more than 550 species (with more than half of these available on public databases such as the NCBI), including 395 microorganism genomes and a variety of yeast, fungi, plant, and mammalian genomes, the identification of genes encoding the requisite butadiene, crotyl alcohol, 3-buten-2-ol, 3-buten-1-ol, and/or 2,4-pentadienoate biosynthetic activity for one or more genes in related or distant species, including for example, homologues, orthologs, paralogs and nonorthologous gene displacements of known genes, and the interchange of genetic alterations between organisms is routine and well known in the art. Accordingly, the metabolic alterations allowing biosynthesis of butadiene, crotyl alcohol, 3-buten-2-ol, 3-buten-1-ol, and/ or 2,4-pentadienoate described herein with reference to a particular organism such as *E. coli* can be readily applied to other microorganisms, including prokaryotic and eukaryotic organisms alike. Given the teachings and guidance provided herein, those skilled in the art will know that a metabolic alteration exemplified in one organism can be applied equally to other organisms.

In some instances, such as when an alternative butadiene, crotyl alcohol, 3-buten-2-ol, 3-buten-1-ol, and/or 2,4-pentadienoate biosynthetic pathway exists in an unrelated species butadiene, crotyl alcohol, 3-buten-2-ol, 3-buten-1-ol, and/or 2,4-pentadienoate biosynthesis can be conferred onto the host species by, for example, exogenous expression of a paralog or paralogs from the unrelated species that catalyzes a similar, yet non-identical metabolic reaction to replace the referenced reaction. Because certain differences among metabolic networks exist between different organisms, those skilled in the art will understand that the actual gene usage between different organisms may differ. However, given the teachings and guidance provided herein, those skilled in the art also will understand that the teachings and methods of the invention can be applied to all microbial organisms using the cognate metabolic alterations to those exemplified herein to construct a microbial organism in a species of interest that will synthesize butadiene, crotyl alcohol, 3-buten-2-ol, 3-buten-1-ol and/or 2,4-pentadienoate.

Methods for constructing and testing the expression levels of a non-naturally occurring butadiene, crotyl alcohol, 3-buten-2-ol, 3-buten-1-ol and/or 2,4-pentadienoate-producing host can be performed, for example, by recombinant and detection methods well known in the art. Such methods can be found described in, for example, Sambrook et al., *Molecular Cloning: A Laboratory Manual*, Third Ed., Cold Spring Harbor Laboratory, New York (2001); and Ausubel et al., *Current Protocols in Molecular Biology*, John Wiley and Sons, Baltimore, Md. (1999).

Exogenous nucleic acid sequences involved in a pathway for production of butadiene, crotyl alcohol, 3-buten-2-ol, 3-buten-1-ol and/or 2,4-pentadienoate can be introduced stably or transiently into a host cell using techniques well known in the art including, but not limited to, conjugation, electroporation, chemical transformation, transduction, transfection, and ultrasound transformation. For exogenous expression in *E. coli* or other prokaryotic cells, some nucleic acid sequences in the genes or cDNAs of eukaryotic nucleic acids can encode targeting signals such as an N-terminal mitochondrial or other targeting signal, which can be removed before transformation into prokaryotic host cells, if desired. For example, removal of a mitochondrial leader sequence led to increased expression in *E. coli* (Hoffmeister et al., *J. Biol. Chem.* 280:4329-4338 (2005)). For exogenous expression in yeast or other eukaryotic cells, genes can be expressed in the cytosol without the addition of leader sequence, or can be targeted to mitochondrion or other organelles, or targeted for secretion, by the addition of a suitable targeting sequence such as a mitochondrial targeting or secretion signal suitable for the host cells. Thus, it is understood that appropriate modifications to a nucleic acid sequence to remove or include a targeting sequence can be incorporated into an exogenous nucleic acid sequence to impart desirable properties. Furthermore, genes can be subjected to codon optimization with techniques well known in the art to achieve optimized expression of the proteins.

An expression vector or vectors can be constructed to include one or more butadiene, crotyl alcohol, 3-buten-2-ol, 3-buten-1-ol, and/or 2,4-pentadienoate biosynthetic pathway encoding nucleic acids as exemplified herein operably linked to expression control sequences functional in the host organism. Expression vectors applicable for use in the microbial host organisms of the invention include, for example, plasmids, phage vectors, viral vectors, episomes and artificial chromosomes, including vectors and selection sequences or markers operable for stable integration into a host chromosome. Additionally, the expression vectors can include one or more selectable marker genes and appropriate expression control sequences. Selectable marker genes also can be included that, for example, provide resistance to antibiotics or toxins, complement auxotrophic deficiencies, or supply critical nutrients not in the culture media. Expression control sequences can include constitutive and inducible promoters, transcription enhancers, transcription terminators, and the like which are well known in the art. When two or more exogenous encoding nucleic acids are to be co-expressed, both nucleic acids can be inserted, for example, into a single expression vector or in separate expression vectors. For single vector expression, the encoding nucleic acids can be operationally linked to one common expression control sequence or linked to different expression control sequences, such as one inducible promoter and one constitutive promoter. The transformation of exogenous nucleic acid sequences involved in a metabolic or synthetic pathway can be confirmed using methods well known in the art. Such methods include, for example, nucleic acid analysis such as Northern blots or polymerase chain reaction (PCR) amplification of mRNA, or immunoblotting for expression of gene products, or other suitable analytical methods to test the expression of an introduced nucleic acid sequence or its corresponding gene product. It is understood by those skilled in the art that the exogenous nucleic acid is expressed in a sufficient amount to produce the desired product, and it is further understood that expression levels can be optimized to obtain sufficient expression using methods well known in the art and as disclosed herein.

The invention additionally provides methods of producing butadiene, crotyl alcohol, 3-buten-2-ol, 3-buten-1-ol, and/or 2,4-pentadienoate using the microbial organisms of the invention comprising one or more pathway gene(s). In a particular embodiment, the invention provides a method for producing a target compound by culturing a non-naturally occurring microbial organism, comprising a microbial organism having a butadiene, crotyl alcohol, 3-buten-2-ol, 3-buten-1-ol, and/or 2,4-pentadienoate pathway comprising at least one exogenous nucleic acid encoding a pathway enzyme expressed in a sufficient amount to produce butadiene, crotyl alcohol, 3-buten-2-ol, 3-buten-1-ol, and/or 2,4-pentadienoate, under conditions and for a sufficient period of time.

Suitable purification and/or assays to test for the production of producing butadiene, crotyl alcohol, 3-buten-2-ol, 3-buten-1-ol, and/or 2,4-pentadienoate can be performed using well known methods. Suitable replicates such as triplicate cultures can be grown for each engineered strain to be tested. For example, product and byproduct formation in the engineered production host can be monitored. The final product and intermediates, and other organic compounds, can be analyzed by methods such as HPLC (High Performance Liquid Chromatography), GC-MS (Gas Chromatography-Mass Spectroscopy) and LC-MS (Liquid Chromatography-Mass Spectroscopy) or other suitable analytical methods using routine procedures well known in the art. The release of product in the fermentation broth can also be tested with the culture supernatant. Byproducts and residual glucose can be quantified by HPLC using, for example, a refractive index detector for glucose and alcohols, and a UV detector for organic acids (Lin et al., *Biotechnol. Bioeng.* 90:775-779 (2005)), or other suitable assay and detection methods well known in the art. The individual enzyme or protein activities from the exogenous DNA sequences can also be assayed using methods well known in the art.

The butadiene, crotyl alcohol, 3-buten-2-ol, 3-buten-1-ol, and/or 2,4-pentadienoate can be separated from other components in the culture using a variety of methods well known in the art. Such separation methods include, for example, extraction procedures as well as methods that include continuous liquid-liquid extraction, pervaporation, membrane filtration, membrane separation, reverse osmosis, electrodialysis, distillation, crystallization, centrifugation, extractive filtration, ion exchange chromatography, size exclusion chromatography, adsorption chromatography, and ultrafiltration. All of the above methods are well known in the art.

Any of the non-naturally occurring microbial organisms described herein can be cultured to produce and/or secrete the biosynthetic products of the invention. For example, the butadiene, crotyl alcohol, 3-buten-2-ol, 3-buten-1-ol, and/or 2,4-pentadienoate producers can be cultured for the biosynthetic production of butadiene, crotyl alcohol, 3-buten-2-ol, 3-buten-1-ol, and/or 2,4-pentadienoate.

For the production of butadiene, crotyl alcohol, 3-buten-2-ol, 3-buten-1-ol, and/or 2,4-pentadienoate, the recombinant strains are cultured in a medium with carbon source and other essential nutrients. It is sometimes desirable and can be highly desirable to maintain anaerobic conditions in the fermenter to reduce the cost of the overall process. Such conditions can be obtained, for example, by first sparging the medium with nitrogen and then sealing the flasks with a septum and crimp-cap. For strains where growth is not observed anaerobically, microaerobic or substantially anaerobic conditions can be applied by perforating the septum with a small hole for limited aeration. Exemplary anaerobic conditions have been described previously and are well-known in the art. Exemplary aerobic and anaerobic conditions are described, for example, in United State publication 2009/0047719, filed Aug. 10, 2007. Fermentations can be performed in a batch, fed-batch or continuous manner, as disclosed herein.

If desired, the pH of the medium can be maintained at a desired pH, in particular neutral pH, such as a pH of around 7 by addition of a base, such as NaOH or other bases, or acid, as needed to maintain the culture medium at a desirable pH. The growth rate can be determined by measuring optical density using a spectrophotometer (600 nm), and the glucose uptake rate by monitoring carbon source depletion over time.

The growth medium can include, for example, any carbohydrate source which can supply a source of carbon to the non-naturally occurring microorganism. Such sources include, for example, sugars such as glucose, xylose, arabinose, galactose, mannose, fructose, sucrose and starch. Other sources of carbohydrate include, for example, renewable feedstocks and biomass. Exemplary types of biomasses that can be used as feedstocks in the methods of the invention include cellulosic biomass, hemicellulosic biomass and lignin feedstocks or portions of feedstocks. Such biomass feedstocks contain, for example, carbohydrate substrates useful as carbon sources such as glucose, xylose, arabinose, galactose, mannose, fructose and starch. Other non-carbohydrate feedstocks include alcohols such as methanol, ethanol and glycerol and gaseous carbon substrates such as methane and syngas. Given the teachings and guidance provided herein, those skilled in the art will understand that renewable feedstocks and biomass other than those exemplified above also can be used for culturing the microbial organisms of the invention for the production of butadiene, crotyl alcohol, 3-buten-2-ol, 3-buten-1-ol, and/or 2,4-pentadienoate.

In some embodiments, culture conditions include anaerobic or substantially anaerobic growth or maintenance conditions. Exemplary anaerobic conditions have been described previously and are well known in the art. Exemplary anaerobic conditions for fermentation processes are described herein and are described, for example, in U.S. publication 2009/0047719, filed Aug. 10, 2007. Any of these conditions can be employed with the non-naturally occurring microbial organisms as well as other anaerobic conditions well known in the art. Under such anaerobic or substantially anaerobic conditions, butadiene, crotyl alcohol, 3-buten-2-ol, 3-buten-1-ol, and/or 2,4-pentadienoate producers can synthesize butadiene, crotyl alcohol, 3-buten-1-ol, 3-buten-2-ol, and/or 2,4-pentadienoate at intracellular concentrations of 5-10 mM or more as well as all other concentrations exemplified herein. It is understood that, even though the above description refers to intracellular concentrations, butadiene, crotyl alcohol, 3-buten-2-ol, 3-buten-1-ol, and/or 2,4-pentadienoate producing microbial organisms can butadiene, crotyl alcohol, 3-buten-2-ol, 3-buten-1-ol, and/or 2,4-pentadienoate intracellularly and/or secrete the product into the culture medium.

In addition to the culturing and fermentation conditions disclosed herein, growth condition for achieving biosynthesis of butadiene, crotyl alcohol, 3-buten-2-ol, 3-buten-1-ol, and/or 2,4-pentadienoate can include the addition of an osmoprotectant to the culturing conditions. In certain embodiments, the non-naturally occurring microbial organisms of the invention can be sustained, cultured or fermented as described herein in the presence of an osmoprotectant. Briefly, an osmoprotectant refers to a compound that acts as an osmolyte and helps a microbial organism as described herein survive osmotic stress. Osmoprotectants include, but are not limited to, betaines, amino acids, and the sugar trehalose. Non-limiting examples of such are glycine betaine, proline betaine, dimethylthetin, dimethylsulfoniopropionate, 3-dimethylsulfonio-2-methylpropionate, pipecolic acid, dimethylsulfonioacetate, choline, L-carnitine and ectoine. In one aspect, the osmoprotectant is glycine betaine.

In some embodiments, the carbon feedstock and other cellular uptake sources such as phosphate, ammonia, sulfate, chloride and other halogens can be chosen to alter the isotopic distribution of the atoms present in butadiene, crotyl alcohol, 3-buten-2-ol, 3-buten-1-ol, and/or 2,4-pentadienoate or any pathway intermediate. The various carbon feedstock and other uptake sources enumerated above will be referred to herein, collectively, as "uptake sources."

As used herein, the term "bioderived" means derived from or synthesized by a biological organism and can be considered a renewable resource since it can be generated by a biological organism. Such a biological organism, in particular the microbial organisms of the invention disclosed herein, can utilize feedstock or biomass, such as, sugars or carbohydrates obtained from an agricultural, plant, bacterial, or animal source. Alternatively, the biological organism can utilize atmospheric carbon. As used herein, the term "biobased" means a product as described above that is composed, in whole or in part, of a bioderived compound of the invention. A biobased or bioderived product is in contrast to a petroleum derived product, wherein such a product is derived from or synthesized from petroleum or a petrochemical feedstock.

The culture conditions can include, for example, liquid culture procedures as well as fermentation and other large scale culture procedures. As described herein, particularly useful yields of the biosynthetic products of the invention can be obtained under anaerobic or substantially anaerobic culture conditions.

As described herein, one exemplary growth condition for achieving biosynthesis of butadiene, crotyl alcohol, 3-buten-2-ol, 3-buten-1-ol, and/or 2,4-pentadienoate includes anaerobic culture or fermentation conditions. In certain embodiments, the non-naturally occurring microbial organisms of the invention can be sustained, cultured or fermented under anaerobic or substantially anaerobic conditions. Anaerobic conditions refer to an environment devoid of oxygen.

The culture conditions described herein can be scaled up and grown continuously for manufacturing of butadiene, crotyl alcohol, 3-buten-2-ol, 3-buten-1-ol, and/or 2,4-pentadienoate. Exemplary growth procedures include, for example, fed-batch fermentation and batch separation; fed-batch fermentation and continuous separation, or continuous fermentation and continuous separation.

Example 1. Enzyme Candidates for FIG. 1-3

Several pathways are shown in FIGS. 1-2 for converting pyruvate and acetaldehyde to butadiene and butadiene precursors. Acetaldehyde is formed via reduction of acetyl-CoA by acetyl-CoA reductase, also called acetaldehyde dehydrogenase (Step 1A and 2A). Pyruvate and acetaldehyde are condensed to 4-hydroxy-2-oxovalerate by 4-hydroxy-2-ketovalerate aldolase (Step 1B and 2B). Alternately, the acetaldehyde intermediate can be formed by other enzymes or metabolic pathways known in the art, such as pyruvate decarboxylase. In a particularly preferred embodiment, Steps A and B of FIGS. 1 and 2 are catalyzed by a bifunctional enzyme with aldolase and dehydrogenase activities.

In FIG. 1, the 4-hydroxy-2-oxovalerate product is subsequently dehydrated to 2-oxopent-3-enoate (Step 1E). Reduction of 2-oxopent-3-enoate to its corresponding hydroxyacid (Step 1F) is catalyzed by a secondary alcohol dehydrogenase. Isomerization of 2-hydroxypent-3-enoate to 4-hydroxypent-2-enoate (1U), followed by dehydration (1V) yields 2,4-pentadienoate. These two reactions can be catalyzed by two different enzymes (1U, 1V) or by a bifunctional isomerase/dehydratase (1G). Decarboxylation of 2,4-pentadienoate to butadiene is catalyzed by a pentadienoate decarboxylase (1H). Alternately, the conversion of the 2-oxopent-3-enoate or 2-hydroxypent-3-enoate intermediates to 2,4-pentadienoate proceeds via acyl-CoA intermediates (Steps 1N, 1O, 1P, 1Q, 1R). The conversion of an acid to an acyl-CoA is catalyzed by CoA transferases and CoA synthetases. Acyl-CoA to acid conversion is catalyzed by CoA synthetases, transferases or hydrolases. In yet another alternate pathway, decarboxylation of 4-hydroxy-2-oxovalerate by a keto-acid decarboxylase yields 3-hydroxybutyraldehyde (1C). This intermediate can be dehydrated to crotyl aldehyde by a dehydratase and subsequently reduced to crotyl alcohol (1J). Crotyl alcohol can be isolated as a useful product or optionally be further converted to butadiene by one or more enzymes with dehydratase and vinylisomerase activities (1K, 1L, 1M). Additional alternative routes from the 2-oxopent-3-enoate, 2-hydroxypent-3-enoate or 4-hydroxypent-2-enoate intermediates to butadiene shown in FIG. 1 take advantage of enzymes in the decarboxylase class (EC 4.1.1.-; Steps 1C, 1I, 1S, 1T). In addition to butadiene, useful products described herein include crotyl alcohol, 3-buten-2-ol, 3-hydroxybutyrate (resulting from oxidation of 3-hydroxybutyraldehyde), crotonate (oxidation of crotyl aldehyde), 4-hydroxy-2-oxovalerate, 2-oxopent-3-enoate, 2-hydroxypent-3-enoate, 4-hydroxypent-2-enoate and pentadienoate. Enzymes for catalyzing each step are described below.

FIG. 2 also shows pathways derived from the 4-hydroxy 2-oxovalerate intermediate. 4-hydroxy 2-oxovalerate is dehydrated to 2-oxopent-4-enoate (also called 2-hydroxypenta-2,4-dienoate) by 4-hydroxy-2-oxopentanoate dehydratase, also called 2-oxopent-4-enoate hydratase (2C). An alcohol dehydrogenase with 2-oxopent-4-enoate reductase activity forms 2-hydroxypent-4-enoate. Multiple enzymatic routes are shown in FIG. 2 for converting 2-hydroxypent-4-enoate to butadiene and butadiene precursors. One route entails isomerization of 2-hydroxypent-4-enoate to 5-hydroxypent-2-enoate (2E). This intermediate is then decarboxylated to 3-buten-1-ol (2P) and dehydrated to butadiene (2Q). Alternately, the 5-hydroxypent-2-enoate is further dehydrated to pentadienoate (2F) and subsequently decarboxylated to butadiene (2G). In yet another pathway, the 5-hydroxypent-2-enoate intermediate is activated to its corresponding acyl-CoA (2I), dehydrated to pentadienoyl-CoA (2N), and further hydrolyzed to 2,4-pentadienoate (2J). Yet another set of pathways results when 2-hydroxypent-4-enoate is converted to 3-hydroxypent-4-enoate (abbreviated as 3HPE) by a mutase (2H). Direct conversion of 3HPE to butadiene is catalyzed by an oxidative decarboxylase (2K). The two-step conversion of 3HPE to butadiene via 2,4-pentadienoate entails dehydration (2R) followed by decarboxylation (2G). In yet another route, 3HPE is activated to its acyl-CoA by a CoA synthetase or transferase. Conversion of 3-HPE-CoA to 2,4-pentadienoyl-CoA is catalyzed by an acyl-CoA dehydratase (2O) or an isomerase and dehydratase (2M, 2N). Useful products shown in FIG. 2 include butadiene, 3-buten-1-ol, 4-hydroxy-2-oxovalerate, 2-oxopent-4-enoate, 2-hydroxypent-4-enoate, 4-hydroxypent-2-enoate, 3HPE and 2,4-pentadienoate. Enzymes for catalyzing each step are described below.

Pathways converting lactoyl-CoA to 4-hydroxypent-2-enoate, and further to 3-buten-2-ol and butadiene, are shown in FIG. 3. The conversion of lactoyl-CoA to 4-hydroxypent-2-enoate is accomplished in four or more enzymatic steps shown in FIG. 3. Lactoyl-CoA and acetyl-CoA are first condensed to 3-oxo-4-hydroxypentanoyl-CoA by 3-oxo-4-hydroxypentanoyl-CoA thiolase, a beta-ketothiolase (Step 3A). In one pathway, the 3-oxo-4-hydroxypentanoyl-CoA intermediate is converted to its corresponding acid by a CoA hydrolase, transferase or synthetase (3B). Reduction of the 3-oxo ketone by an alcohol dehydrogenase yields 3,4-dihydroxypentanoate (3C). Dehydration of the dihydroxyacid yields 4-hydroxypent-2-enoate (3D). 4-Hydroxypent-2-enoate decarboxylase converts 4-hydroxypent-2-enoate to 3-buten-2-ol (3E). Isomerization of 3-buten-2-ol to butadiene is catalyzed by a vinylisomerase (3F). Decarboxylation and dehydration of 4-hydroxypent-2-enoate to butadiene can instead proceed with dehydration first (3K) followed by decarboxylation of 2,4-pentadienoate (3L). Further alternate pathways shown in FIG. 3 entail reduction of the 3-oxo-4-hydroxypentanoyl-CoA to its 3-hydroxyacyl-CoA (3G), and optional dehydration of the 3-hydroxyacyl-CoA to 4-hydroxypent-2-enoyl-CoA (3H). Conversion of the acyl-CoA intermediates to their corresponding acids by CoA hydrolases, synthases and transferases is shown in steps 3I and 3J. Useful products shown in FIG. 3 include butadiene, 3-buten-2-ol, 3-oxo-4-hydroxypentanoate, 3,4-dihydroxypentanoate and 4-hydroxypentenoate. Enzymes and gene candidates for catalyzing but-3-en-2-ol and butadiene pathway reactions are described in further detail below FIG. 4 shows enzymatic pathways for converting CrotOH to butadiene. In one pathway, CrotOH is phosphorylated to 2-butenyl-4-phosphate by a CrotOH kinase (Step A). The 2-butenyl-4-phosphate intermediate is again phosphorylated to 2-butenyl-4-diphosphate (Step B). A butadiene synthase (BDS) enzyme catalyzes the conversion of 2-butenyl-4-diphosphate to butadiene (Step C). Such a BDS can be derived from a phosphate lyase enzyme such as isoprene synthase using methods, such as directed evolution, as described herein. In an alternate pathway, CrotOH is directly converted to 2-butenyl-4-diphosphate by a diphosphokinase (step I). In yet another alternative pathway, CrotOH can be converted to butadiene by a CrotOH dehydratase or a bifunctional dehydratase/isomerase (step H). In yet another pathway, the 2-butenyl-4-phosphate intermediate is directly converted to butadiene by a BDS (monophosphate) (step J). Further are shown pathways that proceed through a 3-buten-2-ol (MVC) intermediate. Crotyl alcohol is isomerized to MVC by an enzyme with vinylisomerase activity (step F). 3-Buten-2-ol synthase enzymes catalyze the conversion of 2-butenyl-4-phosphate or 2-butenyl-4-diphosphate to 3-buten-2-ol (Steps 4D and 4E, respectively). The 3-buten-2-ol intermediate is then dehydrated to butadiene (4G).

| EC | Description | Step |
|---|---|---|
| 1.1.1.a | Alcohol dehydrogenase | 1F, 1J, 1O, 2D, 3C, 3G |
| 1.2.1.b | Acyl-CoA reductase (aldehyde forming) | 1A, 2A |
| 2.3.1.a | Thiolase | 3A |
| 2.7.1.a | Kinase | 4A |
| 2.7.4.a | Phosphokinase | 4B |
| 2.7.6.a | Diphosphokinase | 4I |
| 2.8.3.a | CoA transferase | 1N, 1R, 1Q, 2I, 2J, 2L, 3B, 3I, 3J, 3N |
| 3.2.1.a | CoA hydrolase | 1Q, 2J, 2I, 3B, 3I, 3J, 3N |
| 4.1.1.a | Decarboxylase | 1C, 1H, 1I, 1S, 1T, 2G, 2P, 3E, 3L |
| 4.1.1.b | Decarboxylase (alkene forming) | 2K |
| 4.1.2.a | Aldolase | 1B, 2B |
| 4.2.1.a | Dehydratase | 1D, 1E, 1L, 1P, 1V, 1M 2C, 2F, 2O, 2N, 2Q, 2R, 3D, 3F, 3H, 3K, 3M, 4G, 4H |
| 4.2.1.c | Dehydratase/vinylisomerase | 1G, 1M, 4H |
| 4.2.3.a | Synthase (alkene-forming) | 4C |
| 5.3.3 | Isomerase | 1K, 1U, 2M, 1W, 2S, 3O |
| 6.2.1.a | CoA synthetase | 1N, 1R, 1Q, 2I, 2J, 2L, 3B, 3I, 3J, 3N |
| 5.4.4 | Alcohol mutase | 2H, 2E |
|  | Alkenol Synthases | 4D, 4E |

1.1.1.a Alcohol Dehydrogenase

The enzyme activities required for the reactions shown in FIGS. 1-4 are listed in the table and described in further detail below. The reduction of 2-oxopent-3-enoate, 2-oxopent-4-enoate to corresponding 2-hydroxyacids (1F, 2D) are catalyzed by secondary alcohol dehydrogenases with 2-ketoacid reductase activity. Exemplary secondary alcohol dehydrogenases include malate dehydrogenase, lactate dehydrogenase, 2-ketoadipate reductase, isopropanol dehydrogenase, methyl ethyl ketone reductase, and others described below and known in the art. Two secondary alcohol dehydrogenase enzymes from *E. coli* are encoded by malate dehydrogenase (mdh: EC 1.1.1.37, 1.1.1.82, 1.1.1.299) and lactate dehydrogenase (ldhA). *S. cerevisiae* encodes three copies of malate dehydrogenase, MDH1 (McAlister-Henn and Thompson, *J. Bacteriol.* 169:5157-5166 (1987), MDH2 (Minard and McAlister-Henn, *Mol. Cell. Biol.* 11:370-380 (1991); Gibson and McAlister-Henn, *J. Biol. Chem.* 278:25628-25636 (2003)), and MDH3 (Steffan and McAlister-Henn, *J. Biol. Chem.* 267:24708-24715 (1992)), which localize to the mitochondrion, cytosol, and peroxisome, respectively. Close homologs to the cytosolic malate dehydrogenase, MDH2, from *S. cerevisiae* are found in several organisms including *Kluyveromyces lactis* and *Candida tropicalis*. The lactate dehydrogenase from *Ralstonia eutropha* has been shown to demonstrate high activities on 2-ketoacids of various chain lengths including lactate, 2-oxobutyrate, 2-oxopentanoate and 2-oxoglutarate (Steinbuchel et al., *Eur. J. Biochem.* 130:329-334 (1983)). Conversion of alpha-ketoadipate into alpha-hydroxyadipate can be catalyzed by 2-ketoadipate reductase, an enzyme reported to be found in rat and in human placenta (Suda et al., *Arch. Biochem. Biophys.* 176:610-620 (1976); Suda et al., *Biochem. Biophys. Res. Commun.* 77:586-591 (1977)). Alcohol dehydrogenase enzymes of *C. beijerinckii* (Ismaiel et al., *J. Bacteriol.* 175:5097-5105 (1993)) and *T. brockii* (Lamed et al., *Biochem. J.* 195:183-190 (1981); Peretz et al., *Biochemistry.* 28:6549-6555 (1989)) convert acetone to isopropanol. Methyl ethyl ketone reductase catalyzes the reduction of MEK to 2-butanol. Exemplary MEK reductase enzymes can be found in *Rhodococcus ruber* (Kosjek et al., *Biotechnol Bioeng.* 86:55-62 (2004)) and *Pyrococcus furiosus* (van der Oost et al., *Eur. J. Biochem.* 268:3062-3068 (2001)). The cloning of the bdhA gene from *Rhizobium* (*Sinorhizobium*) *meliloti* into *E. coli* conferred the ability to utilize 3-hydroxybutyrate as a carbon source (Aneja and Charles, *J. Bacteriol.* 181(3):849-857 (1999)). Additional candidates can be found in *Pseudomonas fragi* (Ito et al., *J. Mol. Biol.* 355(4) 722-733 (2006)) and *Ralstonia pickettii* (Takanashi et al., *Antonie van Leeuwenoek*, 95(3):249-262 (2009)). Recombinant 3-ketoacid reductase enzymes with broad substrate range and high activity have been characterized in US Application 2011/0201072, and are incorporated by reference herein. The mitochondrial 3-hydroxybutyrate dehydrogenase (bdh) from the human heart which has been cloned and characterized (Marks et al., *J. Biol. Chem.* 267:15459-15463 (1992)). Yet another secondary ADH, sadH of *Candida parapsilosis*, demonstrated activity on 3-oxobutanol (Matsuyama et al. *J Mol Cat B Enz*, 11:513-521 (2001)).

| Gene | GenBank Accession No. | GI No. | Organism |
|---|---|---|---|
| mdh | AAC76268.1 | 1789632 | *Escherichia coli* |
| ldhA | NP_415898.1 | 16129341 | *Escherichia coli* |
| MDH1 | NP_012838 | 6322765 | *Saccharomyces cerevisiae* |
| MDH2 | NP_014515 | 116006499 | *Saccharomyces cerevisiae* |
| MDH3 | NP_010205 | 6320125 | *Saccharomyces cerevisiae* |
| KLLA0E07525p | XP_454288.1 | 50308571 | *Kluyveromyces lactis* NRRL Y-1140 |
| YALI0D16753g | XP_502909.1 | 50550873 | *Yarrowia lipolytica* |
| CTRG_01021 | XP_002546239.1 | 255722609 | *Candida tropicalis* MYA-3404 |
| ldh | YP_725182.1 | 113866693 | *Ralstonia eutropha* |
| adh | AAA23199.2 | 60592974 | *Clostridium beijerinckii* NRRL B593 |
| adh | P14941.1 | 113443 | *Thermoanaerobacter brockii* HTD4 |
| sadh | CAD36475 | 21615553 | *Rhodococcus ruber* |
| adhA | AAC25556 | 3288810 | *Pyrococcus furiosus* |
| PRK13394 | BAD86668.1 | 57506672 | *Pseudomonas fragi* |
| Bdh1 | BAE72684.1 | 84570594 | *Ralstonia pickettii* |
| Bdh2 | BAE72685.1 | 84570596 | *Ralstonia pickettii* |
| Bdh3 | BAF91602.1 | 158937170 | *Ralstonia pickettii* |
| bdh | AAA58352.1 | 177198 | *Homo sapiens* |
| sadh | BAA24528.1 | 2815409 | *Candida parapsilosis* |

Alcohol dehydrogenases that reduce 3-ketoacids to their corresponding 3-hydroxyacids, required for the reduction of 3-oxo-4-hydroxypentanoate (3C), have also been characterized. These enzymes include 3-hydroxybutyrate dehydrogenase (EC 1.1.1.30), 3-hydroxyisobutyrate dehydrogenase (EC 1.1.1.31), threonine dehydrogenase (EC 1.1.1.103), 3-hydroxypropionate dehydrogenase (EC 1.1.1.298) and benzyl-2-methyl-3-hydroxybutanoate dehydrogenase (EC 1.1.1.217). Recombinant 3-ketoacid reductase enzymes with broad substrate range and high activity have been characterized in US Application 2011/0201072, and are incorporated by reference herein. The mitochondrial 3-hydroxybutyrate dehydrogenase (bdh) from the human heart which has been cloned and characterized (Marks et al., *J. Biol. Chem.* 267:15459-15463 (1992)). Secondary alcohol dehydrogenases described above are also suitable here.

| Gene | GenBank Accession No. | GI No. | Organism |
|---|---|---|---|
| Bdh | AAA58352.1 | 177198 | Homo sapiens |

Alcohol dehydrogenase enzymes active on allyl alcohols are suitable for reducing crotyl aldehyde to crotyl alcohol (1J). Crotyl aldehyde reductase activity has been demonstrated by mdr of *Synechocystis* sp. PCC 6803 (Shimakawa et al, *Biosci Biotechnol Biochem* 77:2441-8 (2013)). An exemplary allyl alcohol dehydrogenase is the NtRed-1 enzyme from *Nicotiana tabacum* (Matsushima et al, *Bioorg Chem* 36: 23-8 (2008)). A similar enzyme has been characterized in *Pseudomonas putida* MB 1 but the enzyme has not been associated with a gene to date (Malone et al, *AEM* 65: 2622-30 (1999)). Yet another allyl alcohol dehydrogenase is the geraniol dehydrogenase enzymes of *Castellaniella defragrans, Carpoglyphus lactis* and *Ocimum basilicum* (Lueddeke et al, *AEM* 78:2128-36 (2012)). Alcohol dehydrogenase enzymes with broad substrate specificity are also applicable here, such as include alrA encoding a medium-chain alcohol dehydrogenase for C2-C14 (Tani et al., *Appl. Environ. Microbiol.* 66:5231-5235 (2000)), yqhD, yahK, adhE and fucO from *E. coli* (Sulzenbacher et al., J Mol Biol 342:489-502 (2004)), and bdh I and bdh II from *C. acetobutylicum* which converts butyryaldehyde into butanol (Walter et al, *J. Bacteriol* 174:7149-7158 (1992)). YqhD of *E. coli* catalyzes the reduction of a wide range of aldehydes using NADPH as the cofactor, with a preference for chain lengths longer than C(3) (Sulzenbacher et al, *J Mol Biol* 342:489-502 (2004); Perez et al., *J Biol. Chem.* 283:7346-7353 (2008)). The adhA gene product from *Zymomonas mobilis* has been demonstrated to have activity on a number of aldehydes including formaldehyde, acetaldehyde, propionaldehyde, butyraldehyde, and acrolein (Kinoshita et al., *Appl Microbiol Biotechnol* 22:249-254 (1985)).

| Gene | GenBank Accession No. | GI No. | Organism |
|---|---|---|---|
| MDR | BAM52497.1 | 407959257 | Synechocystis sp. PCC 6803 |
| NT-RED1 | BAA89423 | 6692816 | Nicotiana tabacum |
| geoA | CCF55024.1 | 372099287 | Castellaniella defragrans |
| GEDH1 | Q2KNL6.1 | 122200955 | Ocimum basilicum |
| GEDH | BAG32342.1 | 188219500 | Carpoglyphus lactis |
| alrA | BAB12273.1 | 9967138 | Acinetobacter sp. strain M-1 |
| ADH2 | NP_014032.1 | 6323961 | Saccharomyces cerevisiae |
| fucO | NP_417279.1 | 16130706 | Escherichia coli |
| yqhD | NP_417484.1 | 16130909 | Escherichia coli |
| yahK | P75691.1 | 2492774 | Escherichia coli |
| adhE | NP_415757.1 | 16129202 | Escherichia coli |
| bdh I | NP_349892.1 | 15896543 | Clostridium acetobutylicum |
| bdh II | NP_349891.1 | 15896542 | Clostridium acetobutylicum |
| adhA | YP_162971.1 | 56552132 | Zymomonas mobilis |
| bdh | BAF45463.1 | 124221917 | Clostridium saccharoperbutylacetonicum |

Alcohol dehydrogenases active on 3-hydroxyacyl-CoA and 2-hydroxyacyl-CoA substrates catalyze the reduction of 2-oxopent-3-enoyl-CoA (FIG. 1O) and 3-oxo-4-hydroxypentanoyl-CoA (FIG. 3G) to their corresponding hydroxyacyl-CoA products. 3-Oxoacyl-CoA reductase enzymes (EC 1.1.1.35) convert 3-oxoacyl-CoA molecules into 3-hydroxyacyl-CoA molecules and are often involved in fatty acid beta-oxidation or phenylacetate catabolism. For example, subunits of two fatty acid oxidation complexes in *E. coli*, encoded by fadB and fadJ, function as 3-hydroxyacyl-CoA dehydrogenases (Binstock et al., *Methods Enzymol.* 71 Pt C:403-411 (1981)). The paaH gene product has a similar activity (Nogales et al., 153:357-365 (2007)). Additional 3-oxoacyl-CoA enzymes include the gene products of phaC in *Pseudomonas putida* (Olivera et al., *Proc. Natl. Acad. Sci U.S.A* 95:6419-6424 (1998)) and paaC in *Pseudomonas fluorescens* (Di et al., 188:117-125 (2007)). These enzymes catalyze the reversible oxidation of 3-hydroxyadipyl-CoA to 3-oxoadipyl-CoA during the catabolism of phenylacetate or styrene. Acetoacetyl-CoA reductase enzymes include hbd of *Clostridium acetobutylicum* (Youngleson et al., *J Bacteriol.* 171:6800-6807 (1989)), phbB from *Zoogloea ramigera* (Ploux et al., *Eur. J Biochem.* 174:177-182 (1988)) and phaB from *Rhodobacter sphaeroides* (Alber et al., *Mol. Microbiol* 61:297-309 (2006)). The former gene is NADPH-dependent, its nucleotide sequence has been determined (Peoples et al., *Mol. Microbiol* 3:349-357 (1989)) and the gene has been expressed in *E. coli*. Substrate specificity studies on the gene led to the conclusion that it could accept 3-oxopropionyl-CoA as a substrate besides acetoacetyl-CoA (Ploux et al., *Eur. J Biochem.* 174:177-182 (1988)). 3-Hydroxyacyl-CoA dehydrogenases that accept longer acyl-CoA substrates (eg. EC 1.1.1.35) are typically involved in beta-oxidation. An example is HSD17B10 in *Bos taurus* (WAKIL et al., *J Biol. Chem.* 207:631-638 (1954)). An exemplary 2-oxoacyl-CoA reductase is the 3-hydroxy-2-methylbutyryl-CoA dehydrogenase (EC 1.1.1.178) of *Pseudomonas putida*, which catalyzes the reduction of 3-methyl-2-oxopentanoyl-CoA, in addition to its native activity (Conrad et al, J Bacteriol 118:103-11 (1974)).

| Protein | GENBANK ID | GI NUMBER | ORGANISM |
|---|---|---|---|
| fadB | P21177.2 | 119811 | Escherichia coli |
| fadJ | P77399.1 | 3334437 | Escherichia coli |
| paaH | NP_415913.1 | 16129356 | Escherichia coli |
| Hbd2 | EDK34807.1 | 146348271 | Clostridium kluyveri |
| Hbd1 | EDK32512.1 | 146345976 | Clostridium kluyveri |
| phaC | NP_745425.1 | 26990000 | Pseudomonas putida |
| paaC | ABF82235.1 | 106636095 | Pseudomonas fluorescens |
| HSD17B10 | O02691.3 | 3183024 | Bos taurus |
| phbB | P23238.1 | 130017 | Zoogloea ramigera |
| phaB | YP_353825.1 | 77464321 | Rhodobacter sphaeroides |
| phaB | BAA08358 | 675524 | Paracoccus denitrificans |
| Hbd | NP_349314.1 | 15895965 | Clostridium acetobutylicum |

-continued

| Protein | GENBANK ID | GI NUMBER | ORGANISM |
|---|---|---|---|
| Hbd | AAM14586.1 | 20162442 | *Clostridium beijerinckii* |
| HSD17B10 | O02691.3 | 3183024 | *Bos taurus* |

1.2.1.b Acyl-CoA Reductase (Aldehyde Forming)

Acetyl-CoA reductase (an acyl-CoA reductase in EC class 1.2.1.-) catalyzes the reduction of acetyl-CoA to acetaldehyde. Several acyl-CoA dehydrogenases reduce an acyl-CoA to its corresponding aldehyde and represent suitable enzyme candidates for catalyzing step A of FIGS. 1 and 2. The NAD(P)H dependent reduction of acetyl-CoA to acetaldehyde is catalyzed by acylating acetaldehyde dehydrogenase (EC 1.2.1.10). Acylating acetaldehyde dehydrogenase enzymes of *E. coli* are encoded by adhE and mhpF (Ferrandez et al, *J Bacteriol* 179:2573-81 (1997)). The *Pseudomonas* sp. CF600 enzyme, encoded by dmpF, participates in meta-cleavage pathways and forms a complex with 4-hydroxy-2-oxovalerate aldolase (Shingler et al, *J Bacteriol* 174:711-24 (1992)). Solventogenic organisms such as *Clostridium acetobutylicum* encode bifunctional enzymes with alcohol dehydrogenase and acetaldehyde dehydrogenase activities. The bifunctional *C. acetobutylicum* enzymes are encoded by bdh I and adhE2 (Walter, et al., *J. Bacteriol.* 174:7149-7158 (1992); Fontaine et al., *J. Bacteriol.* 184:821-830 (2002)). Yet another candidate for acylating acetaldehyde dehydrogenase is the ald gene from *Clostridium beijerinckii* (Toth, *Appl. Environ. Microbiol.* 65:4973-4980 (1999). This gene is very similar to the eutE acetaldehyde dehydrogenase genes of *Salmonella typhimurium* and *E. coli* (Toth, *Appl. Environ. Microbiol.* 65:4973-4980 (1999). Other exemplary enzymes with acetyl-CoA reductase activity are found in the EC 1.2.1.-enzyme class including fatty acyl-CoA reductase, succinyl-CoA reductase (EC 1.2.1.76), acetyl-CoA reductase, butyryl-CoA reductase and propionyl-CoA reductase (EC 1.2.1.3). Such enzymes include bphG of *Pseudomonas* sp (Powlowski, *J Bacteriol.* 175:377-385 (1993)), adhE in *Leuconostoc mesenteroides* and *Escherichia coli* (Kazahaya, *J. Gen. Appl. Microbiol.* 18:43-55 (1972); and Koo et al., *Biotechnol Lett.* 27:505-510 (2005)) and butyraldehyde dehydrogenase enzymes of solventogenic organisms such as *Clostridium saccharoperbutylacetonicum* (Kosaka et al., *Biosci Biotechnol Biochem.*, 71:58-68 (2007)). Enzymes outside the EC class 1.2.1. which convert acetyl-CoA to acetaldehyde include bifunctional dehydrogenase/aldolases which degrade 4-hydroxy-2-oxovalerate to pyruvate and acetyl-CoA.

| Protein | GenBank ID | GI Number | Organism |
|---|---|---|---|
| adhE | NP_415757.1 | 16129202 | *Escherichia coli* |
| mhpF | NP_414885.1 | 16128336 | *Escherichia coli* |
| dmpF | CAA43226.1 | 45683 | *Pseudomonas* sp. CF600 |
| adhE2 | AAK09379.1 | 12958626 | *Clostridium acetobutylicum* |
| bdh I | NP_349892.1 | 15896543 | *Clostridium acetobutylicum* |
| Ald | AAT66436 | 49473535 | *Clostridium beijerinckii* |
| eutE | NP_416950 | 16130380 | *Escherichia coli* |
| eutE | AAA80209 | 687645 | *Salmonella typhimurium* |
| bphG | BAA03892.1 | 425213 | *Pseudomonas* sp |
| adhE | AAV66076.1 | 55818563 | *Leuconostoc mesenteroides* |
| bld | AAP42563.1 | 31075383 | *Clostridium saccharoperbutylacetonicum* |
| dmpG | CAA43227.1 | 45684 | *Pseudomonas* sp. CF600 |
| dmpF | CAA43226.1 | 45683 | *Pseudomonas* sp. CF600 |

-continued

| Protein | GenBank ID | GI Number | Organism |
|---|---|---|---|
| bphI | ABE37049.1 | 91693852 | *Burkholderia xenovorans* |
| bphJ | ABE37050.1 | 91693853 | *Burkholderia xenovorans* |

2.3.1.b Beta-Ketothiolase

Beta-ketothiolase enzymes are required for the conversion of lactoyl-CoA and acetyl-CoA to 3-oxo-4-hydroxy-pentanoyl-CoA, shown in FIG. 3A. Suitable enzymes are found in EC class 2.3.1, and include beta-ketovaleryl-CoA thiolase, acetoacetyl-CoA thiolase and beta-ketoadipyl-CoA thiolase. Beta-ketovaleryl-CoA thiolase catalyzes the formation of beta-ketovalerate from acetyl-CoA and propionyl-CoA. *Zoogloea ramigera* possesses two ketothiolases that can form beta-ketovaleryl-CoA from propionyl-CoA and acetyl-CoA and *R. eutropha* has a beta-oxidation ketothiolase that is also capable of catalyzing this transformation (Gruys et al., U.S. Pat. No. 5,958,745). The sequences of these genes or their translated proteins have not been reported, but several genes in *R. eutropha*, *Z. ramigera*, or other organisms can be identified based on sequence homology to bktB from *R. eutropha*. Acetoacetyl-CoA thiolase converts two molecules of acetyl-CoA into acetoacetyl-CoA (EC 2.1.3.9). Exemplary acetoacetyl-CoA thiolase enzymes include the gene products of atoB from *E. coli* (Martin et al., *Nat. Biotechnol.* 21:796-802 (2003)), thlA and thlB from *C. acetobutylicum* (Hanai et al., *Appl. Environ. Microbiol.* 73:7814-7818 (2007); Winzer et al., *J. Mol. Microbiol. Biotechnol.* 2:531-541 (2000)), and ERG10 from *S. cerevisiae* (Hiser et al., *J. Biol. Chem.* 269:31383-31389 (1994)). Beta-ketoadipyl-CoA thiolase (EC 2.3.1.174), also called 3-oxoadipyl-CoA thiolase, converts beta-ketoadipyl-CoA to succinyl-CoA and acetyl-CoA, and is a key enzyme of the beta-ketoadipate pathway for aromatic compound degradation. The enzyme is widespread in soil bacteria and fungi including *Pseudomonas putida* (Harwood et al., *J. Bacteriol.* 176-6479-6488 (1994)) and *Acinetobacter calcoaceticus* (Doten et al., *J. Bacteriol.* 169:3168-3174 (1987)). The *P. putida* enzyme is a homotetramer bearing 45% sequence homology to beta-ketothiolases involved in PHB synthesis in *Ralstonia eutropha*, fatty acid degradation by human mitochondria and butyrate production by *Clostridium acetobutylicum* (Harwood et al., supra). A beta-ketoadipyl-CoA thiolase in *Pseudomonas knackmussii* (formerly sp. B13) has also been characterized (Gobel et al., *J. Bacteriol.* 184:216-223 (2002); Kaschabek et al., supra). BKT encoding genes and associated identifiers are shown in the table below.

| Protein | GenBank ID | GI Number | Organism |
|---|---|---|---|
| phaA | YP_725941.1 | 113867452 | *Ralstonia eutropha* |
| h16_A1713 | YP_726205.1 | 113867716 | *Ralstonia eutropha* |
| pcaF | YP_728366.1 | 116694155 | *Ralstonia eutropha* |
| h16_B1369 | YP_840888.1 | 116695312 | *Ralstonia eutropha* |
| h16_A0170 | YP_724690.1 | 113866201 | *Ralstonia eutropha* |
| h16_A0462 | YP_724980.1 | 113866491 | *Ralstonia eutropha* |
| h16_A1528 | YP_726028.1 | 113867539 | *Ralstonia eutropha* |
| h16_B0381 | YP_728545.1 | 116694334 | *Ralstonia eutropha* |
| h16_B0662 | YP_728824.1 | 116694613 | *Ralstonia eutropha* |
| h16_B0759 | YP_728921.1 | 116694710 | *Ralstonia eutropha* |
| h16_B0668 | YP_728830.1 | 116694619 | *Ralstonia eutropha* |
| h16_A1720 | YP_726212.1 | 113867723 | *Ralstonia eutropha* |
| h16_A1887 | YP_726356.1 | 113867867 | *Ralstonia eutropha* |

| Protein | GenBank ID | GI Number | Organism |
|---|---|---|---|
| phbA | P07097.4 | 135759 | *Zoogloea ramigera* |
| bktB | YP_002005382.1 | 194289475 | *Cupriavidus taiwanensis* |
| Rmet_1362 | YP_583514.1 | 94310304 | *Ralstonia metallidurans* |
| Bphy_0975 | YP_001857210.1 | 186475740 | *Burkholderia phymatum* |
| atoB | NP_416728 | 16130161 | *Escherichia coli* |
| thlA | NP_349476.1 | 15896127 | *Clostridium acetobutylicum* |
| thlB | NP_149242.1 | 15004782 | *Clostridium acetobutylicum* |
| ERG10 | NP_015297 | 6325229 | *Saccharomyces cerevisiae* |
| pcaF | NP_743536.1 | 506695 | *Pseudomonas putida* |
| pcaF | AAC37148.1 | 141777 | *Acinetobacter calcoaceticus* |
| catF | Q8VPF1.1 | 75404581 | *Pseudomonas knackmussii* |

2.7.1.a Kinase

CrotOH kinase enzymes catalyze the transfer of a phosphate group to the hydroxyl group of CrotOH, shown in step A of FIG. 4. The enzymes described below naturally possess such activity or can be engineered to exhibit this activity. Kinases that catalyze transfer of a phosphate group to an alcohol group are members of the EC 2.7.1 enzyme class. The table below lists several useful kinase enzymes in the EC 2.7.1 enzyme class.

| Enzyme Commission Number | Enzyme Name |
|---|---|
| 2.7.1.1 | hexokinase |
| 2.7.1.2 | glucokinase |
| 2.7.1.3 | ketohexokinase |
| 2.7.1.4 | fructokinase |
| 2.7.1.5 | rhamnulokinase |
| 2.7.1.6 | Galactokinase |
| 2.7.1.7 | Mannokinase |
| 2.7.1.8 | glucosamine kinase |
| 2.7.1.10 | phosphoglucokinase |
| 2.7.1.11 | 6-phosphofructokinase |
| 2.7.1.12 | gluconokinase |
| 2.7.1.13 | dehydrogluconokinase |
| 2.7.1.14 | sedoheptulokinase |
| 2.7.1.15 | ribokinase |
| 2.7.1.16 | ribulokinase |
| 2.7.1.17 | xylulokinase |
| 2.7.1.18 | phosphoribokinase |
| 2.7.1.19 | phosphoribulokinase |
| 2.7.1.20 | adenosine kinase |
| 2.7.1.21 | thymidine kinase |
| 2.7.1.22 | ribosylnicotinamide kinase |
| 2.7.1.23 | NAD+ kinase |
| 2.7.1.24 | dephospho-CoA kinase |
| 2.7.1.25 | adenylyl-sulfate kinase |
| 2.7.1.26 | riboflavin kinase |
| 2.7.1.27 | erythritol kinase |
| 2.7.1.28 | triokinase |
| 2.7.1.29 | glycerone kinase |
| 2.7.1.30 | glycerol kinase |
| 2.7.1.31 | glycerate kinase |
| 2.7.1.32 | choline kinase |
| 2.7.1.33 | pantothenate kinase |
| 2.7.1.34 | pantetheine kinase |
| 2.7.1.35 | pyridoxal kinase |
| 2.7.1.36 | mevalonate kinase |
| 2.7.1.39 | homoserine kinase |
| 2.7.1.40 | pyruvate kinase |
| 2.7.1.41 | glucose-1-phosphate phosphodismutase |
| 2.7.1.42 | riboflavin phosphotransferase |
| 2.7.1.43 | glucuronokinase |
| 2.7.1.44 | galacturonokinase |
| 2.7.1.45 | 2-dehydro-3-deoxygluconokinase |
| 2.7.1.46 | L-arabinokinase |
| 2.7.1.47 | D-ribulokinase |
| 2.7.1.48 | uridine kinase |
| 2.7.1.49 | hydroxymethylpyrimidine kinase |
| 2.7.1.50 | hydroxyethylthiazole kinase |
| 2.7.1.51 | L-fuculokinase |
| 2.7.1.52 | fucokinase |
| 2.7.1.53 | L-xylulokinase |
| 2.7.1.54 | D-arabinokinase |
| 2.7.1.55 | allose kinase |
| 2.7.1.56 | 1-phosphofructokinase |
| 2.7.1.58 | 2-dehydro-3-deoxygalactonokinase |
| 2.7.1.59 | N-acetylglucosamine kinase |
| 2.7.1.60 | N-acylmannosamine kinase |
| 2.7.1.61 | acyl-phosphate-hexose phosphotransferase |
| 2.7.1.62 | phosphoramidate-hexose phosphotransferase |
| 2.7.1.63 | polyphosphate-glucose phosphotransferase |
| 2.7.1.64 | inositol 3-kinase |
| 2.7.1.65 | scyllo-inosamine 4-kinase |
| 2.7.1.66 | undecaprenol kinase |
| 2.7.1.67 | 1-phosphatidylinositol 4-kinase |
| 2.7.1.68 | 1-phosphatidylinositol-4-phosphate 5-kinase |
| 2.7.1.69 | protein-Np-phosphohistidine-sugar phosphotransferase |
| 2.7.1.70 | identical to EC 2.7.1.37. |
| 2.7.1.71 | shikimate kinase |
| 2.7.1.72 | streptomycin 6-kinase |
| 2.7.1.73 | inosine kinase |
| 2.7.1.74 | deoxycytidine kinase |
| 2.7.1.76 | deoxyadenosine kinase |
| 2.7.1.77 | nucleoside phosphotransferase |
| 2.7.1.78 | polynucleotide 5'-hydroxyl-kinase |
| 2.7.1.79 | diphosphate-glycerol phosphotransferase |
| 2.7.1.80 | diphosphate-serine phosphotransferase |
| 2.7.1.81 | hydroxylysine kinase |
| 2.7.1.82 | ethanolamine kinase |
| 2.7.1.83 | pseudouridine kinase |
| 2.7.1.84 | alkylglycerone kinase |
| 2.7.1.85 | β-glucoside kinase |
| 2.7.1.86 | NADH kinase |
| 2.7.1.87 | streptomycin 3"-kinase |
| 2.7.1.88 | dihydrostreptomycin-6-phosphate 3'a-kinase |
| 2.7.1.89 | thiamine kinase |
| 2.7.1.90 | diphosphate-fructose-6-phosphate 1-phosphotransferase |
| 2.7.1.91 | sphinganine kinase |
| 2.7.1.92 | 5-dehydro-2-deoxygluconokinase |
| 2.7.1.93 | alkylglycerol kinase |
| 2.7.1.94 | acylglycerol kinase |
| 2.7.1.95 | kanamycin kinase |
| 2.7.1.100 | S-methyl-5-thioribose kinase |
| 2.7.1.101 | tagatose kinase |
| 2.7.1.102 | hamamelose kinase |
| 2.7.1.103 | viomycin kinase |
| 2.7.1.105 | 6-phosphofructo-2-kinase |
| 2.7.1.106 | glucose-1,6-bisphosphate synthase |
| 2.7.1.107 | diacylglycerol kinase |
| 2.7.1.108 | dolichol kinase |
| 2.7.1.113 | deoxyguanosine kinase |
| 2.7.1.114 | AMP-thymidine kinase |
| 2.7.1.118 | ADP-thymidine kinase |
| 2.7.1.119 | hygromycin-B 7"-O-kinase |
| 2.7.1.121 | phosphoenolpyruvate-glycerone phosphotransferase |

-continued

| Enzyme Commission Number | Enzyme Name |
|---|---|
| 2.7.1.122 | xylitol kinase |
| 2.7.1.127 | inositol-trisphosphate 3-kinase |
| 2.7.1.130 | tetraacyldisaccharide 4'-kinase |
| 2.7.1.134 | inositol-tetrakisphosphate 1-kinase |
| 2.7.1.136 | macrolide 2'-kinase |
| 2.7.1.137 | phosphatidylinositol 3-kinase |
| 2.7.1.138 | ceramide kinase |
| 2.7.1.140 | inositol-tetrakisphosphate 5-kinase |
| 2.7.1.142 | glycerol-3-phosphate-glucose phosphotransferase |
| 2.7.1.143 | diphosphate-purine nucleoside kinase |
| 2.7.1.144 | tagatose-6-phosphate kinase |
| 2.7.1.145 | deoxynucleoside kinase |
| 2.7.1.146 | ADP-dependent phosphofructokinase |
| 2.7.1.147 | ADP-dependent glucokinase |
| 2.7.1.148 | 4-(cytidine 5'-diphospho)-2-C-methyl-D-erythritol kinase |
| 2.7.1.149 | 1-phosphatidylinositol-5-phosphate 4-kinase |
| 2.7.1.150 | 1-phosphatidylinositol-3-phosphate 5-kinase |
| 2.7.1.151 | inositol-polyphosphate multikinase |
| 2.7.1.153 | phosphatidylinositol-4,5-bisphosphate 3-kinase |
| 2.7.1.154 | phosphatidylinositol-4-phosphate 3-kinase |
| 2.7.1.156 | adenosylcobinamide kinase |
| 2.7.1.157 | N-acetylgalactosamine kinase |
| 2.7.1.158 | inositol-pentakisphosphate 2-kinase |
| 2.7.1.159 | inositol-1,3,4-trisphosphate 5/6-kinase |
| 2.7.1.160 | 2'-phosphotransferase |
| 2.7.1.161 | CTP-dependent riboflavin kinase |
| 2.7.1.162 | N-acetylhexosamine 1-kinase |
| 2.7.1.163 | hygromycin B 4-O-kinase |
| 2.7.1.164 | O-phosphoseryl-tRNASec kinase |

Mevalonate kinase (EC 2.7.1.36) phosphorylates the terminal hydroxyl group of mevalonate. Gene candidates for this step include erg12 from *S. cerevisiae*, mvk from *Methanocaldococcus jannaschi*, MVK from *Homo sapeins*, and mvk from *Arabidopsis thaliana* col. Additional mevalonate kinase candidates include the feedback-resistant mevalonate kinase from the archeon *Methanosarcina mazei* (Primak et al, *AEM*, in press (2011)) and the Mvk protein from *Streptococcus pneumoniae* (Andreassi et al, Protein Sci, 16:983-9 (2007)). Mvk proteins from *S. cerevisiae, S. pneumoniae* and *M. mazei* were heterologously expressed and characterized in *E. coli* (Primak et al, supra). The *S. pneumoniae* mevalonate kinase was active on several alternate substrates including cylopropylmevalonate, vinylmevalonate and ethynylmevalonate (Kudoh et al, *Bioorg Med Chem* 18:1124-34 (2010)), and a subsequent study determined that the ligand binding site is selective for compact, electron-rich C(3)-substituents (Lefurgy et al, *J Biol Chem* 285:20654-63 (2010)).

| Protein | GenBank ID | GI Number | Organism |
|---|---|---|---|
| erg12 | CAA39359.1 | 3684 | *Sachharomyces cerevisiae* |
| mvk | Q58487.1 | 2497517 | *Methanocaldococcus jannaschii* |
| mvk | AAH16140.1 | 16359371 | *Homo sapiens* |
| mvk | NP_851084.1 | 30690651 | *Arabidopsis thaliana* |
| mvk | NP_633786.1 | 21227864 | *Methanosarcina mazei* |
| mvk | NP_357932.1 | 15902382 | *Streptococcus pneumoniae* |

Glycerol kinase also phosphorylates the terminal hydroxyl group in glycerol to form glycerol-3-phosphate. This reaction occurs in several species, including *Escherichia coli, Saccharomyces cerevisiae*, and *Thermotoga maritima*. The *E. coli* glycerol kinase has been shown to accept alternate substrates such as dihydroxyacetone and glyceraldehyde (Hayashi et al., *J Biol. Chem.* 242:1030-1035 (1967)). T, maritime has two glycerol kinases (Nelson et al., Nature 399:323-329 (1999)). Glycerol kinases have been shown to have a wide range of substrate specificity. Crans and Whiteside studied glycerol kinases from four different organisms (*Escherichia coli, S. cerevisiae, Bacillus stearothermophilus*, and *Candida mycoderma*) (Crans et al., *J. Am. Chem. Soc.* 107:7008-7018 (2010); Nelson et al., supra, (1999)). They studied 66 different analogs of glycerol and concluded that the enzyme could accept a range of substituents in place of one terminal hydroxyl group and that the hydrogen atom at C2 could be replaced by a methyl group. Interestingly, the kinetic constants of the enzyme from all four organisms were very similar.

| Protein | GenBank ID | GI Number | Organism |
|---|---|---|---|
| glpK | AP_003883.1 | 89110103 | *Escherichia coli* K12 |
| glpK1 | NP_228760.1 | 15642775 | *Thermotoga maritime* MSB8 |
| glpK2 | NP_229230.1 | 15642775 | *Thermotoga maritime* MSB8 |
| Gut1 | NP_011831.1 | 82795252 | *Saccharomyces cerevisiae* |

Homoserine kinase is another possible candidate. This enzyme is also present in a number of organisms including *E. coli, Streptomyces* sp, and *S. cerevisiae*. Homoserine kinase from *E. coli* has been shown to have activity on numerous substrates, including, L-2-amino,1,4-butanediol, aspartate semialdehyde, and 2-amino-5-hydroxyvalerate (Huo et al., *Biochemistry* 35:16180-16185 (1996); Huo et al., *Arch. Biochem. Biophys.* 330:373-379 (1996)). This enzyme can act on substrates where the carboxyl group at the alpha position has been replaced by an ester or by a hydroxymethyl group.

| Protein | GenBank ID | GI Number | Organism |
|---|---|---|---|
| thrB | BAB96580.2 | 85674277 | *Escherichia coli* K12 |
| SACT1DRAFT_4809 | ZP_06280784.1 | 282871792 | *Streptomyces* sp. ACT-1 |
| Thr1 | AAA35154.1 | 172978 | *Saccharomyces serevisiae* |

Figure 8:
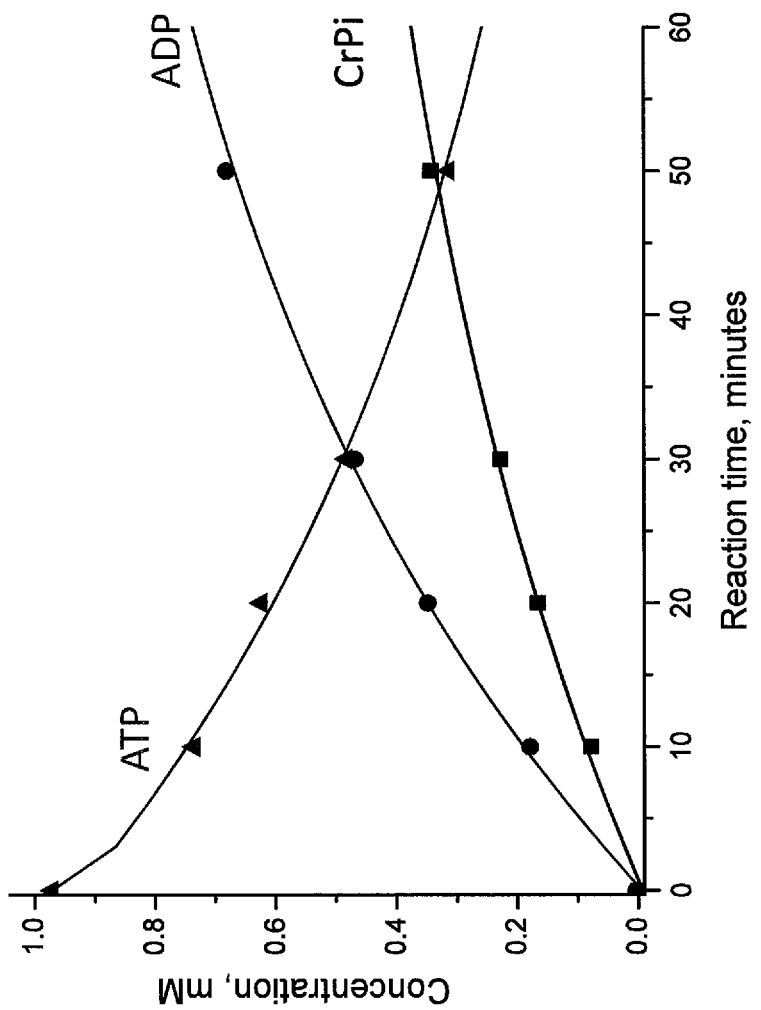
FIG. 8 is a graph of in vitro formation of crotyl phosphate (CrPi) and ADP over time from a composition including ATP, crotyl alcohol, and hydroxyethylthiazole kinase.

Other classes of kinases that can catalyze the phosphorylation of crotyl alcohol are hydroxyethylthiazole kinase (FIG. 8 is a graph of in vitro formation of crotyl phosphate (CrPi) and ADP over time from a composition including ATP, crotyl alcohol, and hydroxyethylthiazole kinase), thiamine kinase, pantothenate kinase, 4-diphosphocytidyl-2-C-methyl-D-erythritol kinase, riboflavin kinase, L-fuculokinase and choline kinase. Exemplary gene candidates for each of these classes are shown below.

The table below provides gene candidates for hydroxyethyl thiazole kinases

| Protein | GenBank ID | GI Number | Organism |
|---|---|---|---|
| ThiM | YP_007535827.1 | 16080881 | *Bacillus subtilis* |
| Thi6 | CAA97929.1 | 1370444 | *Saccharomyces serevisiae* |

| Protein | GenBank ID | GI Number | Organism |
|---|---|---|---|
| ThiM | NP_372616.1 | 15925082 | Staphylococcus aureus |
| PH1157, thiM (analogue of thiK) | NP_143059.1 | 14590984 | Pyrococcus horikoshii OT3 |
| ThiM | Q830K4 | 81585041 | Enterococcus faecalis V583 |
| ThiM | YP_006701495 | 405760899 | Streptococcus pneumoniae SPNA45 |
| ThiM | YP_004888181 | 380031190 | Lactobacillus plantarum WCFS1 |
| ThiM | WP_012906431 | 502670591 | Citrobacter rodentium |
| ThiM | NP_461091 | 16765476 | Salmonella enterica subsp. Enterica LT2 |
| ThiM | YP_771477 | 116255644 | Rhizobium leguminosarum bv. viciae 3841 |
| ThiM (b2104) | AAC75165.1 | 1788421 | Escherichia coli str. K-12 substr. MG1655 |

Some candidate thiamine kinases are:

| Protein | GenBank ID | GI Number | Organism |
|---|---|---|---|
| thiK | AAC74190.1 | 1787349 | Escherichia coli K12 |
| thiK | NP_460178.1 | 16764563 | Salmonella enterica subsp. enterica serovar Typhimurium str. LT2 |

Examplary fuculokinases are:

| Protein | GenBank ID | GI Number | Organism |
|---|---|---|---|
| b2803 | AAC75845.1 | 1789168 | Escherichia coli K12 MG1655 |
| STM14_3591 | ACY90002.1 | 267995117 | Salmonella enterica subsp. enterica serovar Typhimurium str. 14028S |
| D186_16909 | EKS55716.1 | 411772069 | Citrobacter freundii ATCC 8090 = MTCC 1658 |

6-hydroxymethyl-7,8-dihydropterin pyrophosphokinase can also carry the described transformation. Gene candidates from this class are listed below.

| Protein | GenBank ID | GI Number | Organism |
|---|---|---|---|
| folK | AAC73253.1 | 1786335 | Escherichia coli K12 |
| folK | NP_816865.1 | 29377711 | Enterococcus faecalis V583 |

Pantothenate kinases that can catalyze the transformation are:

| Protein | GenBank ID | GI Number | Organism |
|---|---|---|---|
| CoaA | YP_006514461.1 | 397672926 | Mycobacterium tuberculosis H37Rv |
| CoaA | YP_491482.1 | 388479290 | Escherichia coli K12 |
| CoaX | Q9WZY5.1 | 81553296 | Thermotoga maritima MSB8 |
| Sav2130 | NP_372654.1 | 15925120 | Staphylococcus aureus subsp. aureus Mu50 |

Yet another candidate enzyme class of interest is 4-(cytidine 5'-diphospho)-2-C-methyl-D-erythritol kinase (2.7.1.148). Gene candidates from this class are:

| Protein | GenBank ID | GI Number | Organism |
|---|---|---|---|
| ispE | NP_415726.1 | 16129171 | Escherichia coli K12 |
| ispE | KBJ36713.1 | 623367758 | Mycobacterium tuberculosis H37Rv |

2.7.4.a Phosphokinase

2-Butenyl-4-phosphate kinase enzymes catalyze the transfer of a phosphate group to the phosphate group of 2-butenyl-4-phosphate (FIG. 4B). The enzymes described below naturally possess such activity or can be engineered to exhibit this activity. Kinases that catalyze transfer of a phosphate group to another phosphate group are members of the EC 2.7.4 enzyme class. The table below lists several useful kinase enzymes in the EC 2.7.4 enzyme class.

| Enzyme Commission Number | Enzyme Name |
|---|---|
| 2.7.4.1 | polyphosphate kinase |
| 2.7.4.2 | phosphomevalonate kinase |
| 2.7.4.3 | adenylate kinase |
| 2.7.4.4 | nucleoside-phosphate kinase |
| 2.7.4.6 | nucleoside-diphosphate kinase |
| 2.7.4.7 | phosphomethylpyrimidine kinase |
| 2.7.4.8 | guanylate kinase |
| 2.7.4.9 | dTMP kinase |
| 2.7.4.10 | nucleoside-triphosphate-adenylate kinase |
| 2.7.4.11 | (deoxy)adenylate kinase |
| 2.7.4.12 | T2-induced deoxynucleotide kinase |
| 2.7.4.13 | (deoxy)nucleoside-phosphate kinase |
| 2.7.4.14 | cytidylate kinase |
| 2.7.4.15 | thiamine-diphosphate kinase |
| 2.7.4.16 | thiamine-phosphate kinase |
| 2.7.4.17 | 3-phosphoglyceroyl-phosphate-polyphosphate phosphotransferase |
| 2.7.4.18 | farnesyl-diphosphate kinase |
| 2.7.4.19 | 5-methyldeoxycytidine-5'-phosphate kinase |
| 2.7.4.20 | dolichyl-diphosphate-polyphosphate phosphotransferase |
| 2.7.4.21 | inositol-hexakisphosphate kinase |
| 2.7.4.22 | UMP kinase |
| 2.7.4.23 | ribose 1,5-bisphosphate phosphokinase |
| 2.7.4.24 | diphosphoinositol-pentakisphosphate kinase |
| 2.7.4.- | Farnesyl monophosphate kinase |
| 2.7.4.- | Geranyl-geranyl monophosphate kinase |
| 2.7.4.- | Phytyl-phosphate kinase |
| 2.7.4.26 | isopentenyl phosphate kinase |

Phosphomevalonate kinase enzymes are of particular interest. Phosphomevalonate kinase (EC 2.7.4.2) catalyzes the analogous transformation to 2-butenyl-4-phosphate kinase. This enzyme is encoded by erg8 in Saccharomyces cerevisiae (Tsay et al., Mol. Cell Biol. 11:620-631 (1991)) and mvaK2 in Streptococcus pneumoniae, Staphylococcus aureus and Enterococcus faecalis (Doun et al., Protein Sci. 14:1134-1139 (2005); Wilding et al., J Bacteriol. 182:4319-4327 (2000)). The Streptococcus pneumoniae and Enterococcus faecalis enzymes were cloned and characterized in E. coli (Pilloff et al., J Biol. Chem. 278:4510-4515 (2003); Doun et al., Protein Sci. 14:1134-1139 (2005)). The S. pneumoniae phosphomevalonate kinase was active on several alternate substrates including cylopropylmevalonate phosphate, vinylmevalonate phosphate and ethynylmevalonate phosphate (Kudoh et al, Bioorg Med Chem 18:1124-34 (2010)). These and related enzymes are shown in the table below.

| Enzyme | Genbank ID | GI Number | Organism |
|---|---|---|---|
| Erg8 | AAA34596.1 | 171479 | *Saccharomyces cerevisiae* |
| mvaK2 | AAG02426.1 | 9937366 | *Staphylococcus aureus* |
| mvaK2 | AAG02457.1 | 9937409 | *Streptococcus pneumoniae* |
| mvaK2 | AAG02442.1 | 9937388 | *Enterococcus faecalis* |
| phosphomevalonate kinase | YP_008718968.1 | 554649894 | *Carnobacterium* sp. WN1359 |
| phosphomevalonate kinase | YP_004889541.1 | 380032550 | *Lactobacillus plantarum* WCFS1 |
| phosphomevalonate kinase | BAD86802.1 | 57753872 | *Streptomyces* sp. KO-3988 |
| phosphomevalonate kinase | YP_006806525.1 | 407642766 | *Nocardia brasiliensis* ATCC 700358 |
| phosphomevalonate kinase | YP_008165221.1 | 521188403 | *Corynebacterium terpenotabidum* Y-11 |
| isopentenyl phosphate kinase | NP_247007.1 | 15668214 | *Methanocaldococcus jannaschii* |
| isopentenyl phosphate kinase | NP_393581.1 | 16081271 | *Thermoplasma acidophilum* DSM 1728 |
| isopentenyl phosphate kinase | NP_275190.1 | 15678076 | *Methanothermobacter thermautotrophicus* |
| isopentenyl phosphate kinase | YP_003356693.1 | 282164308 | *Methanocella paludicola* SANAE |
| isopentenyl phosphate kinase | YP_304959.1 | 73668944 | *Methanosarcina barkeri* Fusaro |
| isopentenyl phosphate kinase | YP_007714098.1 | 478483448 | *Candidatus Methanomethylophilus alvus* Mx1201 |
| isopentenyl phosphate kinase | AAB84554.1 | 2621082 | *Methanobacterium thermoautotrophicum* |
| Isopentenyl phosphate kinase (IPK) | D4GWT7.1 | 635552533 | *Haloferax volcanii* |

Additional kinase enzymes include fosfomycin kinase (FomA) which is highly homologous to isopentenyl phosphate kinase and is an antibiotic resistance enzyme found in a few strains of *Streptomyces* and *Pseudomonas* (Mabangalo et al. Biochemistry 51(4):917-925 (2012)). Superposition of *Thermoplasma acidophilum* (THA) IPK and FomA structures aligns their respective substrates and catalytic residues. These residues are conserved only in the IPK and FomA members of the phosphate subdivision of the amino acid kinase superfamily. IPK from *Thermoplasma acidophilum* has been shown to have activity on fosmomycin. An exemplary fosfomycin kinase is that from *Streptomyces wedmorensis*, Genbank ID BAA32493.1 and GI number 3452580.

Farnesyl monophosphate kinase enzymes catalyze the CTP dependent phosphorylation of farnesyl monophosphate to farnesyl diphosphate. Similarly, geranylgeranyl phosphate kinase catalyzes CTP dependent phosphorylation. Enzymes with these activities were identified in the microsomal fraction of cultured *Nicotiana tabacum* (Thai et al, PNAS 96:13080-5 (1999)). However, the associated genes have not been identified to date.

Additional enzymes include those of the EC 2.7.2.8 class. This class is exemplified by acetylglutamate kinase, including the exemplary enzymes below:

| | | | |
|---|---|---|---|
| acetylglutamate kinase | NP_126233.1 | 14520758 | *Pyrococcus abyssi* GE5 |
| acetylglutamate kinase | NP_579365.1 | 18978008 | *Pyrococcus furiosus* DSM 3638 |
| acetylglutamate kinase | AAB88966.1 | 2648231 | *Archaeoglobus fulgidus* DSM4304 |

2.7.6.a Diphosphokinase

CrotOH diphosphokinase enzymes catalyze the transfer of a diphosphate group to the hydroxyl group of CrotOH, shown in step I of FIG. 1. The enzymes described below naturally possess such activity or can be engineered to exhibit this activity. Kinases that catalyze transfer of a diphosphate group are members of the EC 2.7.6 enzyme class. The table below lists several useful kinase enzymes in the EC 2.7.6 enzyme class.

| Enzyme Commission Number | Enzyme Name |
|---|---|
| 2.7.6.1 | ribose-phosphate diphosphokinase |
| 2.7.6.2 | thiamine diphosphokinase |
| 2.7.6.3 | 2-amino-4-hydroxy-6-hydroxymethyldihydropteridine diphosphokinase |
| 2.7.6.4 | nucleotide diphosphokinase |
| 2.7.6.5 | GTP diphosphokinase |

Of particular interest are ribose-phosphate diphosphokinase enzymes which have been identified in *Escherichia coli* (Hove-Jenson et al., J Biol Chem, 1986, 261(15); 6765-71) and *Mycoplasma pneumoniae* M129 (McElwain et al, International Journal of Systematic Bacteriology, 1988, 38:417-423) as well as thiamine diphosphokinase enzymes. Exemplary thiamine diphosphokinase enzymes are found in *Arabidopsis thaliana* (Ajjawi, Plant Mol Biol, 2007, 65(1-2); 151-62).

| Protein | GenBank ID | GI Number | Organism |
|---|---|---|---|
| prs | NP_415725.1 | 16129170 | *Escherichia coli* |
| prsA | NP_109761.1 | 13507812 | *Mycoplasma pneumoniae* M129 |
| TPK1 | BAH19964.1 | 222424006 | *Arabidopsis thaliana* col |
| TPK2 | BAH57065.1 | 227204427 | *Arabidopsis thaliana* col |

4.1.1.b Decarboxylase, Alkene Forming

Olefin-forming decarboxylase enzymes suitable for converting 3-hydroxypent-4-enoate to butadiene (Step K of FIG. 2) include mevalonate diphosphate decarboxylase (MDD, EC 4.1.1.33) and similar enzymes. MDD participates in the mevalonate pathway for isoprenoid biosynthesis, where it catalyzes the ATP-dependent decarboxylation of mevalonate diphosphate to isopentenyl diphosphate. The MDD enzyme of *S. cerevisiae* was heterologously expressed in *E. coli*, where it was shown to catalyze the decarboxylation of 3-hydroxyacids to their corresponding alkenes (WO 2010/001078; Gogerty and Bobik, *Appl. Environ. Microbiol.*, p. 8004-8010, Vol. 76, No. 24 (2010)). Products formed by this enzyme include isobutylene, propylene and ethylene. Two evolved variants of the *S. cerevisiae* MDD, ScMDD1 (I145F) and ScMDD2 (R74H), achieved 19-fold and 38-fold increases in isobutylene-forming activity compared to the wild-type enzyme (WO 2010/001078). Other exemplary MDD genes are MVD in *Homo sapiens* and MDD in *Staphylococcus aureus* and *Trypsonoma brucei* (Toth et al., *J Biol. Chem.* 271:7895-7898 (1996); Byres et al., *J Mol. Biol.* 371:540-553 (2007)).

| Protein | GenBank ID | GI Number | Organism |
|---|---|---|---|
| MDD | NP_014441.1 | 6324371 | *Saccharomyces cerevisiae* |
| MVD | NP_002452.1 | 4505289 | *Homo sapiens* |
| MDD | ABQ48418.1 | 147740120 | *Staphylococcus aureus* |
| MDD | EAN78728.1 | 70833224 | *Trypsonoma brucei* |

4.1.2.a Aldehyde Lyase

The condensation of pyruvate and acetaldehyde to 4-hydroxy-2-oxovalerate (Step B of FIGS. 1 and 2) is catalyzed by 4-hydroxy-2-oxovalerate aldolase (EC 4.1.3.39). This enzyme participates in pathways for the degradation of phenols, cresols and catechols. The *E. coli* enzyme, encoded by mhpE, is highly specific for acetaldehyde as an acceptor (Pollard et al., *Appl Environ Microbiol* 64:4093-4094 (1998)). Similar enzymes are encoded by the cmtG and todH genes of *Pseudomonas putida* (Lau et al., *Gene* 146:7-13 (1994); Eaton, *J Bacteriol.* 178:1351-1362 (1996)). In *Pseudomonas* CF600, this enzyme is part of a bifunctional aldolase-dehydrogenase heterodimer encoded by dmpFG (Manjasetty et al., *Acta Crystallogr. D. Biol Crystallogr.* 57:582-585 (2001)). The dehydrogenase functionality interconverts acetaldehyde and acetyl-CoA (Step A of FIGS. 1 and 2) and channels the acetaldehyde intermediate to the aldolase. Substrate channeling provides the advantage of reduced cellular concentrations of acetaldehyde, toxic to some cells, and may also reduce acetaldehyde-derived byproducts such as ethanol and acetate. A similar aldolase-dehydrogenase complex is encoded by BphIJ of *Burkholderia xenovorans* (Baker et al, Biochem 48:6551-8 (2009)).

| Gene | GenBank ID | GI Number | Organism |
|---|---|---|---|
| mhpE | AAC73455.1 | 1786548 | *Escherichia coli* |
| cmtG | AAB62295.1 | 1263190 | *Pseudomonas putida* |
| todH | AAA61944.1 | 485740 | *Pseudomonas putida* |
| dmpG | CAA43227.1 | 45684 | *Pseudomonas* sp. CF600 |
| dmpF | CAA43226.1 | 45683 | *Pseudomonas* sp. CF600 |
| bphI | ABE37049.1 | 91693852 | *Burkholderia xenovorans* |
| bphJ | ABE37050.1 | 91693853 | *Burkholderia xenovorans* |

4.2.3 Synthase (Alkene Forming)

Butadiene Synthase (BDS), shown in Step C of FIG. 4, catalyzes the conversion of 2-butenyl-4-diphosphate to 1,3-butadiene. The enzymes described below naturally possess such activity or can be engineered to exhibit this activity. Carbon-oxygen lyases that operate on phosphates are found in the EC 4.2.3 enzyme class. The table below lists several useful enzymes in EC class 4.2.3.

| Enzyme Commission Number | Enzyme Name |
|---|---|
| 4.2.3.15 | Myrcene synthase |
| 4.2.3.26 | Linalool synthase |
| 4.2.3.27 | Isoprene synthase |
| 4.2.3.36 | Terpentriene sythase |
| 4.2.3.46 | (E,E)-alpha-Farnesene synthase |
| 4.2.3.47 | Beta-Farnesene synthase |
| 4.2.3.49 | Nerolidol synthase |

Particularly useful enzymes include isoprene synthase, myrcene synthase and farnesene synthase. Enzyme candidates are described below, and in the enzymes and classes for FIG. 15, Step F.

Isoprene synthase naturally catalyzes the conversion of dimethylallyl diphosphate to isoprene, but can also catalyze the synthesis of 1,3-butadiene from 2-butenyl-4-diphosphate. Isoprene synthases can be found in several organisms including *Populus alba* (Sasaki et al., FEBS Letters, 2005, 579 (11), 2514-2518), *Pueraria montana* (Lindberg et al., *Metabolic Eng*, 12(1):70-79 (2010); Sharkey et al., *Plant Physiol.*, 137(2):700-712 (2005)), and *Populus tremula* x *Populus alba*, also called *Populus canescens* (Miller et al., Planta, 2001, 213 (3), 483-487). The crystal structure of the *Populus canescens* isoprene synthase was determined (Koksal et al, *J Mol Biol* 402:363-373 (2010)). Additional isoprene synthase enzymes are described in (Chotani et al., WO/2010/031079, Systems Using Cell Culture for Production of Isoprene; Cervin et al., US Patent Application 20100003716, Isoprene Synthase Variants for Improved Microbial Production of Isoprene).

| Protein | GenBank ID | GI Number | Organism |
|---|---|---|---|
| ispS | BAD98243.1 | 63108310 | *Populus alba* |
| ispS | AAQ84170.1 | 35187004 | *Pueraria montana* |
| ispS | CAC35696.1 | 13539551 | *Populus tremula* x *Populus alba* |

Myrcene synthase enzymes catalyze the dephosphorylation of geranyl diphosphate to beta-myrcene (EC 4.2.3.15). Exemplary myrcene synthases are encoded by MST2 of *Solanum lycopersicum* (van Schie et al, Plant Mol Biol 64:D473-79 (2007)), TPS-Myr of *Picea abies* (Martin et al, Plant Physiol 135:1908-27 (2004)) g-myr of *Abies grandis* (Bohlmann et al, J Biol Chem 272:21784-92 (1997)) and TPS10 of *Arabidopsis thaliana* (Bohlmann et al, Arch Biochem Biophys 375:261-9 (2000)). These enzymes were heterologously expressed in *E. coli*.

| Protein | GenBank ID | GI Number | Organism |
|---|---|---|---|
| MST2 | ACN58229.1 | 224579303 | *Solanum lycopersicum* |
| TPS-Myr | AAS47690.2 | 77546864 | *Picea abies* |
| G-myr | O24474.1 | 17367921 | *Abies grandis* |
| TPS10 | EC07543.1 | 330252449 | *Arabidopsis thaliana* |

Farnesyl diphosphate is converted to alpha-farnesene and beta-farnesene by alpha-farnesene synthase and beta-farnesene synthase, respectively. Exemplary alpha-farnesene synthase enzymes include TPS03 and TPS02 of *Arabidopsis thaliana* (Faldt et al, *Planta* 216:745-51 (2003); Huang et al, *Plant Physiol* 153:1293-310 (2010)), afs of *Cucumis sativus* (Mercke et al, Plant Physiol 135:2012-14 (2004), eafar of *Malus x domestica* (Green et al, Phytochem 68:176-88 (2007)) and TPS-Far of *Picea abies* (Martin, supra). An exemplary beta-farnesene synthase enzyme is encoded by TPS1 of *Zea mays* (Schnee et al, Plant Physiol 130:2049-60 (2002)).

| Protein | GenBank ID | GI Number | Organism |
|---|---|---|---|
| TPS03 | A4FVP2.1 | 205829248 | *Arabidopsis thaliana* |
| TPS02 | P0CJ43.1 | 317411866 | *Arabidopsis thaliana* |
| TPS-Far | AAS47697.1 | 44804601 | *Picea abies* |
| afs | AAU05951.1 | 51537953 | *Cucumis sativus* |
| eafar | Q84LB2.2 | 75241161 | *Malus x domestica* |
| TPS1 | Q84ZW8.1 | 75149279 | *Zea mays* |

6.2.1 CoA Synthetases and Ligases

The activation of pathway intermediates such as 2-oxopent-3-enoate (1N), 2-hydroxypent-3-enoate (1R), 5-hydroxypent-4-enoate (2I), 2,4-pentadienoate (2J), 3-hydroxypent-4-enoate (2L) can be catalyzed by ADP and AMP-forming CoA ligases (6.2.1). These enzymes can also function in the reverse direction to convert the CoA-derivatives to their acid counterparts as shown in Steps 1Q, 3B, 3I, 3J and 3N.

Several enzymes with broad substrate specificities have been described in the literature. The ADP-forming acetyl-CoA synthetase (ACD, EC 6.2.1.13) from *Archaeoglobus fulgidus*, encoded by AF1211, was shown to operate on a variety of linear and branched-chain substrates including isobutyrate, isopentanoate, and fumarate (Musfeldt et al., J Bacteriol. 184:636-644 (2002)). A second reversible ACD in *Archaeoglobus fulgidus*, encoded by AF1983, was also indicated to have a broad substrate range (Musfeldt et al., supra). The enzyme from *Haloarcula marismortui*, annotated as a succinyl-CoA synthetase, accepts propionate, butyrate, and branched-chain acids (isovalerate and isobutyrate) as substrates, and was shown to operate in the forward and reverse directions (Brasen et al., *Arch. Microbiol* 182:277-287 (2004)). The ACD encoded by PAE3250 from hyperthermophilic crenarchaeon *Pyrobaculum aerophilum* showed the broadest substrate range of all characterized ACDs, reacting with acetyl-CoA, isobutyryl-CoA (preferred substrate) and phenylacetyl-CoA (Brasen and Schonheit, J Arch. Microbiol 182:277-287 (2004)). Directed evolution or engineering can be used to modify this enzyme to operate at the physiological temperature of the host organism. The enzymes from *A. fulgidus*, *H. marismortui* and *P. aerophilum* have all been cloned, functionally expressed, and characterized in *E. coli* (Brasen and Schonheit, Arch. Microbiol 182:277-287 (2004); Musfeldt and Schonheit, J Bacteriol. 184:636-644 (2002)). An additional enzyme is encoded by sucCD in *E. coli*, which naturally catalyzes the formation of succinyl-CoA from succinate with the concomitant consumption of one ATP, a reaction which is reversible in vivo (Buck et al., Biochemistry 24:6245-6252 (1985)). The acyl CoA ligase from *Pseudomonas putida* has been indicated to work on several aliphatic substrates including acetic, propionic, butyric, valeric, hexanoic, heptanoic, and octanoic acids and on aromatic compounds such as phenylacetic and phenoxyacetic acids (Fernandez-Valverde et al., Appl. Environ. Microbiol. 59:1149-1154 (1993)). A related enzyme, malonyl CoA synthetase (6.3.4.9) from *Rhizobium leguminosarum* could convert several diacids, namely, ethyl-, propyl-, allyl-, isopropyl-, dimethyl-, cyclopropyl-, cyclopropylmethylene-, cyclobutyl-, and benzyl-malonate into their corresponding monothioesters (Pohl et al., J. Am. Chem. Soc. 123:5822-5823 (2001)). Recently, a CoA dependent acetyl-CoA ligase was also identified in *Propionibacterium acidipropionici* ATCC 4875 (Parizzi et al., BMC Genomics. 2012; 13: 562., The genome sequence of *Propionibacterium acidipropionici* provides insights into its biotechnological and industrial potential). This enzyme is distinct from the AMP-dependent acetyl-CoA synthetase and is instead related to the ADP-forming succinyl-CoA synthetase complex (SCSC). Genes related to the SCSC (α and β subunits) complex were also found in *Propionibacterium acnes* KPA171202 and *Microlunatus phophovorus* NM-1.

The acylation of acetate to acetyl-CoA is catalyzed by enzymes with acetyl-CoA synthetase activity. Two enzymes that catalyze this reaction are AMP-forming acetyl-CoA synthetase (EC 6.2.1.1) and ADP-forming acetyl-CoA synthetase (EC 6.2.1.13). AMP-forming acetyl-CoA synthetase (ACS) is the predominant enzyme for activation of acetate to acetyl-CoA. Exemplary ACS enzymes are found in *E. coli* (Brown et al., J. Gen. Microbiol 102:327-336 (1977)), *Ralstonia eutropha* (Priefert et al., 174:6590-6599 (1992)), *Methanothermobacter thermautotrophicus* (Ingram-Smith et al., Archaea. 2:95-107 (2007)), *Salmonella enterica* (Gulick et al., 42:2866-2873 (2003)) and *Saccharomyces cerevisiae* (Jogl et al., 43:1425-1431 (2004)).

Methylmalonyl-CoA synthetase from *Rhodopseudomonas palustris* (MatB) converts methylmalonate and malonate to methylmalonyl-CoA and malonyl-CoA, respectively. Structure-based mutagenesis of this enzyme improved CoA synthetase activity with the alternate substrates ethylmalonate and butylmalonate (Crosby et al, AEM, in press (2012)).

| Gene | GenBank Accession No. | GI No. | Organism |
|---|---|---|---|
| AF1211 | NP_070039.1 | 11498810 | *Archaeoglobus fulgidus* |
| AF1983 | NP_070807.1 | 11499565 | *Archaeoglobus fulgidus* |
| Scs | YP_135572.1 | 55377722 | *Haloarcula marismortui* |
| PAE3250 | NP_560604.1 | 18313937 | *Pyrobaculum aerophilum* str. IM2 |
| sucC | NP_415256.1 | 16128703 | *Escherichia coli* |
| sucD | AAC73823.1 | 1786949 | *Escherichia coli* |
| paaF | AAC24333.2 | 22711873 | *Pseudomonas putida* |
| matB | AAC83455.1 | 3982573 | *Rhizobium leguminosarum* |
| Acs | AAC77039.1 | 1790505 | *Escherichia coli* |
| acoE | AAA21945.1 | 141890 | *Ralstonia eutropha* |
| acs1 | ABC87079.1 | 86169671 | *Methanothermobacter thermautotrophicus* |
| acs1 | AAL23099.1 | 16422835 | *Salmonella enterica* |

| Gene | GenBank Accession No. | GI No. | Organism |
|---|---|---|---|
| ACS1 | Q01574.2 | 257050994 | *Saccharomyces cerevisiae* |
| LSC1 | NP_014785 | 6324716 | *Saccharomyces cerevisiae* |
| LSC2 | NP_011760 | 6321683 | *Saccharomyces cerevisiae* |
| bioW | NP_390902.2 | 50812281 | *Bacillus subtilis* |
| bioW | CAA10043.1 | 3850837 | *Pseudomonas mendocina* |
| bioW | P22822.1 | 115012 | *Bacillus sphaericus* |
| PhI | CAJ15517.1 | 77019264 | *Penicillium chrysogenum* |
| phlB | ABS19624.1 | 152002983 | *Penicillium chrysogenum* |
| paaF | AAC24333.2 | 22711873 | *Pseudomonas putida* |
| PACID_02150 | YP_006979420.1 | 410864809 | *Propionibacterium acidipropionici* ATCC 4875 |
| PPA1754 | AAT83483.1 | 50840816 | *Propionibacterium acnes* KPA171202 |
| PPA1755 | AAT83484.1 | 50840817 | *Propionibacterium acnes* KPA171202 |
| Subunit alpha | YP_004571669.1 | 336116902 | *Microlunatus phosphovorus* NM-1 |
| Subunit beta | YP_004571668.1 | 336116901 | *Microlunatus phosphovorus* NM-1 |
| AACS | NP_084486.1 | 21313520 | *Mus musculus* |
| AACS | NP_076417.2 | 31982927 | *Homo sapiens* |

4HB-CoA synthetase catalyzes the ATP-dependent conversion of 4-hydroxybutyrate to 4-hydroxybutyryl-CoA. AMP-forming 4-HB-CoA synthetase enzymes are found in organisms that assimilate carbon via the dicarboxylate/hydroxybutyrate cycle or the 3-hydroxypropionate/4-hydroxybutyrate cycle. Enzymes with this activity have been characterized in *Thermoproteus neutrophilus* and *Metallosphaera sedula* (Ramos-Vera et al, J Bacteriol 192:5329-40 (2010); Berg et al, Science 318:1782-6 (2007)). Others can be inferred by sequence homology.

| Protein | GenBank ID | GI Number | Organism |
|---|---|---|---|
| Tneu_0420 | ACB39368.1 | 170934107 | *Thermoproteus neutrophilus* |
| Caur_0002 | YP_001633649.1 | 163845605 | *Chloroflexus aurantiacus* J-10-fl |
| Cagg_3790 | YP_002465062 | 219850629 | *Chloroflexus aggregans* DSM 9485 |
| Acs | YP_003431745 | 288817398 | *Hydrogenobacter thermophilus* TK-6 |
| PisI_0250 | YP_929773.1 | 119871766 | *Pyrobaculum islandicum* DSM 4184 |
| Msed_1422 | ABP95580.1 | 145702438 | *Metallosphaera sedula* |

3.1.2: CoA Hydrolases

CoA hydrolysis as described in Steps 1Q, 2J and 2I can be catalyzed by CoA hydrolases or thioesterases in the EC class 3.1.2. Additionally, intermediates such as 3-oxo-4-hydroxypentanoyl-CoA, 3,4-dihydroxypentanoyl-CoA, 4-hydroxypent-2-enoyl-COA, 2,4-pentadienoyl-CoA can be converted into their acid counterparts via these enzymes as shown in steps 3B, 3I, 3J, 3N respectively. Several CoA hydrolases with broad substrate ranges are suitable enzymes for hydrolyzing these intermediates. For example, the enzyme encoded by acot12 from *Rattus norvegicus* brain (Robinson et al., *Biochem. Biophys. Res. Commun.* 71:959-965 (1976)) can react with butyryl-CoA, hexanoyl-CoA and malonyl-CoA. The human dicarboxylic acid thioesterase, encoded by acot8, exhibits activity on glutaryl-CoA, adipyl-CoA, suberyl-CoA, sebacyl-CoA, and dodecanedioyl-CoA (Westin et al., *J. Biol. Chem.* 280:38125-38132 (2005)). The closest *E. coli* homolog to this enzyme, tesB, can also hydrolyze a range of CoA thiolesters (Naggert et al., *J Biol Chem* 266:11044-11050 (1991)). A similar enzyme has also been characterized in the rat liver (Deana R., *Biochem Int* 26:767-773 (1992)). Additional enzymes with hydrolase activity in *E. coli* include ybgC, paaI, yciA, and ybdB (Kuznetsova, et al., *FEMS Microbiol Rev,* 2005, 29(2):263-279; Song et al., *J Biol Chem,* 2006, 281(16):11028-38). Though its sequence has not been reported, the enzyme from the mitochondrion of the pea leaf has a broad substrate specificity, with demonstrated activity on acetyl-CoA, propionyl-CoA, butyryl-CoA, palmitoyl-CoA, oleoyl-CoA, succinyl-CoA, and crotonyl-CoA (Zeiher et al., *Plant. Physiol.* 94:20-27 (1990)) The acetyl-CoA hydrolase, ACH1, from *S. cerevisiae* represents another candidate hydrolase (Buu et al., *J. Biol. Chem.* 278:17203-17209 (2003)).

| Gene name | GenBank Accession # | GI# | Organism |
|---|---|---|---|
| acot12 | NP_570103.1 | 18543355 | *Rattus norvegicus* |
| tesB | NP_414986 | 16128437 | *Escherichia coli* |
| acot8 | CAA15502 | 3191970 | *Homo sapiens* |
| acot8 | NP_570112 | 51036669 | *Rattus norvegicus* |
| tesA | NP_415027 | 16128478 | *Escherichia coli* |
| ybgC | NP_415264 | 16128711 | *Escherichia coli* |
| paaI | NP_415914 | 16129357 | *Escherichia coli* |
| ybdB | NP_415129 | 16128580 | *Escherichia coli* |
| ACH1 | NP_009538 | 6319456 | *Saccharomyces cerevisiae* |
| yciA | NP_415769.1 | 16129214 | *Escherichia coli* |
| ydiI | P77781.1 | 13878877 | *Escherichia coli* |
| ybfF | P75736.1 | 2829622 | *Escherichia coli* |

Yet another candidate hydrolase is the glutaconate CoA-transferase from *Acidaminococcus fermentans*. This enzyme was transformed by site-directed mutagenesis into an acyl-CoA hydrolase with activity on glutaryl-CoA, acetyl-CoA and 3-butenoyl-CoA (Mack et al., *FEBS. Lett.* 405:209-212 (1997)). This suggests that the enzymes encoding succinyl-CoA:3-ketoacid-CoA transferases and acetoacetyl-CoA:acetyl-CoA transferases may also serve as candidates for this reaction step but would require certain mutations to change their function.

| Gene name | GenBank Accession # | GI# | Organism |
|---|---|---|---|
| gctA | CAA57199 | 559392 | *Acidaminococcus fermentans* |
| gctB | CAA57200 | 559393 | *Acidaminococcus fermentans* |

Additional hydrolase enzymes include 3-hydroxyisobutyryl-CoA hydrolase which has been described to efficiently catalyze the conversion of 3-hydroxyisobutyryl-CoA to 3-hydroxyisobutyrate during valine degradation (Shimomura et al., *J Biol Chem.* 269:14248-14253 (1994)). Genes encoding this enzyme include hibch of *Rattus norvegicus* (Shimomura et al., *Methods Enzymol.* 324:229-240 (2000)) and *Homo sapiens* (Shimomura et al., supra). Similar gene candidates can also be identified by sequence homology, including hibch of *Saccharomyces cerevisiae* and BC_2292 of *Bacillus cereus*.

| Gene name | GenBank Accession # | GI# | Organism |
|---|---|---|---|
| hibch | Q5XIE6.2 | 146324906 | Rattus norvegicus |
| hibch | Q6NVY1.2 | 146324905 | Homo sapiens |
| hibch | P28817.2 | 2506374 | Saccharomyces cerevisiae |
| BC_2292 | AP09256 | 29895975 | Bacillus cereus |

Methylmalonyl-CoA is converted to methylmalonate by methylmalonyl-CoA hydrolase (EC 3.1.2.7). This enzyme, isolated from Rattus norvegicus liver, is also active on malonyl-CoA and propionyl-CoA as alternative substrates (Kovachy et al., J. Biol. Chem., 258: 11415-11421 (1983)). The gene associated with this enzyme is not known.

2.8.3 CoA Transferase

Several transformations outlined in FIGS. 1, 2 and 3 require a CoA transferase to activate carboxylic acids to their corresponding acyl-CoA derivatives and vice versa. The specific transformations are shown in steps 1N, 1R, 1Q, 2I, 2J, 2L, 3B, 3I, 3J.

CoA transferase enzymes have been described in the open literature and represent suitable candidates for these steps. These are described below. The gene products of cat1, cat2, and cat3 of Clostridium kluyveri have been shown to exhibit succinyl-CoA, 4-hydroxybutyryl-CoA, and butyryl-CoA transferase activity, respectively (Seedorf et al., Proc. Natl. Acad. Sci U.S.A 105:2128-2133 (2008); Sohling et al., J Bacteriol. 178:871-880 (1996)). Similar CoA transferase activities are also present in Trichomonas vaginalis, Trypanosoma brucei, Clostridium aminobutyricum and Porphyromonas gingivalis (Riviere et al., J. Biol. Chem. 279: 45337-45346 (2004); van Grinsven et al., J. Biol. Chem. 283:1411-1418 (2008)).

| Protein | GenBank ID | GI Number | Organism |
|---|---|---|---|
| cat1 | P38946.1 | 729048 | Clostridium kluyveri |
| cat2 | P38942.2 | 172046066 | Clostridium kluyveri |
| cat3 | EDK35586.1 | 146349050 | Clostridium kluyveri |
| TVAG_395550 | XP_001330176 | 123975034 | Trichomonas vaginalis G3 |
| Tb11.02.0290 | XP_828352 | 71754875 | Trypanosoma brucei |
| cat2 | CAB60036.1 | 6249316 | Clostridium aminobutyricum |
| cat2 | NP_906037.1 | 34541558 | Porphyromonas gingivalis W83 |

A fatty acyl-CoA transferase that utilizes acetyl-CoA as the CoA donor is acetoacetyl-CoA transferase, encoded by the E. coli atoA (alpha subunit) and atoD (beta subunit) genes (Korolev et al., Acta Crystallogr. D. Biol. Crystallogr. 58:2116-2121 (2002); Vanderwinkel et al., 33:902-908 (1968)). This enzyme has a broad substrate range on substrates of chain length C3-C6 (Sramek et al., Arch Biochem Biophys 171:14-26 (1975)) and has been shown to transfer the CoA moiety to acetate from a variety of branched and linear 3-oxo and acyl-CoA substrates, including isobutyrate (Matthies et al., Appl Environ. Microbiol 58:1435-1439 (1992)), valerate (Vanderwinkel et al., Biochem. Biophys. Res. Commun. 33:902-908 (1968)) and butanoate (Vanderwinkel et al., Biochem. Biophys. Res. Commun. 33:902-908 (1968)). This enzyme is induced at the transcriptional level by acetoacetate, so modification of regulatory control may be necessary for engineering this enzyme into a pathway (Pauli et al., Eur. J Biochem. 29:553-562 (1972)). Similar enzymes exist in Corynebacterium glutamicum ATCC 13032 (Duncan et al., 68:5186-5190 (2002)), Clostridium acetobutylicum (Cary et al., Appl Environ Microbiol 56:1576-1583 (1990); Wiesenborn et al., Appl Environ Microbiol 55:323-329 (1989)), and Clostridium saccharoperbutylacetonicum (Kosaka et al., Biosci. Biotechnol Biochem. 71:58-68 (2007)).

| Gene | GI # | Accession No. | Organism |
|---|---|---|---|
| atoA | 2492994 | P76459.1 | Escherichia coli |
| atoD | 2492990 | P76458.1 | Escherichia coli |
| actA | 62391407 | YP_226809.1 | Corynebacterium glutamicum |
| cg0592 | 62389399 | YP_224801.1 | Corynebacterium glutamicum |
| ctfA | 15004866 | NP_149326.1 | Clostridium acetobutylicum |
| ctfB | 15004867 | NP_149327.1 | Clostridium acetobutylicum |
| ctfA | 31075384 | AAP42564.1 | Clostridium saccharoperbutylacetonicum |
| ctfB | 31075385 | AAP42565.1 | Clostridium saccharoperbutylacetonicum |

4.1.1 Decarboxylase

Exemplary enzymes for catalyzing the decarboxylation of 2,4-pentadienoate (1H, 2G, 3L), 4-hydroxypent-2-enoate (1T), 5-hydroxypent-2-enoate (2P) and 4-hydroxypent-2-enoate (3E) are sorbic acid decarboxylase, aconitate decarboxylase, 4-oxalocrotonate decarboxylase and cinnamate decarboxylase.

Sorbic acid decarboxylase converts sorbic acid to 1,3-pentadiene. Sorbic acid decarboxylation by Aspergillus niger requires three genes: padA1, ohbA1, and sdrA (Plumridge et al. Fung. Genet. Bio, 47:683-692 (2010). PadA1 is annotated as a phenylacrylic acid decarboxylase, ohbA1 is a putative 4-hydroxybenzoic acid decarboxylase, and sdrA is a sorbic acid decarboxylase regulator. Additional species have also been shown to decarboxylate sorbic acid including several fungal and yeast species (Kinderlerler and Hatton, Food Addit Contam., 7(5):657-69 (1990); Casas et al., Int J Food Micro., 94(1):93-96 (2004); Pinches and Apps, Int. J. Food Microbiol. 116: 182-185 (2007)). For example, Aspergillus oryzae and Neosartorya fischeri have been shown to decarboxylate sorbic acid and have close homologs to padA1, ohbA1, and sdrA.

| Gene name | GenBankID | GI Number | Organism |
|---|---|---|---|
| padA1 | XP_001390532.1 | 145235767 | Aspergillus niger |
| ohbA1 | XP_001390534.1 | 145235771 | Aspergillus niger |
| sdrA | XP_001390533.1 | 145235769 | Aspergillus niger |
| padA1 | XP_001818651.1 | 169768362 | Aspergillus oryzae |
| ohbA1 | XP_001818650.1 | 169768360 | Aspergillus oryzae |
| sdrA | XP_001818649.1 | 169768358 | Aspergillus oryzae |
| padA1 | XP_001261423.1 | 119482790 | Neosartorya fischeri |
| ohbA1 | XP_001261424.1 | 119482792 | Neosartorya fischeri |
| sdrA | XP_001261422.1 | 119482788 | Neosartorya fischeri |

Aconitate decarboxylase (EC 4.1.1.6) catalyzes the final step in itaconate biosynthesis in a strain of Candida and also in the filamentous fungus Aspergillus terreus (Bonnarme et al. J Bacteriol. 177:3573-3578 (1995); Willke and Vorlop, Appl Microbiol. Biotechnol 56:289-295 (2001)). A cis-aconitate decarboxylase (CAD) (EC 4.1.16) has been purified and characterized from Aspergillus terreus (Dwiarti et al., J. Biosci. Bioeng. 94(1): 29-33 (2002)). Recently, the gene has been cloned and functionally characterized (Kanamasa et al., Appl. Microbiol Biotechnol 80:223-229 (2008)) and (WO/2009/014437). Several close homologs of CAD are listed below (EP 2017344A1; WO 2009/014437 A1). The gene and protein sequence of CAD were reported previously (EP 2017344 A1; WO 2009/014437 A1), along with several close homologs listed in the table below.

| Gene name | GenBankID | GI Number | Organism |
| --- | --- | --- | --- |
| CAD | XP_001209273 | 115385453 | *Aspergillus terreus* |
| | XP_001217495 | 115402837 | *Aspergillus terreus* |
| | XP_001209946 | 115386810 | *Aspergillus terreus* |
| | BAE66063 | 83775944 | *Aspergillus oryzae* |
| | XP_001393934 | 145242722 | *Aspergillus niger* |
| | XP_391316 | 46139251 | *Gibberella zeae* |
| | XP_001389415 | 145230213 | *Aspergillus niger* |
| | XP_001383451 | 126133853 | *Pichia stipitis* |
| | YP_891060 | 118473159 | *Mycobacterium smegmatis* |
| | NP_961187 | 41408351 | *Mycobacterium avium* subsp. *pratuberculosis* |
| | YP_880968 | 118466464 | *Mycobacterium avium* |
| | ZP_01648681 | 119882410 | *Salinispora arenicola* |

An additional class of decarboxylases has been characterized that catalyze the conversion of cinnamate (phenylacrylate) and substituted cinnamate derivatives to the corresponding styrene derivatives. These enzymes are common in a variety of organisms and specific genes encoding these enzymes that have been cloned and expressed in *E. coli* are: pad1 from *Saccharomyces cerevisae* (Clausen et al., Gene 142:107-112 (1994)), pdc from *Lactobacillus plantarum* (Barthelmebs et al., 67:1063-1069 (2001); Qi et al., Metab Eng 9:268-276 (2007); Rodriguez et al., J. Agric. Food Chem. 56:3068-3072 (2008)), pofK (pad) from *Klebsiella oxytoca* (Uchiyama et al., Biosci. Biotechnol. Biochem. 72:116-123 (2008); Hashidoko et al., Biosci. Biotech. Biochem. 58:217-218 (1994)), Pedicoccus *pentosaceus* (Barthelmebs et al., 67:1063-1069 (2001)), and padC from *Bacillus subtilis* and *Bacillus pumilus* (Shingler et al., 174: 711-724 (1992)). A ferulic acid decarboxylase from *Pseudomonas fluorescens* also has been purified and characterized (Huang et al., J. Bacteriol. 176:5912-5918 (1994)). Importantly, this class of enzymes have been shown to be stable and do not require either exogenous or internally bound co-factors, thus making these enzymes ideally suitable for biotransformations (Sariaslani, Annu. Rev. Microbiol. 61:51-69 (2007)).

| Protein | GenBank ID | GI Number | Organism |
| --- | --- | --- | --- |
| pad1 | AAB64980.1 | 1165293 | *Saccharomyces cerevisae* |
| ohbA1 | BAG32379.1 | 188496963 | *Saccharomyces cerevisiae* |
| pdc | AAC45282.1 | 1762616 | *Lactobacillus plantarum* |
| pad | BAF65031.1 | 149941608 | *Klebsiella oxytoca* |
| padC | NP_391320.1 | 16080493 | *Bacillus subtilis* |
| pad | YP_804027.1 | 116492292 | *Pedicoccus pentosaceus* |
| pad | CAC18719.1 | 11691810 | *Bacillus pumilus* |

4-Oxalocronate decarboxylase catalyzes the decarboxylation of 4-oxalocrotonate to 2-oxopentanoate. This enzyme has been isolated from numerous organisms and characterized. The decarboxylase typically functions in a complex with vinylpyruvate hydratase. Genes encoding this enzyme include dmpH and dmpE in *Pseudomonas* sp. (strain 600) (Shingler et al., 174:711-724 (1992)), xylII and xylIII from *Pseudomonas putida* (Kato et al., Arch. Microbiol 168:457-463 (1997); Stanley et al., Biochemistry 39:3514 (2000); Lian et al., J. Am. Chem. Soc. 116:10403-10411 (1994)) and Reut_B5691 and Reut_B5692 from *Ralstonia eutropha* JMP134 (Hughes et al., J Bacteriol, 158:79-83 (1984)). The genes encoding the enzyme from *Pseudomonas* sp. (strain 600) have been cloned and expressed in *E. coli* (Shingler et al., J. Bacteriol. 174:711-724 (1992)). The 4-oxalocrotonate decarboxylase encoded by xylII in *Pseudomonas putida* functions in a complex with vinylpyruvate hydratase. A recombinant form of this enzyme devoid of the hydratase activity and retaining wild type decarboxylase activity has been characterized (Stanley et al., Biochem. 39:718-26 (2000)). A similar enzyme is found in *Ralstonia pickettii* (formerly *Pseudomonas pickettii*) (Kukor et al., J Bacteriol. 173:4587-94 (1991)).

| Gene | GenBank | GI Number | Organism |
| --- | --- | --- | --- |
| dmpH | CAA43228.1 | 45685 | *Pseudomonas* sp. CF600 |
| dmpE | CAA43225.1 | 45682 | *Pseudomonas* sp. CF600 |
| xylII | YP_709328.1 | 111116444 | *Pseudomonas putida* |
| xylIII | YP_709353.1 | 111116469 | *Pseudomonas putida* |
| Reut_B5691 | YP_299880.1 | 73539513 | *Ralstonia eutropha* JMP134 |
| Reut_B5692 | YP_299881.1 | 73539514 | *Pseudomonas putida* JMP134 |
| xylI | P49155.1 | 1351446 | *Pseudomonas putida* |
| tbuI | YP_002983475.1 | 241665116 | *Ralstonia pickettii* |
| nbaG | BAC65309.1 | 28971626 | *Pseudomonas fluorescens* KU-7 |

Numerous characterized enzymes decarboxylate amino acids and similar compounds, including aspartate decarboxylase, lysine decarboxylase and ornithine decarboxylase. Aspartate decarboxylase (EC 4.1.1.11) decarboxylates aspartate to form beta-alanine. This enzyme participates in pantothenate biosynthesis and is encoded by gene panD in *Escherichia coli* (Dusch et al., Appl. Environ. Microbiol 65:1530-1539 (1999); Ramjee et al., Biochem. J 323 (Pt 3):661-669 (1997); Merkel et al., FEMS Microbiol Lett. 143:247-252 (1996); Schmitzberger et al., EMBO J 22:6193-6204 (2003)). The enzymes from *Mycobacterium tuberculosis* (Chopra et al., Protein Expr. Purif. 25:533-540 (2002)) and *Corynebacterium glutanicum* (Dusch et al., Appl. Environ. Microbiol 65:1530-1539 (1999)) have been expressed and characterized in *E. coli*.

| Protein | GenBank ID | GI Number | Organism |
| --- | --- | --- | --- |
| panD | P0A790 | 67470411 | *Escherichia coli* K12 |
| panD | Q9X4N0 | 18203593 | *Corynebacterium glutanicum* |
| panD | P65660.1 | 54041701 | *Mycobacterium tuberculosis* |

Lysine decarboxylase (EC 4.1.1.18) catalyzes the decarboxylation of lysine to cadaverine. Two isozymes of this enzyme are encoded in the *E. coli* genome by genes cadA and ldcC. CadA is involved in acid resistance and is subject to positive regulation by the cadC gene product (Lemonnier et al., Microbiology 144 (Pt 3):751-760 (1998)). CadC accepts hydroxylysine and S-aminoethylcysteine as alternate substrates, and 2-aminopimelate and 6-aminocaproate act as competitive inhibitors to this enzyme (Sabo et al., Biochemistry 13:662-670 (1974)). The constitutively expressed ldc gene product is less active than CadA (Lemonnier and Lane, Microbiology 144 (Pt 3):751-760 (1998)). A lysine decarboxylase analogous to CadA was recently identified in *Vibrio parahaemolyticus* (Tanaka et al., J Appl Microbiol 104:1283-1293 (2008)). The lysine decarboxylase from *Selenomonas ruminantium*, encoded by ldc, bears sequence similarity to eukaryotic ornithine decarboxylases, and accepts both L-lysine and L-ornithine as substrates (Takatsuka et al., Biosci. Biotechnol Biochem. 63:1843-

1846 (1999)). Active site residues were identified and engineered to alter the substrate specificity of the enzyme (Takatsuka et al., J Bacteriol. 182:6732-6741 (2000)). Several ornithine decarboxylase enzymes (EC 4.1.1.17) also exhibit activity on lysine and other similar compounds. Such enzymes are found in *Nicotiana glutinosa* (Lee et al., Biochem. J 360:657-665 (2001)), *Lactobacillus* sp. 30a (Guirard et al., J Biol. Chem. 255:5960-5964 (1980)) and *Vibrio vulnificus* (Lee et al., J Biol. Chem. 282:27115-27125 (2007)). The enzymes from *Lactobacillus* sp. 30a (Momany et al., J Mol. Biol. 252:643-655 (1995)) and *V. vulnificus* have been crystallized. The *V. vulnificus* enzyme efficiently catalyzes lysine decarboxylation and the residues involved in substrate specificity have been elucidated (Lee et al., J Biol. Chem. 282:27115-27125 (2007)). A similar enzyme has been characterized in *Trichomonas vaginalis* but the gene encoding this enzyme is not known (Yarlett et al., Biochem. J 293 (Pt 2):487-493 (1993)).

| Protein | GenBank ID | GI Number | Organism |
|---|---|---|---|
| cadA | AAA23536.1 | 145458 | *Escherichia coli* |
| ldcC | AAC73297.1 | 1786384 | *Escherichia coli* |
| Ldc | O50657.1 | 13124043 | *Selenomonas ruminantium* |
| cadA | AB124819.1 | 44886078 | *Vibrio parahaemolyticus* |
| AF323910.1:1 . . . 1299 | AAG45222.1 | 12007488 | *Nicotiana glutinosa* |
| odc1 | P43099.2 | 1169251 | *Lactobacillus* sp. 30a |
| VV2_1235 | NP_763142.1 | 27367615 | *Vibrio vulnificus* |

An exemplary carboxy-lyase for decarboxylating 2-hydroxypent-3-enoate (1S) is acetolactate decarboxylase (4.1.1.5) which participates in citrate catabolism and branched-chain amino acid biosynthesis, converting the 2-hydroxyacid, 2-acetolactate, to acetoin. In *Lactococcus lactis* the enzyme is composed of six subunits, encoded by gene aldB, and is activated by valine, leucine and isoleucine (Goupil-Feuillerat et al., J. Bacteriol. 182:5399-5408 (2000); Goupil et al., Appl. Environ. Microbiol. 62:2636-2640 (1996)). This enzyme has been overexpressed and characterized in *E. coli* (Phalip et al., FEBS Lett. 351:95-99 (1994); Nielsen et al, Biotechnol J 5:274-84 (2010)). In other organisms the enzyme is a dimer, encoded by aldC in *Streptococcus thermophilus* (Monnet et al., Lett. Appl. Microbiol. 36:399-405 (2003)), aldB in *Bacillus brevis* (Najmudin et al., Acta Crystallogr. D. Biol. Crystallogr. 59:1073-1075 (2003); Diderichsen et al., J. Bacteriol. 172: 4315-4321 (1990)) and budA from *Enterobacter aerogenes* (Diderichsen et al., J. Bacteriol. 172:4315-4321 (1990)). The enzyme from *Bacillus brevis* was cloned and overexpressed in *Bacillus subtilis* and characterized crystallographically (Najmudin et al., Acta Crystallogr. D. Biol. Crystallogr. 59:1073-1075 (2003)). The *Acetobacter aceti* acetolactate decarboxylase was cloned and heterologously expressed in brewer's yeast (Yamano et al, J Biotechnol 32:165-71 (1994)). Additionally, the enzyme from *Leuconostoc lactis* has been purified and characterized but the gene has not been isolated (O'Sullivan et al., FEMS Microbiol. Lett. 194:245-249 (2001)).

| Gene name | GenBank Accession # | GI# | Organism |
|---|---|---|---|
| aldB | AAB81923.1 | 2565161 | *Lactococcus lactis* |
| aldC | Q8L208 | | *Streptococcus thermophilus* |
| aldB | P23616 | | *Bacillus brevis* |
| budA | P05361 | | *Enterobacter aerogenes* |
| aldc | AAC60472.1 | 545933 | *Acetobacter aceti* |

Tartrate decarboxylase (EC 4.1.1.73) carries out an alpha, beta-hydroxyacid decarboxylation reaction. The enzyme, characterized in *Pseudomonas* sp. group Ve-2, is NAD+ dependent and catalyzes coupled oxidation-reduction reaction that proceeds through an oxaloglycolate intermediate (Furuyoshi et al., J Biochem. 110:520-525 (1991)). A side reaction catalyzed by this enzyme is the NAD+ dependent oxidation of tartrate (1% of activity). A gene has not been associated with this enzyme activity to date.

The decarboxylation of keto-acids such as 4-hydroxy 2-oxovalerate, 2-oxopent-3-enoate as shown in Steps 1C and 1I is catalyzed by a variety of enzymes with varied substrate specificities, including pyruvate decarboxylase (EC 4.1.1.1), benzoylformate decarboxylase (EC 4.1.1.7), alpha-ketoglutarate decarboxylase and branched-chain alpha-ketoacid decarboxylase. Pyruvate decarboxylase (PDC), also termed keto-acid decarboxylase, is a key enzyme in alcoholic fermentation, catalyzing the decarboxylation of pyruvate to acetaldehyde. The enzyme from *Saccharomyces cerevisiae* has a broad substrate range for aliphatic 2-keto acids including 2-ketobutyrate, 2-ketovalerate, 3-hydroxypyruvate and 2-phenylpyruvate (22). This enzyme has been extensively studied, engineered for altered activity, and functionally expressed in *E. coli* (Killenberg-Jabs et al., Eur. J. Biochem. 268:1698-1704 (2001); Li et al., Biochemistry. 38:10004-10012 (1999); ter Schure et al., Appl. Environ. Microbiol. 64:1303-1307 (1998)). The PDC from *Zymomonas mobilis*, encoded by pdc, also has a broad substrate range and has been a subject of directed engineering studies to alter the affinity for different substrates (Siegert et al., Protein Eng Des Sel 18:345-357 (2005)). The crystal structure of this enzyme is available (Killenberg-Jabs et al., Eur. J. Biochem. 268:1698-1704 (2001)). Other well-characterized PDC candidates include the enzymes from *Acetobacter pasteurians* (Chandra et al., 176:443-451 (2001)) and *Kluyveromyces lactis* (Krieger et al., 269:3256-3263 (2002)).

| Protein | GenBank ID | GI Number | Organism |
|---|---|---|---|
| pdc | P06672.1 | 118391 | *Zymomonas mobilis* |
| pdc1 | P06169 | 30923172 | *Saccharomyces cerevisiae* |
| pdc | Q8L388 | 20385191 | *Acetobacter pasteurians* |
| pdc1 | Q12629 | 52788279 | *Kluyveromyces lactis* |

Like PDC, benzoylformate decarboxylase (EC 4.1.1.7) has a broad substrate range and has been the target of enzyme engineering studies. The enzyme from *Pseudomonas putida* has been extensively studied and crystal structures of this enzyme are available (Polovnikova et al., 42:1820-1830 (2003); Hasson et al., 37:9918-9930 (1998)). Site-directed mutagenesis of two residues in the active site of the *Pseudomonas putida* enzyme altered the affinity (Km) of naturally and non-naturally occurring substrates (Siegert et al., Protein Eng Des Sel 18:345-357 (2005)). The properties of this enzyme have been further modified by directed engineering (Lingen et al., Chembiochem. 4:721-726 (2003); Lingen et al., Protein Eng 15:585-593 (2002)). The enzyme from *Pseudomonas aeruginosa*, encoded by mdlC, has also been characterized experimentally (Barrowman et al., 34:57-60 (1986)). Additional gene candidates from *Pseudomonas stutzeri, Pseudomonas fluorescens* and other organisms can be inferred by sequence homology or identified using a growth selection system developed in *Pseudomonas putida* (Henning et al., Appl. Environ. Microbiol. 72:7510-7517 (2006)).

| Protein | GenBank ID | GI Number | Organism |
| --- | --- | --- | --- |
| mdlC | P20906.2 | 3915757 | *Pseudomonas putida* |
| mdlC | Q9HUR2.1 | 81539678 | *Pseudomonas aeruginosa* |
| dpgB | ABN80423.1 | 126202187 | *Pseudomonas stutzeri* |
| ilvB-1 | YP_260581.1 | 70730840 | *Pseudomonas fluorescens* |

A third enzyme capable of decarboxylating 2-oxoacids is alpha-ketoglutarate decarboxylase (KGD, EC 4.1.1.71). The substrate range of this class of enzymes has not been studied to date. An exemplary KDC is encoded by kgd in *Mycobacterium tuberculosis* (Tian et al., PNAS 102:10670-10675 (2005)). KDC enzyme activity has also been detected in several species of rhizobia including *Bradyrhizobium japonicum* and *Mesorhizobium loti* (Green et al., J Bacteriol 182:2838-2844 (2000)). Although the KDC-encoding gene(s) have not been isolated in these organisms, the genome sequences are available and several genes in each genome are annotated as putative KDCs. A KDC from *Euglena gracilis* has also been characterized but the gene associated with this activity has not been identified to date (Shigeoka et al., Arch. Biochem. Biophys. 288:22-28 (1991)). The first twenty amino acids starting from the N-terminus were sequenced MTYKAPVKDVKFLLDK-VFKV (Shigeoka and Nakano, Arch. Biochem. Biophys. 288:22-28 (1991)). The gene could be identified by testing candidate genes containing this N-terminal sequence for KDC activity.

| Protein | GenBank ID | GI Number | Organism |
| --- | --- | --- | --- |
| kgd | O50463.4 | 160395583 | *Mycobacterium tuberculosis* |
| kgd | NP_767092.1 | 27375563 | *Bradyrhizobium japonicum* USDA110 |
| kgd | NP_105204.1 | 13473636 | *Mesorhizobium loti* |

A fourth candidate enzyme for catalyzing this reaction is branched chain alpha-ketoacid decarboxylase (BCKA). This class of enzyme has been shown to act on a variety of compounds varying in chain length from 3 to 6 carbons (Oku et al., J Biol Chem. 263:18386-18396 (1988); Smit et al., Appl Environ Microbiol 71:303-311 (2005)). The enzyme in *Lactococcus lactis* has been characterized on a variety of branched and linear substrates including 2-oxobutanoate, 2-oxohexanoate, 2-oxopentanoate, 3-methyl-2-oxobutanoate, 4-methyl-2-oxobutanoate and isocaproate (Smit et al., Appl Environ Microbiol 71:303-311 (2005)). The enzyme has been structurally characterized (Berg et al., Science. 318:1782-1786 (2007)). Sequence alignments between the *Lactococcus lactis* enzyme and the pyruvate decarboxylase of *Zymomonas mobilus* indicate that the catalytic and substrate recognition residues are nearly identical (Siegert et al., Protein Eng Des Sel 18:345-357 (2005)), so this enzyme would be a promising candidate for directed engineering. Decarboxylation of alpha-ketoglutarate by a BCKA was detected in *Bacillus subtilis*; however, this activity was low (5%) relative to activity on other branched-chain substrates (Oku and Kaneda, J Biol Chem. 263:18386-18396 (1988)) and the gene encoding this enzyme has not been identified to date. Additional BCKA gene candidates can be identified by homology to the *Lactococcus lactis* protein sequence. Many of the high-scoring BLASTp hits to this enzyme are annotated as indolepyruvate decarboxylases (EC 4.1.1.74). Indolepyruvate decarboxylase (IPDA) is an enzyme that catalyzes the decarboxylation of indolepyruvate to indoleacetaldehyde in plants and plant bacteria. Recombinant branched chain alpha-keto acid decarboxylase enzymes derived from the E1 subunits of the mitochondrial branched-chain keto acid dehydrogenase complex from *Homo sapiens* and *Bos taurus* have been cloned and functionally expressed in *E. coli* (Davie et al., J. Biol. Chem. 267:16601-16606 (1992); Wynn et al., J. Biol. Chem. 267:12400-12403 (1992); Wynn et al., J. Biol. Chem. 267:1881-1887 (1992)). In these studies, the authors found that co-expression of chaperonins GroEL and GroES enhanced the specific activity of the decarboxylase by 500-fold (Wynn et al., J. Biol. Chem. 267:12400-12403 (1992)). These enzymes are composed of two alpha and two beta subunits.

| Protein | GenBank ID | GI Number | Organism |
| --- | --- | --- | --- |
| kdcA | AAS49166.1 | 44921617 | *Lactococcus lactis* |
| kdc | P9WG37.1 | 614088617 | *Mycobacterium tuberculosis* BcG H37Rv |
| BCKDHB | NP_898871.1 | 34101272 | *Homo sapiens* |
| BCKDHA | NP_000700.1 | 11386135 | *Homo sapiens* |
| BCKDHB | P21839 | 115502434 | *Bos taurus* |
| BCKDHA | P11178 | 129030 | *Bos taurus* |

The acetolactate synthase from *Bacillus subtilis* (AlsS), which naturally catalyzes the condensation of two molecules of pyruvate to form 2-acetolactate, is also able to catalyze the decarboxylation of 2-ketoisovalerate like KDC both in vivo and in vitro [PMID=19684168].

4.2.1 Dehydratase

The dehydration of 2-hydroxypent-3-enoyl-CoA (1P), 3-hydroxypent-4-enoyl-CoA (2O), 3,4-dihydroxypentanoyl-CoA (3H), 4-hydroxy pent-2-enoyl-CoA (3M) and 5-hydroxypent-2-enoyl-CoA (2N) can be catalyzed by a special class of oxygen-sensitive enzymes that dehydrate 2-hydroxyacyl-CoA derivatives by a radical-mechanism (Buckel and Golding, *Annu. Rev. Microbiol.* 60:27-49 (2006); Buckel et al., *Curr. Opin. Chem. Biol.* 8:462-467 (2004); Buckel et al., *Biol. Chem.* 386:951-959 (2005); Kim et al., *FEBS J.* 272:550-561 (2005); Kim et al., *FEMS Microbiol. Rev.* 28:455-468 (2004); Zhang et al., Microbiology 145 (Pt 9):2323-2334 (1999)). One example of such an enzyme is the lactyl-CoA dehydratase from *Clostridium propionicum*, which catalyzes the dehydration of lactoyl-CoA to form acryloyl-CoA (Kuchta and Abeles, *J. Biol. Chem.* 260: 13181-13189 (1985); Hofmeister and Buckel, *Eur. J. Biochem.* 206:547-552 (1992)). An additional example is 2-hydroxyglutaryl-CoA dehydratase encoded by hgdABC from *Acidaminococcus fermentans* (Mueller and Buckel, *Eur. J. Biochem.* 230:698-704 (1995); Schweiger et al., *Eur. J. Biochem.* 169:441-448 (1987)). Purification of the dehydratase from *A. fermentans* yielded two components, A and D. Component A (HgdC) acts as an activator or initiator of dehydration. Component D is the actual dehydratase and is encoded by HgdAB. Variations of this enzyme have been found in *Clostridium symbiosum* and *Fusobacterium nucleatum*. Component A, the activator, from *A. fermentans* is active with the actual dehydratse (component D) from *C. symbiosum* and is reported to have a specific activity of 60 per second, as compared to 10 per second with the component D from *A. fermentans*. Yet another example is the 2-hydroxyisocaproyl-CoA dehydratase from *Clostridium difficile* catalyzed by hadBC and activated by hadI (Darley et al., *FEBS J.* 272:550-61 (2005)). The sequence of the complete *C. propionicium* lactoyl-CoA dehydratase is not yet listed in publicly available databases. However, the sequence of the beta-subunit corresponds to the GenBank accession number AJ276553 (Selmer et al, *Eur J Biochem,* 269:372-80 (2002)). The dehydratase from *Clostridium sporogens* that dehydrates phenyllactyl-CoA to cinnamoyl-CoA is also a potential candidate for this step. This enzyme is composed of three subunits, one of which is a CoA transferase. The first step comprises of a CoA transfer from cinnamoyl-CoA to phenyllactate leading to the formation of phenyllactyl-CoA and cinnamate. The product cinnamate is released. The dehydratase then converts phenyllactyl-CoA into cinnamoyl-CoA. FldA is the CoA transferase and FldBC are related to the alpha and beta subunits of the dehydratase, component D, from *A. fermentans*.

| Gene | GenBank Accession No. | GI No. | Organism |
| --- | --- | --- | --- |
| hgdA | P11569 | 296439332 | *Acidaminococcus fermentans* |
| hgdB | P11570 | 296439333 | *Acidaminococcus fermentans* |
| hgdC | P11568 | 2506909 | *Acidaminococcus fermentans* |
| hgdA | AAD31676.1 | 4883832 | *Clostridum symbiosum* |
| hgdB | AAD31677.1 | 4883833 | *Clostridum symbiosum* |
| hgdC | AAD31675.1 | 4883831 | *Clostridum symbiosum* |
| hgdA | EDK88042.1 | 148322792 | *Fusobacterium nucleatum* |
| hgdB | EDK88043.1 | 148322793 | *Fusobacterium nucleatum* |
| hgdC | EDK88041.1 | 148322791 | *Fusobacterium nucleatum* |
| FldB | Q93AL9.1 | 75406928 | *Clostridium sporogens* |
| FldC | Q93AL8.1 | 75406927 | *Clostridium sporogens* |
| hadB | YP_001086863 | 126697966 | *Clostridium difficile* |
| hadC | YP_001086864 | 126697967 | *Clostridium difficile* |
| hadI | YP_001086862 | 126697965 | *Clostridium difficile* |
| lcdB | AJ276553 | 7242547 | *Clostridium propionicum* |

Another dehydratase that can potentially conduct such a biotransformation is the enoyl-CoA hydratase (4.2.1.17) of *Pseudomonas putida*, encoded by ech that catalyzes the conversion of 3-hydroxybutyryl-CoA to crotonyl-CoA (Roberts et al., *Arch. Microbiol* 117:99-108 (1978)). This transformation is also catalyzed by the crt gene product of *Clostridium acetobutylicum*, the crt1 gene product of *C. kluyveri*, and other clostridial organisms Atsumi et al., *Metab Eng* 10:305-311 (2008); Boynton et al., *J Bacteriol.* 178:3015-3024 (1996); Hillmer et al., *FEBS Lett.* 21:351-354 (1972)). Additional enoyl-CoA hydratase candidates are phaA and phaB, of *P. putida*, and paaA and paaB from *P. fluorescens* (Olivera et al., *Proc. Natl. Acad. Sci U.S.A* 95:6419-6424 (1998)). The gene product of pimF in *Rhodopseudomonas palustris* is predicted to encode an enoyl-CoA hydratase that participates in pimeloyl-CoA degradation (Harrison et al., *Microbiology* 151:727-736 (2005)). Lastly, a number of *Escherichia coli* genes have been shown to demonstrate enoyl-CoA hydratase functionality including maoC (Park et al., *J Bacteriol.* 185:5391-5397 (2003)), paaF (Ismail et al., *Eur. J Biochem.* 270:3047-3054 (2003); Park et al., *Appl. Biochem. Biotechnol* 113-116:335-346 (2004); Park et al., *Biotechnol Bioeng* 86:681-686 (2004)) and paaG (Ismail et al., *Eur. J Biochem.* 270:3047-3054 (2003); Park and Lee, *Appl. Biochem. Biotechnol* 113-116:335-346 (2004); Park and Yup, *Biotechnol Bioeng* 86:681-686 (2004)).

| Gene | GenBank Accession No. | GI No. | Organism |
| --- | --- | --- | --- |
| ech | NP_745498.1 | 26990073 | *Pseudomonas putida* |
| crt | NP_349318.1 | 15895969 | *Clostridium acetobutylicum* |
| crt1 | YP_001393856 | 153953091 | *Clostridium kluyveri* |
| phaA | NP_745427.1 | 26990002 | *Pseudomonas putida* KT2440 |
| phaB | NP_745426.1 | 26990001 | *Pseudomonas putida* KT2440 |
| paaA | ABF82233.1 | 106636093 | *Pseudomonas fluorescens* |
| paaB | ABF82234.1 | 106636094 | *Pseudomonas fluorescens* |
| maoC | NP_415905.1 | 16129348 | *Escherichia coli* |
| paaF | NP_415911.1 | 16129354 | *Escherichia coli* |
| paaG | NP_415912.1 | 16129355 | *Escherichia coli* |

Alternatively, the *E. coli* gene products of fadA and fadB encode a multienzyme complex involved in fatty acid oxidation that exhibits enoyl-CoA hydratase activity (Yang et al., *Biochemistry* 30:6788-6795 (1991); Yang, *J Bacteriol.* 173:7405-7406 (1991); Nakahigashi et al., *Nucleic Acids Res.* 18:4937 (1990)). Knocking out a negative regulator encoded by fadR can be utilized to activate the fadB gene product (Sato et al., *J Biosci. Bioeng* 103:38-44 (2007)). The fadI and fadJ genes encode similar functions and are naturally expressed under anaerobic conditions (Campbell et al., *Mol. Microbiol* 47:793-805 (2003)).

| Protein | GenBank ID | GI Number | Organism |
| --- | --- | --- | --- |
| fadA | YP_026272.1 | 49176430 | *Escherichia coli* |
| fadB | NP_418288.1 | 16131692 | *Escherichia coli* |
| fadI | NP_416844.1 | 16130275 | *Escherichia coli* |
| fadJ | NP_416843.1 | 16130274 | *Escherichia coli* |
| fadR | NP_415705.1 | 16129150 | *Escherichia coli* |

The dehydration of crotyl alcohol (1M, 4H), methyl vinyl carbinol (1L, 2Q, 3F, 4G), 3-hydroxybutyraldehyde (1D), 4-hydroxy-2-oxovalerate (1E, 2C), 2-hydroxy pent3-enoate (1G), 4-hydroxypent-2-enoate (1V, 3K), 5-hydroxypent-2-enoate (2F), 3-hydroxypent-4-enoate (2R) and 3,4-dihydroxypentanoate (3D) can be catalyzed exemplary dehydratases including oleate hydratase, acyclic 1,2-hydratase, linalool dehydratase, dimethylmaleate hydratase, (S)-2-methylmalate dehydratase, fumarate hydratase, glycerol dehydratase and enoyl-CoA hydratase enzymes. Enzyme candidates are described below.

Alternatively, crotyl alcohol, 3-buten-2-ol and 3-buten-1-ol produced by culturing the non-naturally occurring microbial organisms described herein can be converted to butadiene by chemical dehydration in the presence of a chemical catalyst. For example see international patent application publication WO2012106516A1.

Oleate hydratases catalyze the reversible hydration of non-activated alkenes to their corresponding alcohols. Oleate hydratase enzymes disclosed in WO2011/076691 and WO 2008/119735 are incorporated by reference herein. Oleate hydratases from *Elizabethkingia meningoseptica* and *Streptococcus pyogenes* are encoded by ohyA and HMPREF0841_1446. Acyclic 1,2-hydratase enzymes (eg. EC 4.2.1.131) catalyze the dehydration of linear secondary alcohols, and are thus suitable candidates for the dehydration of MVC to butadiene. Exemplary 1,2-hydratase enzymes include carotenoid 1,2-hydratase, encoded by crtC of *Rubrivivax gelatinosus* (Steiger et al, Arch Biochem Biophys 414:51-8 (2003)), and lycopene 1,2-hydratase, encoded by cruF of *Synechococcus* sp. PCC 7002 and *Gemmatimonas aurantiaca* (Graham and Bryant, J Bacteriol 191: 2392-300 (2009); Takaichi et al, Microbiol 156: 756-63 (2010)). Dehydration of t-butyl alcohol, t-amyl alcohol and 2-methyl-MVC to isobutene, isoamylene and isoprene, respectively, is catalyzed by an unknown enzyme of *Aquincola tertiaricarbonis* L108 (Schaefer et al, AEM 78 (17): 6280-4 (2012); Schuster et al, J. Bacteriol 194:972-81 (2012); Schuster et al, J Bacteriol 194: 972-81 (2012)). Linalool dehydratase/isomerase of *Castellaniella defragrans* catalyzes the dehydration of linalool to myrcene (Brodkorb et al, J Biol Chem 285:30436-42 (2010)). Enzyme accession numbers and homologs are listed in the table below.

| Protein | GenBank ID | GI Number | Organism |
|---|---|---|---|
| OhyA | ACT54545.1 | 254031735 | *Elizabethkingia meningoseptica* |
| HMPREF0841_1446 | ZP_07461147.1 | 306827879 | *Streptococcus pyogenes* ATCC 10782 |
| P700755_13397 | ZP_01252267.1 | 91215295 | *Psychroflexus torquis* ATCC 700755 |
| RPB_2430 | YP_486046.1 | 86749550 | *Rhodopseudomonas palustris* |
| CrtC | AAO93124.1 | 29893494 | *Rubrivivax gelatinosus* |
| CruF | YP_001735274.1 | 170078636 | *Synechococcus* sp. PCC 7002 |
| Ldi | E1XUJ2.1 | 403399445 | *Castellaniella defragrans* |
| CGGC5_10771 | ELA28661.1 | 429853596 | *Colletotrichum gloeosporioides* Nara gc5 |
| UCRPA7_8726 | EON95759.1 | 500251895 | *Togninia minima* UCRPA7 |
| UCRNP2_8820 | EOD44468.1 | 485917493 | *Neofusicoccum parvum* UCRNP2 |
| STEHIDRAFT_68678 | EIM80109.1 | 389738914 | *Stereum hirsutum* FP-91666 SS1 |
| NECHADRAFT_82460 | XP_003040778.1 | 302883759 | *Nectria haematococca* mpVI 77-13-4 |
| AS9A_2751 | YP_004493998.1 | 333920417 | *Amycolicicoccus subflavus* DQS3-9A1 |

Dimethylmaleate hydratases catalyze the dehydration of (2R,3S)-2,3-dimethylmalate into dimethylmaleate (EC 4.2.1.85). Dimethylmaleate hydratases from *Eubacterium barkeri* are encoded by dmdA and dmdB (Alhapel et al., Proc Natl Acad Sci 103:12341-6 (2006)). (S)-2-methylmalate dehydratases catalyze the reversible hydration of mesaconate to citramalate (EC 4.2.1.34). An exemplary (S)-2-methylmalate dehydratase is encoded by LeuC and LeuD of *Methanococcus jannaschii* and has been shown to catalyze the second steop in the leucine biosynthesis pathway (Lee et al, Biochem Biophys Res Commun 419(2): 160-4 (2012)). Fumarate hydratases catalyze the interconversion of fumarate to malate (EC 4.2.1.2). Two classes of fumarate hydratases exist, where classification is dependent upon the arrangement of subunits and metal requirements. Exemplary class I and class II fumarate dehydratases are encoded by fumA and fumC of *Escherichia coli* (Tseng et al, J Bacteriol 183(2):461-7 (2001)), and fumC of *Corynebacterium glutamicum* (Genda et al, Biosci Biotechnol Biochem 70(5):1102-9 (2006)). Glycerol dehydratases (EC 4.2.1.30) catalyze the conversion of glycerol to 3-hydroxy-propionaldehyde and water. Exemplary glycerol dehydratases are encoded by dhaB of *Klebsiella pneumoniae* (Wang et al, Biotechnol J. 2(6):736-42, (2007)) and by dhaB of *Citrobacter freundii* (Seyfried et al, J Bacteriol. 178(19):5793-6 (1996)). Enoyl-CoA hydratases catalyze the hydration of the double bond between the second and third carbons on acyl-CoA (EC 4.2.1.17). Enoyl-CoA hydratases are involved in the breakdown of fatty acids. Exemplary enoyl-CoA hydratases are encoded by phaJ1 of *Pseudomonas putida* (Vo et al, J. Biosci. Bioeng. 106 (1), 95-98 (2008)), and paaF of *Escherichia coli* (Teufel et al, Proc Natl Acad Sci USA. 107(32):14390-5 (2010)).

| Protein | GenBank ID | GI Number | Organism |
|---|---|---|---|
| dmd4 | ABC88408 | 86278276 | *Eubacterium barkeri* |
| dmdB | ABC88409.1 | 86278277 | *Eubacterium barkeri* |
| LeuC | 4KP1_A | 635576713 | *Methanococcus jannaschii* |
| LeuD | Q58673.1 | 3122345 | *Methanococcus jannaschii* |
| fumA | NP_416129.1 | 16129570 | *Escherichia coli* |
| fumC | NP_416128.1 | 16129569 | *Escherichia coli* |
| fumC | BAB98403.1 | 21323777 | *Corynebacterium glutamicum* |
| phaJ1 | ABP99034.1 | 145967354 | *Pseudomonas putida* |
| paaF | P76082.1 | 2494240 | *Escherichia coli* |
| dhaB | YP_002236501.1 | 206579582 | *Klebsiella pneumoniae* |
| dhaB | AAB48850.1 | 493087 | *Citrobacter freundii* |

Dehydratase and Vinylisomerase Activity (FIG. 1 (Steps G, M) and FIG. 4 (Steps F, G and H))

Bifunctional enzymes with dehydratase and isomerase activities are suitable for dehydrating and rearranging alcohols to alkenes as shown in FIGS. 1-4. This type of enzyme is required to convert 2-hydroxypent-3-enoate to 2,4-pentadienoate (Step G of FIG. 1) and crotyl alcohol to butadiene (FIG. 1M and FIG. 4H). For example, transformation 1 G can be catalyzed by the isomerization of 2-hydroxypent-3-enoate to 4-hydroxypent-2-enoate, followed by a dehydration of 4-hydroxypent-2-enoate to 2,4-pentadienoate. An exemplary bifunctional enzyme with isomerase and dehydratase activities is the linalool dehydratase/isomerase of *Castellaniella defragrans*. This enzyme catalyzes the isomerization of geraniol to linalool and the dehydration of linalool to myrcene, reactants similar in structure to CrotOH, MVC, 2-hydroxypent-3-enoate, butadiene and 2,4-pentadienoate and is also active on crotyl alcohol (Brodkorb et al, J Biol Chem 285:30436-42 (2010)). Enzyme accession numbers and homologs are listed in the table below.

| Protein | GenBank ID | GI Number | Organism |
| --- | --- | --- | --- |
| Ldi | E1XUJ2.1 | 403399445 | Castellaniella defragrans |
| CGGC5_10771 | ELA28661.1 | 429853596 | Colletotrichum gloeosporioides Nara gc5 |
| UCRPA7_8726 | EON95759.1 | 500251895 | Togninia minima UCRPA7 |
| UCRNP2_8820 | EOD44468.1 | 485917493 | Neofusicoccum parvum UCRNP2 |
| STEHIDRAFT_68678 | EIM80109.1 | 389738914 | Stereum hirsutum FP-91666 SS1 |
| NECHADRAFT_82460 | XP_003040778.1 | 302883759 | Nectria haematococca mpVI 77-13-4 |
| AS9A_2751 | YP_004493998.1 | 333920417 | Amycolicicoccus subflavus DQS3-9A1 |

Alternatively, a fusion protein or protein conjugate can be generated using well know methods in the art to generate a bi-functional (dual-functional) enzyme having both the isomerase and dehydratase activities. The fusion protein or protein conjugate can include at least the active domains of the enzymes (or respective genes) of the isomerase and dehydratase reactions. For the first step, the conversion of CrotOH to 3-buten-2-ol or 2-hydroxypent-3-enoate to 2,4-pentadienoate, enzymatic conversion can be catalyzed by a CrotOH or 2-hydroxypent-3-enoate isomerase (classified as EC 5.3.3 and EC 5.4.4). A similar isomerization, the conversion of 2-methyl-MVC to 3-methyl-2-buten-1-ol, is catalyzed by cell extracts of Pseudomonas putida MB-1 (Malone et at, AEM 65 (6): 2622-30 (1999)). The extract may be used in vitro, or the protein or gene(s) associated with the isomerase activity can be isolated and used, even though they have not been identified to date. Alternatively, either or both steps can be done by chemical conversion, or by enzymatic conversion (in vivo or in vitro), or any combination. Crotyl alcohol can be converted to butadiene by chemical dehydration in the presence of a chemical catalyst. For example see international patent application publication WO2012106516A1.

Linalool dehydratase/isomerase, Genbank ID number 403399445, was cloned from Castellaniella defragrans 65Phen into a plasmid suitable for expression in E. coli., plasmid pZS*13S obtained from R. Lutz (Expressys, Germany) and are based on the pZ Expression System (Lutz, R. & Bujard, H. Independent and tight regulation of transcriptional units in Escherichia coli via the LacR/O, the TetR/O and AraC/I1-I2 regulatory elements. Nucleic Acids Res. 25, 1203-1210 (1997)).

E. coli variants were transformed with the expression plasmid and selected and maintained using antibiotic selection with carbenicillin. The day before the experiment, 1 mL overnight cultures in LB-antibiotic were inoculated and grown with a breathable seal in 24 well plate at 37° C. Overnight cultures were seeded at OD600=0.05 into fresh 2 mL M9+4% glucose+antibiotic+IPTG+10 mM crotyl alcohol into 10 ml screw-cap bottles. Bottles were incubated for 48 hours at 37° C. and 1,3-butadiene production was validated by headspace analysis by GC-MS. In the absence of enzyme, no production of 1,3-butadiene was observed.

5.3.3. Vinylisomerase

Vinylisomerase catalyzes the conversion of Crotyl alcohol to MVC (1K, 4F), 2-hydroxypent-3-enoate to 4-hydroxypent-2-enoate (1U), 3-hydroxypent-4-enoyl-CoA to 5-hydroxypent-2-enoyl-CoA (2M) and 2-hydroxypent-4-enoate to 5-hydroxypent-2-enoate (2E). The conversion of 3-buten-1-ol to crotyl alcohol can be carried out by vinyl-isomerases (see FIG. 2 Step S). The conversion of 3-buten-2-ol to crotyl alcohol can be carried out by vinyl-isomerases (see FIG. 1 Step W and FIG. 3 Step O). The enzymes described below naturally possess such activity or can be engineered to exhibit this activity. Intramolecular oxidoreductases that shift carbon-carbon double bonds from one position to another are found in the EC 5.3.3 enzyme class. The table below lists several useful enzymes in EC 5.3.3.

| Enzyme Commission No. | Enzyme Name |
| --- | --- |
| 5.3.3.2 | Isopentenyl-diphosphate Δ-isomerase |
| 5.3.3.3 | Vinylacetyl-CoA Δ-isomerase |
| 5.3.3.6 | Methylitaconate Δ-isomerase |
| 5.3.3.7 | Aconitate Δ-isomerase |
| 5.3.3.8 | Dodecenoyl-CoA isomerase |
| 5.3.3.10 | 5-carboxymethyl-2-hydroxymuconate Δ-isomerase |
| 5.3.3.11 | Isopiperitenone Δ-isomerase |
| 5.3.3.13 | Polyenoic fatty acid isomerase |
| 5.3.3.14 | Trans-2-decenoyl-[acyl-carrier-protein] isomerase |

Particularly useful enzymes include isopentenyl-diphosphate Δ-isomerase, vinylacetyl-CoA Δ-isomerase and methylitaconate Δ-isomerase. Enzymes candidates are described below. Also useful is the vinylisomerase activity of linalool dehydratase.

Isopentenyl diphophaste isomerases catalyze the interconversion of isopentenyl diphosphate and dimethylallyl diphosphate, but can also catalyze the interconversion of CrotOH to MVC (EC 5.3.3.2). Exemplary isopentenyl diphophaste isomerases are encoded by IDI-2 of Thermus thermophilus (Sharma et al, Biochemistry 49(29): 6228-6233 (2010)), idi of Xanthophyllomyces dendrorhous and idi of Haematococcus pluvialis (Kajiwara et al, Biochem J 324(Pt 2): 421-426 (1997)). Crystal structures have been determined for the isopentenyl diphophaste isomerases from Escherichia coli (Durbecq et al, EMBO J 20(7): 1530-1537 (2001)) and from Methanocaldococcus jannaschii (Hoshino et al, Acta Crystallogr Sect F Struct Biol Cryst Commun 67(Pt 1): 101-103 (2011)). Enzyme accession numbers and homologs are listed in the table below.

| Protein | GenBank ID | GI Number | Organism |
| --- | --- | --- | --- |
| IDI-2 | YP_006050 | 46255138 | Thermus thermophilus |
| IDI | NP_247857 | 15668172 | Methanocaldococcus jannaschii DSM 2661 |

| Protein | GenBank ID | GI Number | Organism |
|---|---|---|---|
| IDI | NP_417365.1 | 16130791 | Escherichia coli |
| IDI | AB019035.1 | 3790385 | Xanthophyllomyces dendrorhous |
| IDI | BAA33978.1 | 3790384 | Haematococcus pluvialis |
| IPI | XP_003063615 | 303289255 | Micromonas pusilla CCMP1545 |

Vinylacetyl-CoA Δ-isomerases catalyze the conversion of vinylacetyl-CoA to crotonyl-CoA (EC 5.3.3.3). Exemplary vinylacetyl-CoA Δ-isomerases are encoded by AbfD of *Clostridium kluyveri* (Scherf et al, Arch Microbiol 161(3): 239-45 (1994)), abfD of *Clostridium aminobutyricum* (Scherf et al, Eur J Biochem 215(2):421-9 (1993)), and Msed_1321 of *Metallosphaera sedula* (Auernik et al, Appl Environ Microbiol 74(3):682-92 (2008)).

| Protein | GenBank ID | GI Number | Organism |
|---|---|---|---|
| AbfD | YP_001396399 | 153955634 | Clostridium kluyveri |
| abfD | P55792.3 | 84028213 | Clostridium aminobutyricum |
| Msed_1321 | ABP95479.1 | 145702337 | Metallosphaera sedula |

Methylitaconate Δ-isomerases catalyze the isomerization of itaconate (methylenesuccinate) to citraconate (methylmaleate) (EC 5.3.3.6). An exemplary methylitaconate Δ-isomerase is encoded by mii from *Eubacterium barkeri* (Alhapel et al, Proc Natl Acad Sci USA 103(33):12341-6 (2006)) and the crystal structure of this 3-methylitaconate-delta-isomerase has been determined (Velarde et al, J Mol Biol 391(3):609-20 (2009)). Enzyme accession numbers and homologs are listed in the table below.

| Protein | GenBank ID | GI Number | Organism |
|---|---|---|---|
| Mii | Q0QLE6.1 | 122953534 | Eubacterium barkeri |
| WP_024729903 | WP_024729903.1 | 639739165 | Clostridiales bacterium |
| WP_021167098 | WP_021167098.1 | 544738199 | Sporomusa ovata |

5.4.4 Alcohol Mutases

Alcohol mutases that catalyze the conversion of 2-hydroxypent-4-enoate to 5-hydroxypent-2-enoate (2E) and 2-hydroxypent-4-enoate to 3-hydroxypent-4-enoate (2H) are found in the EC 5.4.4 enzyme class, which include isomerases that transfer hydroxyl groups. Exemplary isomerase enzymes suitable for the conversion of 2-hydroxypent-4-enoate to 5-hydroxypent-2-enoate include isochorismate synthase (EC 5.4.4.2) and geraniol isomerase (EC 5.4.4.4). Isochorismate synthase catalyzes the isomerization of chorismate to isochorismate and encodes for essential components of the respiratory chain. Exemplary isochorismate synthases are encoded by menF and dhbC of *Bacillus subtilis* (Rowland et al, J Bacteriol. 178(3):854-61 (1996)) and by menF of *Escherichia coli* (Damnwala et al, J Bacteriol. 179(10):3133-8 (1997)). Geraniol isomerase catalyzes the isomerization of (3S)-linalool to geraniol. Exemplary geraniol isomerase is encoded by Ldi of *Castellaniella defragrans* (Brodkorb et al, J Biol Chem 285:30436-42 (2010)). Enzyme accession numbers and homologs are listed in the table below.

| Protein | GenBank ID | GI Number | Organism |
|---|---|---|---|
| menF | NP_391077 | 16080250 | Bacillus subtilis |
| dhbC | NP_391079 | 255767733 | Bacillus subtilis |
| menF | NP_416768 | 90111411 | Escherichia coli |
| Ldi | E1XUJ2.1 | 403399445 | Castellaniella defragrans |
| CGGC5_10771 | ELA28661.1 | 429853596 | Colletotrichum gloeosporioides Nara gc5 |
| UCRPA7_8726 | EON95759.1 | 500251895 | Togninia minima UCRPA7 |

4.2.3 Alkenol Synthase

Alkenol synthase catalyzes the conversion of 2-butenyl-4-phosphate and 2-butenyl-4-diphosphate to 3-buten-2-ol or MVC (4D and 4E respectively). The enzymes described below naturally possess such activity or can be engineered to exhibit this activity. Particularly useful enzymes include methylbutenol (MBO) synthase, linalool synthase and nerolidol synthase. Enzyme candidates are described below and found within EC 4.2.3.

Methylbutenol synthase naturally catalyzes the conversion of dimethylallyl diphosphate to methylbutenol, but can also catalyze the synthesis of 3-buten-2-ol or MVC from 2-butenyl-4-phosphate and 2-butenyl-4-diphosphate. An exemplary methylbutenol synthase is encoded by Tps-MBO1 of *Pinus sabiniana* (Gray et al, J Biol Chem. 286 (23):20582-90 (2011)). Linalool synthases catalyze the conversion of geranyl diphosphate to linalool. Exemplary R- (EC 4.2.3.26) and S-linalool synthases (EC 4.2.3.25) are encoded by AY083653 of *Mentha citrata* (Crowell et al, Arch Biochem Biophys., 405(1): 112-21 (2002)) and by Lis of *Clarkia breweri* (Dudareva et al, Plant Cell. 8(7): 1137-1148 (1996)), respectively. (3S, 6E)-nerolidol synthase (EC 4.2.3.48) catalyze the conversion of franesyl diphosphate to nerolidol. An exemplary (3S, 6E)-nerolidol synthase is encoded by MtTps3 of *Medicago truncatula* (Arimura et al, Planta. 227(2):453-64 (2008)). Enzyme accession numbers and homologs are listed in the table below.

| Protein | GenBank ID | GI Number | Organism |
|---|---|---|---|
| Tps-MBO1 | AEB53064 | 328834891 | Pinus sabiniana |
| Tps-MBO3 | AFJ73583.1 | 387233228 | Picea pungens |
| AY083653 | AY083653 | 22900831 | Mentha citrata |
| Lis | Q96376 | 75251076 | Clarkia breweri |
| MtTps3 | AAV36466 | 54634934 | Medicago truncatula |
| Pttps3 | AEI52903 | 336318893 | Populus trichocarpa |

Butadiene Synthase (Monophosphate) or BDS

BDS (monophosphate) catalyzes the conversion of 2-butenyl-4-phosphate to 1,3-butadiene (Step 4J). BDS enzymes described above for Step C in the EC 4.2.3 enzyme class may possess such activity or can be engineered to exhibit this activity.

Example 2: Decarboxylation of 2,4-Pentadienoate to Butadiene by a Phenylacrylate Decarboxylase PadA1 (GI number: 1165293) and OhbA1 (GI number: 188496963) encoding phenylacrylate decarboxylase from *S. cerevisiae* were codon optimized by DNA 2.0 and were cloned by DNA 2.0 into the following vectors suitable for expression in *E. coli*, pD424-NH and pD441-NH respectively (DNA 2.0 Inc.). The genes were tested for decarboxylation of 2,4-pentadienoate and the enzymatic reactions were carried out under the following conditions:
100 mM Tris-HCL pH 7.2
10 mM KCL
10 mM NaCL
5 mM DTT
20 mM 2,4-Pentadienoate
1.5 mg/ml lysate of *E. coli* DH5a cells containing decarboxylase from *S. cerevisiae*

The control reactions with lysate in the absence of substrate were conducted in parallel. 100 µL reactions were incubated overnight with shaking (175 rpm) at 25° C. in 1.5 ml gas-tight vials. Headspace GCMS analysis was carried out on a 7890A GC with 5975C inert MSD using a GS-GASPRO column, 30 m×0.32 mm (Agilent Technologies). Static headspace sample introduction was performed on a CombiPAL autosampler (CTC Analytics) following 2 min incubation at 45 C. The presence of 1,3-butadiene was evaluated and the enzymatic reaction product was identified by direct comparison with a standard of 1,3-butadiene (Sigma). GC/MS analysis showed the production of 1,3-butadiene from the enzymatic samples but not from the lysate alone controls.

While no butadiene formation was detected with the no substrate-control, butadiene was measured when 2,4-PD was added as a substrate.

Example 3: Demonstration of Acetyl-CoA Reductase (1A Ad 2A), 4-Hydroxy 2-Oxovalerate Aldolase (1B and 2B), 4-Hydroxy 2-Oxovalerate Decarboxylase (1C)

Genes expressing acetyl-CoA reductase (bphJ from *Burkholderia xenovorans* LB400, GI no: 520923), 4-hydroxy 2-oxovalerate aldolase (bphI from *Burkholderia xenovorans* LB400, GI no: 520924), 4-hydroxy 2-oxovalerate decarboxylase (kdc from *Mycobacterium tuberculosis* BcG H37Rv, GI no: 614088617), and alcohol dehydrogenase (yjgB from *Chronobacter sakazakii*, GI no: 387852894) were cloned into a plasmid suitable for expression in *E. coli*, plasmid pZA23S (kanamycin resistance marker, p15A origin of replication) obtained from R. Lutz (Expressys, Germany) and are based on the pZ Expression System (Lutz, R. & Bujard, H. Independent and tight regulation of transcriptional units in *Escherichia coli* via the LacR/O, the TetR/O and AraC/I1-I2 regulatory elements. Nucleic Acids Res. 25, 1203-1210 (1997)).

*E. coli* (MG1655 variants) cells were transformed with the expression plasmid and selected and maintained using antibiotic selection with Kanamycin. Cells were grown for 72 hours in LB media with kanamycin and IPTG at 37° C. then harvested by centrifugation. The formation of a 4-carbon diol derived from 3-hydroxybutyraldehyde using glucose as the carbon substrate was measured (data not shown) while the empty vector control did not make any 4-carbon diol.

Example 4. Production of Butadiene from Crotyl Diphosphate Via Butadiene Synthase Isoprene synthase, E.C. 4.2.3.27, Genbank ID number 63108310, was cloned from *Populus alba* into a plasmid suitable for expression in *E. coli*., plasmid pZS*13S (Expressys, Germany).
*E. coli* (MG1655 variants) were transformed with the expression plasmid and selected and maintained using antibiotic selection with carbenicillin. Cells were grown in Terrific Broth with carbenicillin to an OD of 0.8 and then gene expression induced by IPTG addition then harvested by centrifugation. Lysis was performed using microfluidization at 0° C. Streptactin-tagged isoprene synthase was isolated from the cell lysate using Streptactin-Sepharose purification. Purified enzyme was tested for its ability to convert its native substrate, dimethylallyl diphosphate, into isoprene, and for its ability to convert crotyl diphosphate into 1, 3-butadiene, by incubating purified enzyme with each substrate in sealed screw-cap vials for a period of time before analysis of product in headspace of vial by GC-MS. Fidelity of purified enzyme was confirmed by detection of isoprene. Activity on crotyl diphosphate was confirmed by detection of butadiene. In the absence of enzyme, no butadiene was formed (data not shown).

Example 5. Demonstration of Crotyl Phosphate to Crotyl Phosphate Enzyme Activity Isopentenyl phosphate kinase, E.C. 2.7.4.26, Genbank ID number 2621082, was cloned from *Methanobacterium thermoautotrophicum* gi|2621082 into a plasmid suitable for expression in *E. coli*., plasmid pZS*13S obtained from R. Lutz (Expressys, Germany) and are based on the pZ Expression System (Lutz, R. & Bujard, H., Independent and tight regulation of transcriptional units in *Escherichia coli* via the LacR/O, the TetR/O and AraC/I1-I2 regulatory elements. Nucleic Acids Res. 25, 1203-1210 (1997)).

*E. coli* (MG1655 variants) were transformed with the expression plasmid and selected and maintained using antibiotic selection with carbenicillin. Cells were grown in LB media with carbenicillin and IPTG at 37° C. then harvested by centrifugation. Lysis was performed using a chemical lysis procedure, and lysate the cooled to 4° C. Streptactin-tagged isopentenyl phosphate kinase was isolated from the cell lysate using Streptactin-Sepharose purification. Activity measurements on native substrate, isopentenyl phosphate, were performed to verify fidelity of the purified enzyme, using a pyruvate kinase-lactate dehydrogenase coupled assay to couple ADP formation from ATP to NADH oxidation. The same assay procedure was used to demonstrate robust activity on crotyl phosphate. In the absence of enzyme, no conversion of crotyl phosphate to crotyl diphosphate was observed (data not shown).

Example 6: CrotOH Isomerase Activity

Isopentenyl-diphosphate DELTA-isomerase (IPP isomerase), E.C. 5.3.3.2, Genbank ID number 3790386, was cloned from *Xanthophyllomyces dendrorhous* into a plasmid suitable for expression in *E. coli*, plasmid pZS*13S obtained from R. Lutz (Expressys, Germany) and are based on the pZ Expression System (Lutz, R. & Bujard, H. Independent and tight regulation of transcriptional units in *Escherichia coli* via the LacR/O, the TetR/O and AraC/I1-I2 regulatory elements. Nucleic Acids Res. 25, 1203-1210 (1997)).

*E. coli* (MG1655 variants) were transformed with the expression plasmid and selected and maintained using antibiotic selection with carbenicillin. Cells were grown in LB media with carbenicillin and IPTG at 37° C. then harvested by centrifugation. Cell lysates containing the IPP isomerase from *Xanthophyllomyces dendrorhous* were generated by sonicating cells resuspended in 100 mM Tris, 50 mM KCl, 5 mM MgSO4, pH 7.2, and 5 mM DTT. 50 mM CrotOH was added to resulting cell lysate at 2.3 mg/ml total protein, and the reaction mixture incubated at 25° C. for 16 hours. The product of the isomerization reaction, MVC or 3-buten-2-ol, was detected at 1.2 mM by GCMS. In cell lysates devoid of the IPP isomerase, there was no detectable conversion of CrotOH to 3-buten-2-ol.

MVC or 3-buten-2-ol was measured using headspace analysis on an Agilent 7890A GC equipped with a CTC-PAL autosampler and a MSD (5975C). Samples were diluted 2-fold in 100% methanol to a total volume of 0.100 mL, and transferred into glass inserts in 1.5 mL GC vials. Samples were injected by a Combi PAL CTC autosampler operated in direct injection mode with an injection volume of 1.0 µL (split ratio 20:1) and 200° C. inlet temperature. Helium was used as a carrier gas, and the flow rate maintained at 1.28 mL/min. The oven temperature is initially held at 100° C. for 1 minute, then ramping 100° C./min to 230° C., for 3 minutes. The MVC or 3-buten-2-ol concentration in samples were calculated from calibration curves generated from diluted MVC standards analyzed under the same GCMS method.

Figure 5:
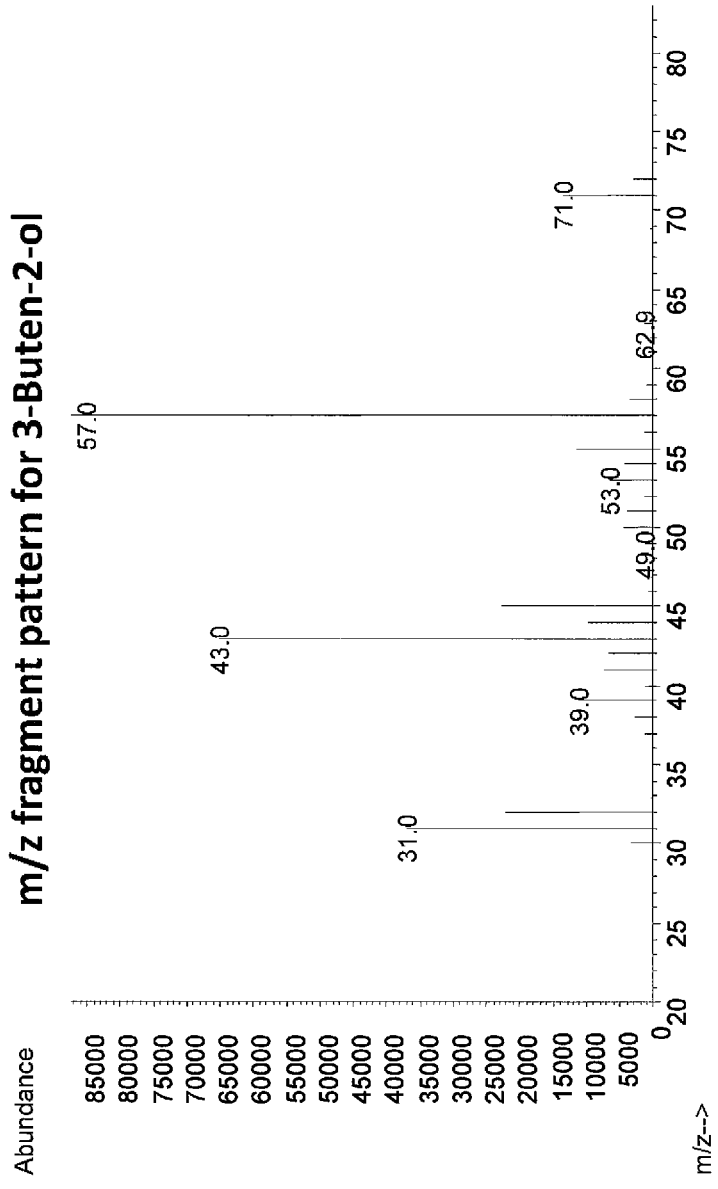
FIG. 5 shows the GCMS analysis of an authentic sample of MVC or 3-buten-2-ol.
Figure 6:
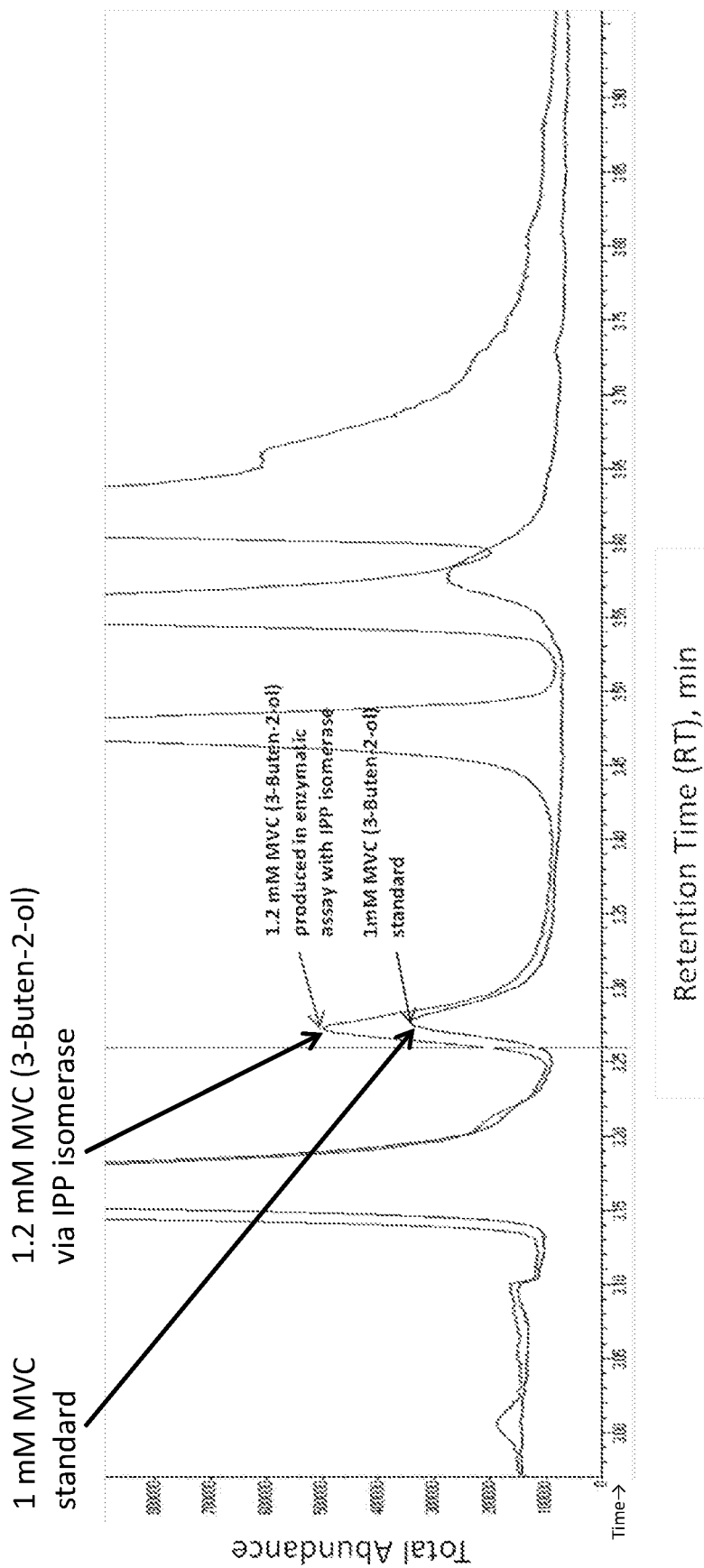
FIG. 6 shows the GCMS chromatograms obtained for the enzymatic (blue) assay with 50 mM CrotOH after 16 hours and 1 mM standard of MVC or 3-buten-2-ol dissolved in minimal media.
Figure 7:
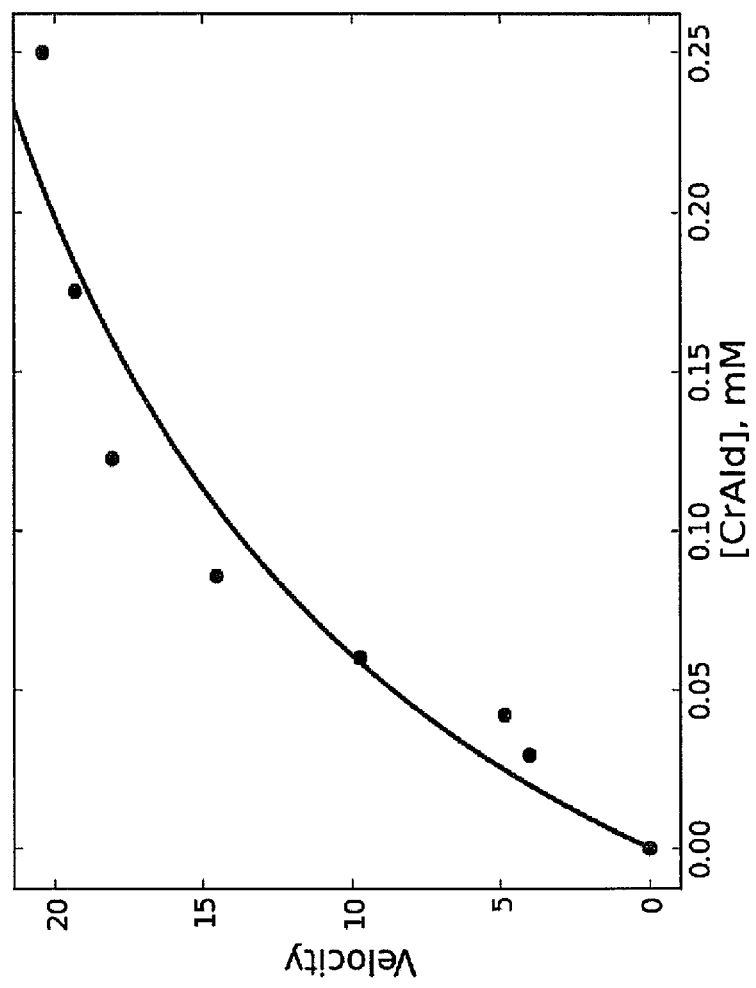
FIG. 7 is a graph showing activity measurements for assessing the NADPH-dependent reduction of crotonaldehyde to crotonol.

The results of this example are presented in FIGS. 5 and 6 in the attached slide deck. Minimal media containing 1 mM MVC or 3-buten-2-ol without *E. coli* cells showed a peak at 3.24 minutes corresponding to MVC or 3-buten-2-ol. Cell lysates containing 50 mM CrotOH and the IPP isomerase from *Xanthophyllomyces dendrorhous* showed a peak at 3.24 minutes corresponding to MVC or 3-buten-2-ol (FIG. 6). In contrast, cell lysates devoid of the IPP isomerase show no detectable MVC or 3-buten-2-ol production (data not shown). These results demonstrate that cell lysates of *E. coli* harboring the IPP isomerase from *Xanthophyllomyces dendrorhous*, isomerize CrotOH to MVC or 3-buten-2-ol.

Example 7: Crotyl Alcohol Dehydrogenase Activity

Alcohol dehydrogenase, Genbank ID number 407959257, was cloned from *Synechocystis* sp. PCC 6803 into a plasmid suitable for expression in *E. coli.*, plasmid pZS*13S obtained from R. Lutz (Expressys, Germany) and are based on the pZ Expression System (Lutz, R. & Bujard, H. Independent and tight regulation of transcriptional units in *Escherichia coli* via the LacR/O, the TetR/O and AraC/I1-I2 regulatory elements. Nucleic Acids Res. 25, 1203-1210 (1997)).

*E. coli* (MG1655 variants) were transformed with the expression plasmid and selected and maintained using antibiotic selection with carbenicillin. Cells were grown in LB media with carbenicillin and IPTG at 37° C. then harvested by centrifugation. Lysis was performed using a chemical lysis procedure, and lysate was then cooled to 4° C. Streptactin-tagged alcohol dehydrogenase was isolated from the cell lysate using Streptactin-Sepharose purification. Activity measurements assessing the NADPH-dependent reduction of crotonaldehyde to crotonol were performed. The alcohol dehydrogenase from *Synechocystis* sp. PCC 6803 was found to have a KM value of 0.16 mM and a Kcat of at least 36 s-1. In the absence of enzyme, no reduction of crotonaldehyde to crotonol was observed.

What is claimed is:

1. A non-naturally occurring microbial organism having a pathway from acetyl CoA to butadiene, said microbial organism comprising at least one exogenous nucleic acid encoding an enzyme of said pathway, wherein said pathway comprises one of groups (i)-(xi) of enzymes:
   (i) 1A, 1B, 1E, 1N, 1O, 1P, 1Q, and 1H;
   (ii) 1A, 1B, 1E, 1F, 1R, 1P, 1Q, and 1H;
   (iii) 1A, 1B, 1E, 1G, and 1H;
   (iv) 1A, 1B, 1E, 1F, 1U, 1V, and 1H;
   (v) 1A, 1B, 1E, 1F, 1U, 1T, and 1L;
   (vi) 1A, 1B, 1E, 1F, 1S, and 1M;
   (vii) 1A, 1B, 1E, 1F, 1S, 1K, and 1L;
   (viii) 1A, 1B, 1E, 1I, 1J, and 1M;
   (ix) 1A, 1B, 1E, 1I, 1J, 1K, and 1L;
   (x) 1A, 1B, 1C, 1D, 1J, and 1M; and
   (xi) 1A, 1B, 1C, 1D, 1J, 1K, and 1L; as follows:
   (1A) acetyl-CoA reductase, (1B) 4-hydroxy 2-oxovalerate aldolase, (1C) 4-hydroxy 2-oxovalerate decarboxylase, (1D) 3-hydroxybutyraldehyde dehydratase, (1E) 4-hydroxy-2-oxovalerate 3-dehydratase, (1F) 2-oxopent-3-enoate reductase, (1G) 2-hydroxypent-3-enoate dehydratase/vinylisomerase, (1H) 2,4-pentadienoate decarboxylase, (1I) 2-oxopent-3-enoate decarboxylase, (1J) crotyl aldehyde reductase, (1K) crotyl alcohol vinylisomerase, (1L) 3-buten-2-ol dehydratase, (1M) crotyl alcohol dehydratase/vinylisomerase, (1N) 2-oxopent-3-enoyl-CoA synthetase or transferase, (1O) 2-oxopent-3-enoyl-CoA reductase, (1P) 2-hydroxypent-3-enoyl-CoA dehydratase/vinylisomerase, (1Q) 2,4-pentadienoyl-CoA synthetase, transferase or hydrolase, (1R) 2-hydroxypent-3-enoyl-CoA synthetase or transferase, (1S) 2-hydroxypent-3-enoate decarboxylase, (1T) 4-hydroxypent-2-enoate decarboxylase, (1U) 2-hydroxypent-3-enoate vinylisomerase (1V) 4-hydroxypent-2-enoate dehydratase.

2. The non-naturally occurring microbial organism of claim 1 comprising at least one exogenous nucleic acid encoding (1B) 4-hydroxy 2-oxovalerate aldolase.

3. The non-naturally occurring microorganism of claim 1, further comprising a nucleic acid encoding an enzyme selected from an alcohol dehydrogenase, an acyl-CoA reductase, a CoA transferase, a CoA hydrolase, a decarboxylase, an aldolase, a dehydratase, a dehydratase/vinylisomerase, an isomerase, a CoA synthetase, or combinations thereof.

4. The non-naturally occurring microorganism of claim 1, further comprising nucleic acids encoding enzymes that are (1B) 4-hydroxy 2-oxovalerate aldolase; (1A) acetyl-CoA reductase; and (1F) 2-oxopent-3-enoate reductase.

5. The non-naturally occurring microorganism of claim 4, comprising nucleic acids encoding enzymes of group III, IV, V, VI, or VII:
   III: (1P) 2-hydroxypent-3-enoyl-CoA dehydratase/vinylisomerase, (1Q) 2,4-pentadienoyl-CoA synthetase, transferase or hydrolase, (1R) 2-hydroxypent-3-enoyl-CoA synthetase or transferase, and (1H) 2,4-pentadienoate decarboxylase;
   IV: (1G) 2-hydroxypent-3-enoate dehydratase/vinylisomerase, and (1H) 2,4-pentadienoate decarboxylase;
   V: (1U) 2-hydroxypent-3-enoate vinylisomerase, (1V) 4-hydroxypent-2-enoate dehydratase, and (1H) 2,4-pentadienoate decarboxylase;
   VI: (1S) 2-hydroxypent-3-enoate decarboxylase, (1K) crotyl alcohol vinylisomerase, and (1L) 3-buten-2-ol dehydratase; or
   VII: (1U) 2-hydroxypent-3-enoate vinylisomerase, (1T) 4-hydroxypent-2-enoate decarboxylase, and (1L) 3-buten-2-ol dehydratase.

6. The non-naturally occurring microorganism of claim 2, comprising a nucleic acid encoding (1I) 2-oxopent-3-enoate decarboxylase.

7. The non-naturally occurring microorganism of claim 6, comprising nucleic acids encoding enzymes of group VIII or IX:
   VIII: (1J) crotyl aldehyde reductase, (1K) crotyl alcohol vinylisomerase, and (1L) 3-buten-2-ol dehydratase; or
   IX: (1J) crotyl aldehyde reductase, and (1M) crotyl alcohol dehydratase/vinylisomerase.

8. The non-naturally occurring microorganism of claim 2, comprising nucleic acids encoding (1N) 2-oxopent-3-enoyl-CoA synthetase or transferase, (1O) 2-oxopent-3-enoyl-CoA reductase, (1P) 2-hydroxypent-3-enoyl-CoA dehydratase/vinylisomerase, (1Q) 2,4-pentadienoyl-CoA synthetase, transferase or hydrolase, and (1H) 2,4-pentadienoate decarboxylase.

9. The non-naturally occurring microbial organism of claim 1 comprising an exogenous nucleic acid encoding (1D) 3-hydroxybutyraldehyde dehydratase.

10. The non-naturally occurring microorganism of claim 9, comprising a nucleic acid or nucleic acids encoding one or more enzyme(s) selected from an enzyme(s) of group X, XI, or XII:
   X: (1C) 4-hydroxy 2-oxovalerate decarboxylase;
   XI: (1J) crotyl aldehyde reductase, (1K) crotyl alcohol vinylisomerase, and (1L) 3-buten-2-ol dehydratase; or
   XII: (1J) crotyl aldehyde reductase, and (1M) crotyl alcohol dehydratase/vinylisomerase.

11. A method for the production of butadiene, comprising culturing the non-naturally occurring microorganism of claim 1 under conditions to produce butadiene, optionally wherein the culturing comprises substantially anaerobic conditions.

12. The non-naturally occurring microorganism of claim 1, comprising nucleic encoding (2A) acetyl-CoA reductase, (2B) 4-hydroxy 2-oxovalerate aldolase, (2C) 4-hydroxy 2-oxovalerate dehydratase, and (2D) 2-oxopent-4-enoate reductase.

13. The non-naturally occurring microorganism of claim 1, comprising (2E) 2-hydroxypent-4-enoate vinylisomerase.

14. The non-naturally occurring microorganism of claim 13, comprising nucleic acids of group I or II:
   I: nucleic acids encoding (2P) 5-hydroxypent-2-enoate decarboxylase and (2Q); or
   II: nucleic acids encoding (2F) 5-hydroxypent-2-enoate dehydratase and (2G) 2,4-pentadienoate decarboxylase.

15. The non-naturally occurring microorganism of claim 1, comprising (2H) 2-hydroxypent-4-enoate mutase.

16. The non-naturally occurring microbial organism of claim 1 wherein said pathway includes 4-hydroxy-2-oxovalerate as a pathway intermediate compound.

17. The non-naturally occurring microbial organism of claim 16 wherein said pathway includes (i) 4-hydroxy-2-oxovalerate and (ii) 2-oxopent-3-enoate or 2-oxopent-4-enoate, as pathway intermediate compounds.

18. The non-naturally occurring microbial organism of claim 1 wherein said pathway is:
   (viii) 1A, 1B, 1E, 1I, 1J, and 1M.

19. The non-naturally occurring microbial organism of claim 1 that is bacteria.

20. The non-naturally occurring microbial organism of claim 19 that is *E. coli*.

* * * * *